United States Patent
Hochedlinger et al.

(10) Patent No.: US 10,059,945 B2
(45) Date of Patent: Aug. 28, 2018

(54) METHODS OF CONTROLLING CELL FATE AND CONSEQUENCES FOR DISEASE

(71) Applicant: THE GENERAL HOSPITAL CORPORATION, Boston, MA (US)

(72) Inventors: Konrad Hochedlinger, Boston, MA (US); Sihem Cheloufi, Boston, MA (US); Marti Anne Borkent, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/443,632

(22) Filed: Feb. 27, 2017

(65) Prior Publication Data

US 2017/0175120 A1  Jun. 22, 2017

Related U.S. Application Data

(63) Continuation of application No. PCT/US2015/046903, filed on Aug. 26, 2015.

(60) Provisional application No. 62/041,960, filed on Aug. 26, 2014, provisional application No. 62/041,968, filed on Aug. 26, 2014.

(51) Int. Cl.
   C12N 15/11    (2006.01)
   C12N 15/113   (2010.01)
   C12N 5/074    (2010.01)

(52) U.S. Cl.
   CPC .......... *C12N 15/113* (2013.01); *C12N 5/0696* (2013.01); *C12N 2310/14* (2013.01); *C12N 2310/141* (2013.01); *C12N 2310/531* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/998* (2013.01); *C12N 2506/1307* (2013.01); *C12N 2506/30* (2013.01)

(58) Field of Classification Search
   None
   See application file for complete search history.

(56) References Cited

U.S. PATENT DOCUMENTS

| | | |
|---|---|---|
| 7,595,167 B2 | 9/2009 | Khan et al. |
| 7,771,937 B2 | 8/2010 | Moon et al. |
| 2003/0170678 A1 | 9/2003 | Tanzi et al. |
| 2010/0249107 A1 | 9/2010 | Singer |
| 2011/0172107 A1 | 7/2011 | Katz et al. |
| 2013/0149320 A1 | 6/2013 | Almouzni et al. |
| 2017/0211048 A1* | 7/2017 | Elling .................. C12N 5/0696 |

FOREIGN PATENT DOCUMENTS

| | | |
|---|---|---|
| WO | 2009/009457 A1 | 1/2009 |
| WO | 2010/048497 A1 | 4/2010 |

OTHER PUBLICATIONS

Houlard M, Berlivet S, Probst AV, et al. CAF-1 is Essential for Heterochromatin Organization in Pluripotent Embryonic Cells. Reik W, ed. PLoS Genetics. 2006;2(11):e181. doi:10.1371/journal.pgen.0020181.
Feng, B et al. Molecules That Promote or Enhance Reprogramming of Somatic Cells to Induced Pluripotent Stem Cells. Cell Stem Cell. Apr. 3, 2009, vol. 4, pp. 301-312. DQI: 10.1016/j.stem.2009.03.005.
Tahmasebi, S et al. Sumoylation of Kruppel-Like Factor 4 Inhibits Pluripotency Induction But Pruniutes Adipocyte Differentiation. I he Journal of Biological Chemistry. May 3, 2013, vol. 288, No. 18, pp. 12791-12804. DOI: 10.1074/jbc.M113.465443.
Apostolou et al., "Chromatin Dynamics during Cellular Reprogramming", Nature 502(7472):462-471 (2013).
Bar-Nur et al., "Small molecules facilitate rapid and synchronous iPSC generation", Nat. Methods 11(11):1170-1176 (2014).
Di Giammartino et al., Mechanisms and consequences of alternative polyadenylation, Mol. Cell. 43(6):853-866 (2011).
Esteban et al., "Vitamin C Enhances the Generation of Mouse and Human Induced Pluripotent Stem Celle", Cell Stem Cell 6:71-79 (2010).
Flotho et al., "Sumoylation: a Regulatory Protein Modification in Health and Disease", Annu. Rev. Biochem. 82:357-385 (2013).
Hanna et al., "Direct cell reprogramming is a stochastic process amenable to acceleration", Nature 462 (7273):595-601 (2009).
Hickey et al., "Function and Regulation of SUMO Proteases", Nat Rev. Mol. Cell. Biol. 13(12):755-766 (2012).
Hoek et al., "Chromatin assembly factor 1 is essential and couples chromatin assembly to DNA replication in vivo", Proc. Natl. Acad. Sci. USA 100(21):12183-12188 (2003).
Hoover et al., "Tau mislocalization to dendritic spines mediates synaptic dysfunction independently of neurodegeneration", Neuron 68(6):1067-1081 (2010).
Huangfu et al., "Induction of pluripotent stem cells by defined factors is greatly improved by small-molecule =compounds", Nat. Biotechnol. 26(7):795-797 (2008).
Jackson-Grusby et al., "Loss of genomic methylation causes p53-dependent apoptosis and epigenetic deregulation", Nat. Gene. 27:31-39 (2001).
Krizhanovsky et al., "The promises and perils of p53", Nature 460(7259):1085-1086 (2009).
Maherali et al., "A High-Efficiency System for the Generation and Study of Human Induced Pluripotent Stem Cells", Cell Stem Cell 3:340-345 (2008).
Marson et al., Wnt signaling promotes reprogramming of somatic cells to pluripotency, Cell Stem Cell 3(2):132-135 (2008).

(Continued)

*Primary Examiner* — Dana H Shin
(74) *Attorney, Agent, or Firm* — David S. Resnick; Nixon Peabody LLP

(57) ABSTRACT

Provided herein are methods for performing cellular reprogramming that include treatment of somatic cells with an inhibitor of CAF-1, Sumo2, Nutd21, or combinations thereof prior to or during a reprogramming procedure. Such inhibitors can improve both the speed and efficiency of cellular reprogramming. Inhibitors of the CAF-1 complex can also be used in the treatment of cancer.

10 Claims, 41 Drawing Sheets

Specification includes a Sequence Listing.

(56) References Cited

OTHER PUBLICATIONS

Matoba et al., "Privileged Communication Embryonic Development Following Somatic Cell Nuclear Transfer Impeded by Persisting Histone Methylation", Cell 159(4):884-895 (2014).
Mikkelsen et al., "Dissecting direct reprogramming through integrative genomic analysis", Nature 454(7200):49-55 (2008).
Neyret-Kahn et al., "Sumoylation at chromatin governs coordinated repression of a transcriptional program essential for cell growth and proliferation", Genome Res. 23:1563-1579 (2013).
Onder et al., "Chromatin modifying enzymes as modulators of reprogramming", Nature 483(7391):598-602 (2012).
Poleshko et al., "Human factors and pathways essential for mediating epigenetic gene silencing", Epigenetics 9 (9):1280-1289 (2014).
Polo et al., "A molecular roadmap of cellular reprogramming into iPS cells", Cell 151(7):1617-1632 (2012).
Polo et al., "Clinical significance and prognostic value of chromatin assembly factor-1 overexpression in human solid tumours", Histopathology 57:716-724 (2010).
Polo et al., "When Fibroblasts MET iPSCs", Cell Stem Stem 7:5-6 (2010).
Pooler et al., Physiological release of endogenous tau is stimulated by neuronal activity, EMBO Rep. 14 (4):389-394 (2013).
Qin et al., "Systematic Identification of Barriers to Human iPSC Generation", Cell 158(2):449-461 (2014).
Quivy et al., "The HP1-p150/CAF-1 interaction is required for pericentric heterochromatin replication and S-phase progression in mouse cells", Nat. Struct. Mol. Biol. 15(9):972-979 (2008).
Rais et al., "Deterministic direct reprogramming of somatic cells to pluripotency", Nature 502:65-70 (2013).
Samavarchi-Tehrani et al., "Functional Genomics Reveals a BMP-Driven Mesenchymal-to-Epithelial Transition in the Initiation of Somatic Cell Reprogramming", Cell Stem Cell 7:64-77 (2010).
Shi et al., A Combined Chemical and Genetic Approach for the Generation of Induced Pluripotent Stem Cells, Cell Stem Cell 2:525-528 (2008).
Stadtfeld et al., "A reprogrammable mouse strain from gene targeted embryonic stem cells", Nat. Methods 7 (1):53-55 (2010).
Stadtfeld et al. "Induced pluripotency: history, mechanisms, and applications", Genes Dev. 24:2239-2263 (2010).
Stadtfelt et al., "Defining molecular cornerstones during fibroblast to iPS cell reprogramming in mouse", Cell Stem Cell 2(3):230-240 (2008).
Staftfeld et al., "Ascorbic acid prevents loss of Dlk1-Dio3 imprinting and facilitates generation of all-iPS cell mice from terminally differentiated B cells", Nat. Genet 44(4):398-405 (2012).
Tahmasebi et al., "The SUMO Conjugating Enzyme Ubc9 is Required for Inducing and Maintaining Stem Cell Pluripotency", Stem Cells 32:1012-1020 (2014).
Takeda et al., "Neuronal uptake and propagation of a rare phosphorylated high-molecular-weight tau derived from Alzheimer's disease brain", Nat. Commun. 6:8490 (2015).
Takeda et al., "Seed-Competent High-Molecular-Weight Tau Species Accumulates in the Cerebrospinal Fluid of Alzheimer's Disease Mouse Model and Human Patients", Ann. Neural. 80:355-367 (2016).
Tatham et al., "Polymeric Chains of SUMO-2 and SUMO-3 Are Conjugated to Protein Substrates by SAE1/SAE2 and Ubc9", J. Biol. Chem. 276(38):35368-35374 (2001).
Theunissen et al., "Molecular Control of Induced Pluripotency", Cell Stem Cell 14:720-734 (2014).
Tsuruzoe et al., "Inhibition of DNA binding of Sox2 by the SUMO conjugation", Biochem. Biophys. Res. Commun. 351:920-926 (2006).
Vierbuchen et al., "Molecular roadblocks for cellular reprogramming", Mol. Cell. 47(6):827-838 (2012).
Walker et al., "Mechanisms of Protein Seeding in Neurodegenerative Diseases", JAMA Neural. 70(3):304-310 (2013).
Wang et al., "SUMO2 is essential while SUMO3 is dispensable for mouse embryonic development", EMBO Rep. 15 (8):878-885 (2014).
Wang et al., "The Histone Demethylases Jhdm1a/1b Enhance Somatic Cell Reprogramming in a Vitamin-C-Dependent Manner", Cell Stem Cell 9(6):575-587 (2011).
Wegmann et al., "Removing endogenous tau does not prevent tau propagation yet reduces its neurotoxicity", EMBO J. 34(24):3028-3041 (2015).
Wu et al., "SUMOylation Represses Nanog Expression via Modulating Transcription Factors Oct4 and Sox2", PLoS One 7(6):e39606 (2012).
Yang et al., "Genome-wide functional analysis reveals factors needed at the transition steps of induced reprogramming", Cell Rep. 8(2):327-337 (2014).
Yang et al. "Sumoylation in gene regulation, human disease, and therapeutic action", F1000Prine Rep. 5:45 (2013).
Ye et al., "Defective S Phase Chromatin Assembly Causes DNA Damage, Activation of the S Phase Checkpoint, and S Phase Arrest", Mol. Cell 11:341-351 (2003).

\* cited by examiner

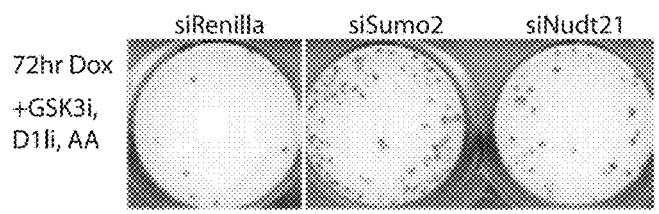
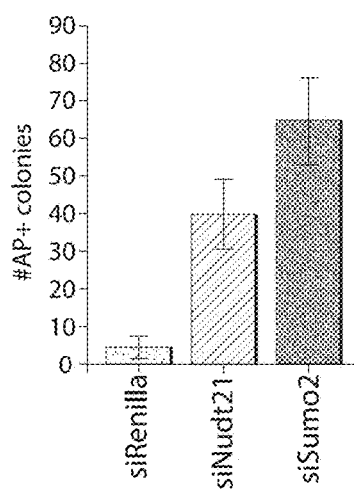
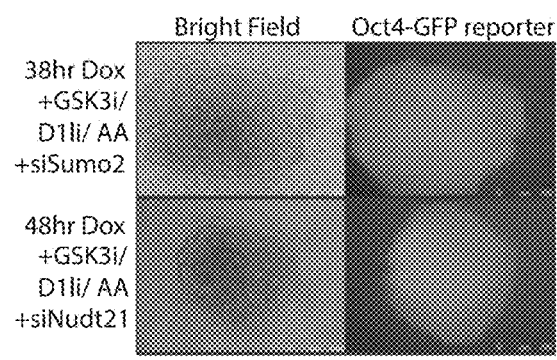
Fig. 5A
Fig. 5B
Fig. 5C

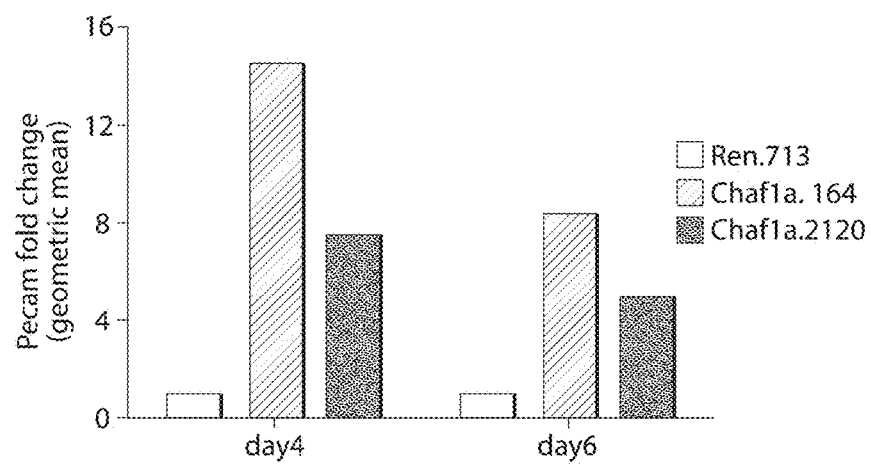
Fig. 13C
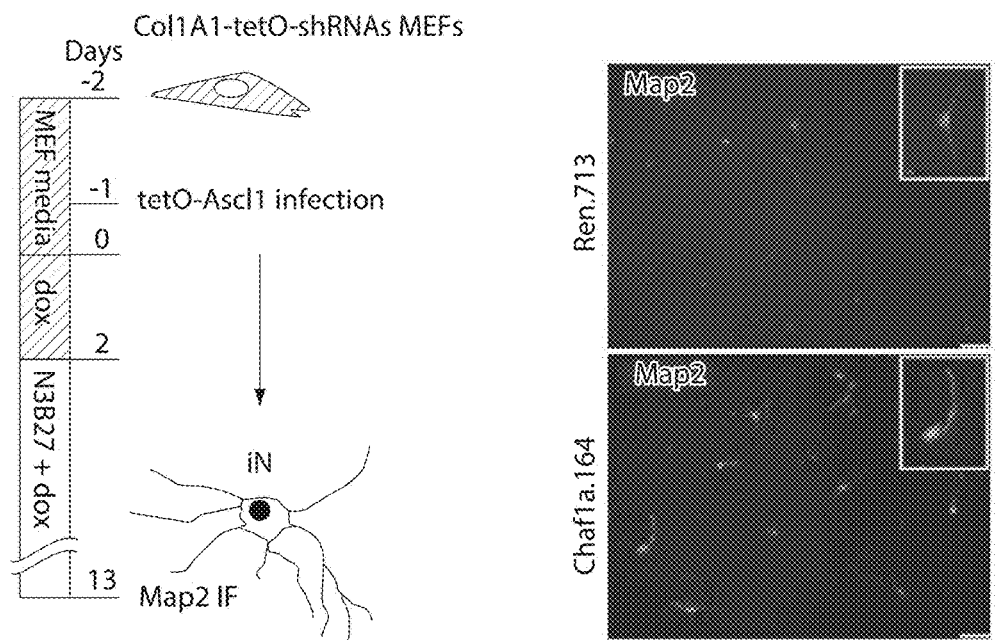
Fig. 13D
Fig. 13E

METHODS OF CONTROLLING CELL FATE AND CONSEQUENCES FOR DISEASE

CROSS-REFERENCE TO RELATED APPLICATIONS

This application claims the benefit under 35 U.S.C. § 120 and is a Continuation of International PCT Application No. PCT/US2015/046903 filed Aug. 26, 2015, which claims the benefit under 35 U.S.C. § 119(e) of U.S. Provisional Patent Application Ser. No. 62/041,960 filed Aug. 26, 2014 and U.S. Provisional Patent Application Ser. No. 62/041,968 filed Aug. 26, 2014, the contents of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Sep. 22, 2015, is named 030258-085430-PCT_SL.txt and is 5,639 bytes in size.

FIELD OF THE INVENTION

The field of the invention relates to methods and compositions for enhancing cellular reprogramming and for modifying cell fate for the treatment of disease.

BACKGROUND

Mammalian development is a unidirectional process that depends on the proper establishment and maintenance of lineage-specific transcriptional programs to generate a multitude of differentiated cell types (1-3). Genome-wide analyses of gene expression, chromatin structure and associated modifications during distinct stages of development and across different somatic cell types support the notion that cell identity is maintained by stable and conserved chromatin pathways (4). However, the regulators and mechanisms responsible for preserving these cellular states remain poorly understood.

Ectopic expression of transcription factors is sufficient to override stable epigenetic programs and hence alter cell fate (5). For example, forced expression of pluripotency-related transcription factors in somatic cells yields induced pluripotent stem cells (iPSCs), which are transcriptionally, epigenomically, and functionally equivalent to embryonic stem cells (ESCs) (6). Similarly, forced expression of lineage-specific transcription factors drives conversion of heterologous cells into cardiac, neuronal, myeloid and other specialized cell types (7). Reprogramming transcription factors such as Oct4 and Sox2 are thought to act as "pioneer factors", which bind to nucleosomal DNA and gradually remodel local chromatin structure to activate target genes (8). However, the reprogramming process is generally slow and inefficient, coinciding with multiple rounds of cell division and recruitment of additional cofactors.

SUMMARY

The methods and treatments described herein are based, in part, on the discovery that inhibitors of the CAF-1 complex, inhibitors of Sumo2, and inhibitors of Nutd21 can be used in a cellular reprogramming protocol, and surprisingly can increase the speed and/or efficiency of cellular reprogramming of somatic cells to induced pluripotent stem cells (iPSCs).

Accordingly, provided herein in one aspect is a method for performing cellular reprogramming, the method comprising: (a) contacting a somatic cell with an inhibitor of the CAF-1 complex, Nudt21, or Sumo2, and (b) subjecting the somatic cell to a reprogramming protocol, thereby reprogramming the somatic cell to an induced pluripotent stem cell (iPSC).

In one embodiment of this aspect and all other aspects described herein, the speed and/or efficiency of cellular reprogramming to iPSCs is increased in the presence of the inhibitor as compared to the speed and/or efficiency of cellular reprogramming performed in the absence of the inhibitor.

In another embodiment of this aspect and all other aspects described herein, the measure of efficiency of cellular reprogramming comprises an increase in the total number of reprogrammed cells relative to reprogramming in the absence of a said inhibitor.

In another embodiment of this aspect and all other aspects described herein, the measure of speed of cellular reprogramming comprises the appearance of reprogrammed cells at an earlier time point than occurs when reprogramming in the absence of said inhibitor.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, step (a) is performed before or during step (b).

In another embodiment of this aspect and all other aspects described herein, the reprogramming of step (b) comprises induction of Oct-4/Klf4/Sox-2/c-Myc (OKSM) expression.

In another embodiment of this aspect and all other aspects described herein, the reprogramming step does not comprise forced expression of c-Myc.

In another embodiment of this aspect and all other aspects described herein, the somatic cell comprises a fibroblast.

In another embodiment of this aspect and all other aspects described herein, the inhibitor of the CAF-1 complex inhibits the Chaf1a and/or Chaf1b subunit of said complex.

Another aspect provided herein relates to a method of inducing differentiation of a cancer cell or cancer stem cell in vivo, the method comprising: administering an inhibitor of the CAF-1 complex to a subject having, or suspected of having cancer, thereby inducing differentiation of the cancer cell or cancer stem cell in vivo.

In one embodiment of this aspect and all other aspects provided herein, the cancer comprises leukemia.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, the inhibitor inhibits the Chaf1a and/or Chaf1b subunit of the CAF-1 complex.

Also provided herein in another aspect is a composition comprising: one or more inhibitors of the CAF-1 complex, Nudt21, or Sumo2 and a pharmaceutically acceptable carrier.

In one embodiment of this aspect and all other aspects described herein, the composition comprises inhibitors or any two or all of the CAF-1 complex, Nudt21 and Sumo2.

Another aspect provided herein relates to a composition for use in cellular reprogramming, the composition comprising an inhibitor of the CAF-1 complex, Nudt21, or Sumo2.

In one embodiment of this aspect and all other aspects provided herein, the composition further comprises a pharmaceutically acceptable carrier.

In another embodiment of this aspect and all other aspects described herein, the inhibitor increases the total number of reprogrammed cells relative to reprogramming in the absence of the inhibitor.

In another embodiment of this aspect and all other aspects described herein, the inhibitor promotes the appearance of reprogrammed cells at an earlier time point than occurs when cells are reprogrammed in the absence of the inhibitor.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, cellular reprogramming comprises induction of Oct-4/Klf4/Sox-2/c-Myc (OKSM) expression.

In another embodiment of this aspect and all other aspects described herein, cellular reprogramming does not comprise forced expression of c-Myc.

In another embodiment of this aspect and all other aspects described herein, cellular reprogramming comprises reprogramming of a fibroblast.

In another embodiment of this aspect and all other aspects described herein, the inhibitor of the CAF-1 complex inhibits the Chaf1a and/or Chaf1b subunit of the complex.

Another aspect provided herein relates to the use of an inhibitor of the CAF-1 complex, Nudt21, or Sumo2 for cellular reprogramming.

In one embodiment of this aspect and all other aspects described herein, the inhibitor increases the speed and/or efficiency of cellular reprogramming.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, cellular reprogramming comprises induction of Oct-4/Klf4/Sox-2/c-Myc (OKSM) expression.

In another embodiment of this aspect and all other aspects described herein, the cellular reprogramming does not comprise forced expression of c-Myc.

In another embodiment of this aspect and all other aspects described herein, cellular reprogramming comprises reprogramming of a fibroblast.

In another embodiment of this aspect and all other aspects described herein, the inhibitor of the CAF-1 complex inhibits the Chaf1a and/or Chaf1b subunit of the complex.

Another aspect provided herein relates to a composition for use in the treatment of cancer, the composition comprising an inhibitor of the CAF-1 complex.

In one embodiment of this aspect and all other aspects provided herein, the composition induces the differentiation of a cancer cell or cancer stem cell in vivo when administered to an individual having cancer.

In another embodiment of this aspect and all other aspects described herein, the composition further comprises a pharmaceutically acceptable carrier.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, the cancer comprises a leukemia.

In another embodiment of this aspect and all other aspects described herein, the inhibitor inhibits the Chaf1a and/or Chaf1b subunit of the CAF-1 complex.

Also provided herein in another aspect is the use of an inhibitor of the CAF-1 complex for the treatment of cancer, the use comprising administering said inhibitor of the CAF-1 complex to an individual having cancer.

In one embodiment of this aspect and all other aspects provided herein, the administering induces the differentiation of a cancer cell or cancer stem cell, thereby treating said cancer.

In another embodiment of this aspect and all other aspects described herein, the inhibitor comprises an RNA interference molecule or an antibody.

In another embodiment of this aspect and all other aspects described herein, the RNA interference molecule comprises an siRNA or an shRNA.

In another embodiment of this aspect and all other aspects described herein, the cancer comprises a leukemia.

In another embodiment of this aspect and all other aspects described herein, the inhibitor inhibits the Chaf1a and/or Chaf1b subunit of the CAF-1 complex.

Also provided herein, in another aspect, is a method for performing cellular transdifferentiation, the method comprising: (a) contacting a somatic cell with an inhibitor of the CAF-1 complex, and (b) subjecting the somatic cell to a transdifferentiation protocol, thereby transdifferentiating the somatic cell to a different cell type.

In one embodiment of this aspect and all other aspects provided herein, the speed and/or efficiency of cellular transdifferentiation is increased in the presence of the inhibitor as compared to the speed and/or efficiency of cellular reprogramming performed in the absence of the inhibitor.

In another embodiment of this aspect and all other aspects provided herein, the measure of efficiency of cellular transdifferentiation comprises an increase in the total number of transdifferentiated cells relative to transdifferentiation in the absence of a said inhibitor.

In another embodiment of this aspect and all other aspects provided herein, the measure of speed of cellular transdifferentiation comprises the appearance of transdifferentiated cells at an earlier time point than occurs when cells are transdifferentiated in the absence of said inhibitor.

In another embodiment of this aspect and all other aspects provided herein, the inhibitor comprises an RNA interference molecule or an antibody.

In another embodiment of this aspect and all other aspects provided herein, the RNA interference molecule comprises an siRNA or an shRNA.

In another embodiment of this aspect and all other aspects provided herein, step (a) is performed before or during step (b).

In another embodiment of this aspect and all other aspects provided herein, the transdifferentiation of step (b) comprises transdifferentiation of a fibroblast to a neuron or transdifferentiation of a B-cell to a macrophage.

In another embodiment of this aspect and all other aspects provided herein, transdifferentiation of a fibroblast to a neuron comprises overexpression (e.g., forced expression) of the transcription factor Ascl1 in a fibroblast.

In another embodiment of this aspect and all other aspects provided herein, transdifferentiation of a B-cell to a macrophage comprises overexpression (e.g., forced expression) of the myeloid transcription factor C/EBPα in a B-cell.

In another embodiment of this aspect and all other aspects provided herein, the inhibitor of the CAF-1 complex inhibits the Chaf1a and/or Chaf1b subunit of said complex.

BRIEF DESCRIPTION OF THE FIGURES

FIG. 1 describes a serial genome-wide shRNA enrichment screen during iPSC generation. FIG. 1A, Fluorescence microscopy image of a primary iPSC colony showing lentiviral tRFP expression and activation of the endogenous Oct4-GFP pluripotency reporter. FIG. 1B, Flow cytometric analysis of tRFP (y axis) and Oct4-GFP (x-axis) expression of MEFs having undergone reprogramming with gating strategy to purify Oct4-GFP+ cells. FIG. 1C, Timeline of reprogramming experiments and strategy to collect control and experimental samples for subsequent analysis of shRNA library representation. FIG. 1D Schematic representation of steps required for every reprogramming and shRNA enrichment cycle. FIG. 1E Overview of serial enrichment screen and validation experiments. FIG. 1F Change in shRNA library complexity during initial screen, i.e., number of unique shRNAs at the start of rounds 1-3. FIG. 1G, Enrichment of candidate shRNAs during the first 3 rounds of reprogramming from screen #1. Lines depict hairpins that enhanced iPSC formation more than 2-fold. FIG. 1H, Validation experiments screen #1. FIG. 1I, Gradual loss of shRNA library complexity during repeat screen; i.e., number of unique shRNAs at the start of rounds 1-5. FIG. 1J, Heatmap depicting fold-change enrichment of shRNAs during 5 rounds of reprogramming from screen #2. Note that blue bars represent shRNA that were lost whereas red bars represent shRNA that became enriched relative to controls (see text and methods section for details). FIG. 1K, Validation experiments screen #2.

FIG. 2 demonstrates that suppression of Nudt21 and Sumo2 strongly enhances and accelerates reprogramming. FIG. 2A, Flow cytometric analysis of Oct4-GFP expression in reprogrammable MEFs after 8 days or OKSM expression in the presence of hairpins against Firefly luciferase (control), Sumo2 or Nudt21. tRFP expression depicts cells carrying lentiviral shRNA vector. FIG. 2B, Quantification of data shown in FIG. 2A; shown is percentage of Oct4-GFP+ cells per total number of cells using three replicates. FIG. 2C, Alkaline Phosphatase (AP) staining for iPSC colonies derived from reprogrammable MEFs transfected once with siRNAs targeting Renilla (control), Nudt21 or Sumo2 during reprogramming. FIG. 2D, Quantification of data shown in FIG. 2C; data obtained from three independent replicates. FIGS. 2E-2F, Western blot analyses for Nudt21 (FIG. 2E) and Sumo2 (FIG. 2F) expression in reprogrammable MEFs infected with respective shRNA vectors and treated with doxycycline (dox) for 3 days. FIG. 2G, Expression dynamics of Nudt21 and Sumo2 in MEFs, iPSCs and intermediate stages of reprogramming. Note that expression of either gene does not change dramatically compared to controls (Thy1, fibroblast marker; Nanog, pluripotency marker). FIG. 2H, Scheme to determine minimal duration of OKSM expression (in days) required to achieve transgene-independent iPSC colonies. FIG. 2I, Data obtained from experiments depicted in FIG. 2G using shRNAs targeting Firefly luciferase (control), Nudt21 or Sumo2. Shown is quantification of AP+ transgene-independent colonies after 3-10 days of dox exposure, followed by at least 4 days of dox withdrawal. FIG. 2J, Expression levels of epigenetic regulators (Dnmt3b, Tet1) and pluripotency-associated genes (EpCAM, Cdh1, Sall4) in indicated samples at day 6 of OKSM expression or in established iPSCs.

FIG. 3 demonstrates the effect of Nudt21 and Sumo2 suppression on defined reprogramming intermediates. FIG. 3A, Overview of surface markers and reporter alleles used to distinguish between early, mid and late stages of reprogramming. FIG. 3B, Flow cytometry analysis of indicated markers (SSEA1, EpCAM and Oct4-GFP) at intermediate stages of reprogramming in the presence of shRNAs targeting Firefly luciferase, Sumo2 or Nudt21. Note that tRFP expression identifies lentivirally transduced cells. FIG. 3C, Quantification of data shown in FIG. 3B using 3 independent replicates. FIG. 3D, AP+ transgene-independent iPSC colonies obtained upon transfection of reprogrammable MEFs with siRNAs targeting Renilla control, Sumo2 or Nudt21 either once (day 0) or twice (day 0 and day 3) in the presence of dox for 6 days; iPSC colonies were scored after 4 days of dox withdrawal to capture stable iPSC. FIG. 3E, Quantification of data shown in FIG. 3D.

FIG. 4 demonstrates that Nudt21 and Sumo2 suppression act independently of c-Myc expression and in parallel with small molecule enhancers of reprogramming. FIG. 4A, Scheme depicting 3-factor reprogrammable MEFs carrying Col1a1-tetOP-OKS-mCherry and Rosa26-M2rtTA alleles to assess effect of c-Myc expression on iPSC formation. FIG. 4B, Generation of AP+ transgene-independent iPSC colonies obtained from 3-factor reprogrammable MEF transfected with shRNAs targeting Renilla control, Nudt21 or Sumo2 after exposure to dox and small molecules for 9 days; data generated from 3 independent replicates. FIG. 4C, Quantification of data shown in FIG. 4B, dox only samples as well as additional time points. FIG. 4D, Oct4-GFP expression of 3-factor reprogrammable MEFs treated with indicated siRNAs and dox for 9 days, followed by 5 days of dox-independent growth. Note that no Oct4-GFP+ iPSCs could be recovered at this time point without Sumo2 or Nudt21 suppression. FIG. 4E, Comparison of iPSC formation efficiencies from reprogrammable (4-factor) MEFs in the presence of either small molecules or siRNAs targeting Sumo2 and Nudt21. Note the strong effect of Sumo2 or Nudt21 suppression relative to well-characterized small molecules on iPSC formation efficiencies. FIG. 4F, Combination treatment of reprogrammable MEFs with siRNA targeting Sumo2 or Nudt21 and indicated small molecule enhancers of iPSC generation. Note the additive effect of Sumo2 or Nudt21 suppression and small molecule treatment on reprogramming efficiencies.

FIGS. 5A-5F. FIG. 5 demonstrates Generation of iPSCs after as little as 36-48 hours of OKSM expression. FIG. 5A, Treatment with ascorbate (AA), Dotl1 inhibitor (Dotl1i) and Gsk3b inhibitor (Gsk3bi) facilitates the recovery of transgene-independent AP+ iPSC colonies from control and Sumo2 or Nudt21 siRNA transfected MEFs after 72 hours of OKSM expression. FIG. 5B, Quantification of data shown in FIG. 5A using three independent replicates. FIG. 5C, Suppression of Sumo2 enables generation of Oct4-GFP+ transgene-independent iPSCs after 38 hours of OKSM expression whereas suppression of Nudt21 facilitates generation of iPSCs after 48 hours of OKSM expression in the presence of small molecules. FIG. 5D, Expression of endogenous Oct4, Nanog and Sox2 by immunofluorescence in iPSCs generated after Sumo2 suppression and OKSM expression for 38 hours. FIG. 5E, iPSCs shown in FIG. 5C are pluripotent as determined by their potential to differentiate into all three germlayers in teratomas. FIG. 5F, iPSCs produced with Sumo2 siRNAs and small molecules following 38 hours of OKSM expression give rise to coat color chimeras.

FIG. 6 schematically shows the workflow to obtain experimental and control samples for deep sequencing during initial serial shRNA screens.

FIG. 7 shows the results of experiments providing confirmation of reprogramming phenotype with independent shRNAs targeting Sumo2 (left panel) or Nudt21 (right panel). Shown are iPSC formation efficiencies after infecting reprogrammable MEFs with additional shRNAs targeting different seed sequences within Sumo2 and Nudt21 mRNAs. iPSC colonies were determined after 10 days of dox treatment.

FIG. 8 shows that shRNAs against Nudt21 and Sumo2 reduce transcript levels of their respective target mRNAs. qPCR analysis for Nudt21 or Sumo2 transcripts normalized to Gapdh levels.

FIG. 9 shows that Sumo2 or Nudt21 knockdown do not affect cell proliferation or viability. FIG. 9A, Growth curve of reprogrammable MEFs expressing shRNAs against Firefly, Nudt21 or Sumo2 in the presence or absence of dox (i.e., OKSM expression). Cell counts were normalized to the cell number at day 1 (data obtained from 3 replicates). FIG. 9B, Parallel cultures as shown in FIG. 10A were stained for Annexin V (apoptosing cells) and DAPI (dead cells) (data obtained from 3 replicates).

FIG. 10 shows the schematic approach and results using arrayed and multiplexed shRNAmir screening strategies to identify suppressors of reprogramming. FIG. 10A, Arrayed screen design using a combination of retroviral GFP shRNAmir (pLMN) chromatin library (n=247 genes) and Col1A1-OKSM; Rosa26-M2rtTA double transgenic reprogrammable MEFs. Effects of individual shRNAs were tested by counting number of alkaline phosphatase-positive (AP+), doxycycline (dox) independent iPSCs. FIG. 10B, Compilation of arrayed screen results showing average reprogramming efficiency ratios of two biological replicates normalized to *Renilla* shRNA control.

FIG. 11 shows that CAF-1 suppression accelerates reprogramming and yields developmentally competent iPSCs. FIG. 11A, Validation of screening result: measurement of Oct4-GFP+ iPSC colonies obtained after knockdown of either Chaf1a, Chaf1b, or both Chaf1a and Chaf1b (pool). FIG. 11B, Expression dynamics of early reprogramming marker Epcam (empty circle, solid line) and late reprogramming marker Oct4-tomato (full circle dotted line) in CAF-1 depleted and control cells after four and six days of OKSM expression. FIG. 11C, Alkaline phosphatase-positive, transgene-independent iPSC colonies obtained at day 10, following four or six days of dox treatment in the presence of indicated Chaf1a or *Renilla* shRNAs and ascorbate.

FIG. 12 demonstrates that reprogramming phenotype depends on optimal CAF-1 and OKSM dose. FIG. 12A, Comparison of reprogramming efficiency upon CAF-1 knockdown when using MEFs heterozygous or homozygous for the Col1a1::tetOP-OKSM and R26-M2rtTA alleles. Shown are alkaline phosphatase-positive, transgene-independent colonies after six days of dox treatment and four days of dox withdrawal. FIG. 12B, Quantification of data shown in FIG. 12A. FIG. 12C, Schematic of Col1a1::tetOP-miR30– Chaf1a knockin allele. FIG. 12D, MEFs carrying the Col1a1::tetOP-miR30-Chaf1a shRNA and R26-M2rtTA alleles were infected with constitutive pHAGE (Ef1a-OKSM) lentiviral expression vector and exposed to either high (2 µg/ml, top row) or low (0.2 µg/ml, bottom row) doses of dox for indicated time windows before scoring iPSC colonies on day nine by immunostaining for Nanog. FIG. 12E, Quantification of data shown in FIG. 12D.

FIGS. 13A-13I. FIG. 13 shows that CAF-1 suppression enhances reprogramming in different cell conversion systems. FIG. 13A, Strategy to assess effect of CAF-1 suppression on reprogramming fetal hematopoietic stem and progenitor cells (HSPCs) into iPSCs. FIG. 13B, Flow cytometric analysis for Pecam expression during the reprogramming of HSPCs into iPSCs upon Chaf1a suppression using two independent shRNAs. FIG. 13C, Quantification of flow cytometry data shown in FIG. 13B based on geometric means. FIG. 13D, Schematic of transdifferentiation assay of MEFs into induced neurons (iNs) upon viral Ascl1 expression in the presence of a dox-inducible Chaf1a shRNA allele. FIG. 13E, Representative image of MAP2+ iNs detected after 13 days of transdifferentiation. Scale bars: 100 um. FIG. 13F, Quantification of transdifferentiation efficiency, depicted as average number of MAP2+ iNs per 10 frames for each independent experiment (n=5; values are mean+/-S.D; **, unpaired t-test; p=0.0075). FIG. 13G, Assay outline to study transdifferentiation of pre-B cells into macrophages using an estradiol-inducible C/EBPα allele, in the presence of CAF-1 or control shRNAs. FIG. 13H, Representative histograms (n=2) showing activation of macrophage markers Cd14 (left) and Mac1 (right) in control (empty vector; "Null ctrl") and Chaf1a and Chaf1b knockdown cells after 0, 24 and 48 hours of transdifferentiation (estradiol exposure). FIG. 13I, Differences in Cd14 and Mac1 expression levels between Chaf1a/Chaf1b knockdown samples and empty vector control at 0, 24 and 48 hours of transdifferentiation. Shown are fold-change expression differences between experimental and control samples based on geometric means calculated from histogram plots (n=2 independent viral transductions).

FIG. 14 shows that CAF-1 suppression primes pluripotency loci for transcriptional activation by promoting chromatin accessibility and Sox2 binding at regulatory elements. FIG. 14A, ATAC-Seq analysis of CAF-1 and control cells at day three of reprogramming to measure global chromatin accessibility across ESC-active enhancers (n=14265) and promoters (n=5513). Shown are merged data for Chaf1a.164 and Chaf1a.2120 shRNA infected cells. FIG. 14B, Meta gene analysis of Sox2 ChIP-Seq data across all ESC-active promoters and enhancers at day three of reprogramming. Note that cells infected with the weaker shRNA vector (Chaf1a.2120) exhibit a chromatin state that is in between that of cells infected with the *Renilla* shRNA vector and cells infected with the stronger (Chaf1a.164) shRNA vector. FIG. 14C, Comparison of ATAC-Seq and ChIP-Seq data at the Sall1 super-enhancer. Shaded grey bars highlight enhanced Sox2 binding and concomitant accessible chromatin structure at days three and six of reprogramming upon depletion of CAF-1. Blue tracks depict ATAC-seq signatures of iPSCs and Sox2 binding patterns in ESCs. FIG. 14D, Analysis of H3K9me3-dependent reprogramming-resistant regions (RRRs) as defined by Matoba et al. 45 in CAF-1 depleted and control MEFs (day 0) and reprogramming intermediates (day 3). Left panel: heatmap showing the changes in H3K9me3 enrichment over reprogramming resistant (RRR) regions at day 0 and 3 of control (Ren.713) and Chaf1a shRNA knockdown experiments (Chaf1a.164 and Chaf1a.2120). For each RRR (rows), values reflect the averaged H3K9me3 signal between 5 kb intervals spanning the entire region. Right panel: examples of RRRs where the average H3K9me3 signal significantly decreases between day 0 and 3 in the Chaf1a knockdown cells (p<0.05 for both shRNAs after Benjamin-Hochberg correction). Boxplots show the distributions of H3K9me3 signal values for 5 kb intervals spanning across the RRR in each condition and time point. FIG. 14E, Correlation of ATAC-Seq data with gene expression data during reprogramming time course. Shown are ATAC-seq signals for chromatin regions proximal to genes that become upregulated in CAF-1 knockdown intermediates at day 6 by microarray or RNA-seq analysis. ATAC-Seq data are presented for each time point (day 0, 3 and 6) and genotype (*Renilla* and two independent Chaf1a shRNAs). Note that upregulated genes in CAF-1 KD cells at day 6 already show a more accessible chromatin structure at day 3. FIG. 14F, Model: Suppression of CAF-1 during iPSC formation promotes a more accessible chromatin structure at enhancer elements and increased Sox2 binding to ESC-specific targets upon overexpression of reprogramming factors, giving rise to intermediate cells that are more permissive to undergo cell fate change.

FIG. 15 demonstrates the validation of hits from chromatin-focused shRNA screens. FIG. 15A, RT-PCR analysis to confirm knockdown of Chaf1a and Chaf1b expression with Mir30-based vectors from arrayed screen. FIG. 15B, Western blot analysis to confirm knockdown of CAF-1 complex using the top-scoring MiR30-based shRNAs from arrayed screen.

FIG. 16 shows the results of experiments that confirm CAF-1 levels were suppressed during HSPC reprogramming and transdifferentiation. FIG. 16A, Transgene independence assay during HSPC reprogramming in the presence of CAF-1 or control hairpins. Dox pulses were given for 3 or 6 days and AP+ colonies were scored 5 days post Dox withdrawal. FIG. 16B, RT-qPCR analysis for Chaf1a expression to confirm knockdown at day 3 post dox induction (shRNAmir and Ascl1 expression) (n=3; mean+/− S.D.). FIG. 16C, RT-qPCR analysis for Chaf1a and Chaf1b expression to confirm knockdown in transduced pre-B cells prior to induction of transdifferentiation.

FIG. 17 shows the results of experiments that demonstrate that CAF-1 promotes accessible chromatin structure at enhancer elements. FIG. 17A, Experimental outline and assays (SONO-seq, ATAC-seq, Sox2 ChIP-seq) to dissect effect of CAF-1 suppression on chromatin accessibility and transcription factor binding, performed at days 3 and 6 of reprogramming as well as in established iPSCs. FIG. 17B, Metagene analysis for ESC-specific promoters and enhancers using ATAC-seq profiles at day 3 of reprogramming. FIG. 17C, Genome snap shots of representative ATAC-seq accessibility maps at super-enhancer elements (close to Sox2 and Sall4 loci). Shaded grey bars highlight more accessible sites in CAF-1 knockdown samples at days 3 and 6 of reprogramming compared to *Renilla* shRNA controls.

DETAILED DESCRIPTION

Figure 1A:
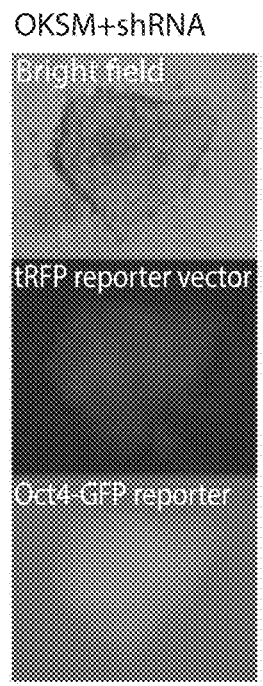
FIGS. 1A-1K.

Provided herein are methods for performing cellular reprogramming that include treatment of somatic cells with an inhibitor of CAF-1, Sumo2, Nutd21, or combinations thereof prior to or during a reprogramming procedure. Such inhibitors can improve both the speed and efficiency of cellular reprogramming. Also described herein are methods in which, rather than reversing cell differentiation, inhibitors of CAF-1 also surprisingly promote differentiation, including transdifferentiation and cancer cell differentiation. Thus, CAF-1 inhibition can also be used in the treatment of cancer.

Definitions

As used herein, the term "cellular reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. The cell to be reprogrammed can be either partially or terminally differentiated prior to reprogramming. In some embodiments, reprogramming encompasses reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). The resulting cells are referred to as "reprogrammed cells;" when the reprogrammed cells are pluripotent, they are referred to as "induced pluripotent stem cells (iPSCs or iPS cells)."

Many varying reprogramming methods are known, and it is reasonable to expect that the removal of the barriers identified herein will permit increased speed and/or efficiency for any such method that re-programs cells. For the avoidance of doubt, the term "cellular reprogramming in the absence of the inhibitor" refers to a comparison of, e.g., reprogramming speed and/or efficiency, between any given reprogramming regimen and that same regimen performed in the presence of an inhibitor of a factor identified herein as a roadblock to reprogramming. Thus, any given reprogramming regimen can serve as the basis for comparison. The same is also true with regard to comparisons for the speed or efficiency of transdifferentiation.

As used herein, the term "speed" when used in reference to cellular reprogramming refers to the appearance of reprogrammed cells at an earlier time point in the presence of an inhibitor or agent as described herein as compared to the emergence of reprogrammed cells in the absence of the inhibitor or agent.

As used herein, the term "earlier time point" means that the emergence of reprogrammed cells in the presence of an inhibitor or agent as described herein occurs at least 6 h earlier, at least 12 h earlier, at least 18 h earlier, at least 24 h earlier, at least 30 h earlier, at least 36 h earlier, at least 4 days earlier, at last 5 days earlier, at least 6 days earlier or more relative to the emergence of reprogrammed cells in the absence of the inhibitor or agent.

As used herein, the term "efficiency of cellular reprogramming" refers to the percentage or number of reprogrammed cells at a given time point. Accordingly, efficiency means that the number of reprogrammed cells in the presence of an inhibitor or agent is increased at least 10%, at least 20%, at least 25%, at least 30%, at least 40%, at least 50%, at least 60%, at least 70%, at least 75%, at least 80%, at least 90%, at least 95%, or even 99% compared to the number of reprogrammed cells generated in the absence of the inhibitor or agent. In some embodiments, the number of reprogrammed cells produced in the presence of an inhibitor or agent is increased by at least 1-fold, at least 2-fold, at least 5-fold, at least 10-fold, at least 20-fold, at least 50-fold, at least 100-fold, or more compared to the number of reprogrammed cells produced in the absence of the inhibitor or agent.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), and Current Protocols in Protein Science (CPPS), John E. Coligan (ed.), John Wiley and Sons, Inc., 2005 (ISBN 0471142735), the contents of which are all incorporated by reference herein in their entireties.

Cellular Reprogramming

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent. The specific reprogramming approach or method used to generate pluripotent stem cells from somatic cells is not critical to the claimed invention. Thus, any method that re-programs a somatic cell to the pluripotent phenotype would be appropriate for use in the methods described herein. Non-limiting examples of reprogramming approaches are discussed in the following.

Reprogramming methodologies using defined combinations of transcription factors have been described for generating induced pluripotent stem cells. Yamanaka and Takahashi converted mouse somatic cells to ES cell-like cells with expanded developmental potential by the direct transduction of genes encoding Oct4, Sox2, Klf4, and c-Myc (Takahashi and Yamanaka, 2006).

Subsequent studies have shown that human iPS cells can be obtained using similar transduction methods and the transcription factor quartet, OCT4, SOX2, LIN28 and NANOG. The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing combinations of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, l-Myc, n-Myc, Rem2, Tert, and LIN28. In one embodiment, reprogramming using the methods and compositions described herein can comprise introducing one or more of Oct-3/4, a member of the Sox family, a member of the Klf family, and a member of the Myc family to a somatic cell. In one embodiment, the methods and compositions described herein further comprise introducing one or more of each of Oct-4, Sox2, Nanog, c-MYC and Klf4 for reprogramming. In some embodiments, the reprogramming can occur in the absence of forced expression of c-Myc. Methods and factors for reprogramming are reviewed by Theunissen and Jaenisch (2014) Cell-Stem Cell 14:720-734.

As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors. In addition to the protein-based and the RNA-based methods (see e.g., Warren et al., supra), recent evidence indicates somatic cells may be re-programmed by e.g., exposure of the cells to unphysiological stress, e.g., in culture (see e.g., WO2013/163296, which is incorporated herein by reference in its entirety). Methods such as these that do not permanently modify the genome may be preferred for cells to be used for therapeutic purposes, as they are less likely to provoke genomic damage likely to promote, e.g., cancer.

The efficiency of reprogramming (i.e., the number of reprogrammed cells) derived from a population of starting cells can be enhanced by the addition of various small molecules, as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. An agent or combination of agents that enhance the efficiency or rate of induced pluripotent stem cell production can be helpful in any reprogramming situation, but can be particularly advantageous, for example, in the production of patient-specific or disease-specific iPSCs. In addition to the factors disclosed herein, some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering A G, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry. It can also be advantageous in appropriate circumstances to use a reporter construct, e.g., driven by the regulatory elements for a stem cell marker to identify a reprogrammed cell.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Further, cells undergoing reprogramming pass through defined intermediate stages that can be tracked and isolated based on combinations of surface markers and reporter alleles (see e.g., Polo et al. (2012) *Cell* 151:1617-1632; Stadtfeld et al. (2008) *Cell Stem Cell* 2:23-240). Briefly, cells initially downregulate THY1 and then upregulate SSEA1, followed by EPCAM and eventually Oct4 (or PECAM) activation. Only cells that follow this transition in a timely manner will give rise to iPSCs. Thus, one of skill in the art can assess changes in these surface markers and reporter alleles to precisely detect or confirm the process of reprogramming.

Somatic Cells for Reprogramming to iPSCs:

Somatic cells, as that term is used herein, refers to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells. It is contemplated herein that somatic cells from any of these tissues can be reprogrammed while taking advantage of the methods and compositions described herein.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used in the therapeutic treatment of disease, it is desirable, but not required, to use somatic cells isolated from the patient being treated. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index. It is emphasized that such a selectable marker is not required—that is, in some embodiments reprogrammed pluripotent stem cells can be identified on the basis of morphology (see e.g., US2010/0184051).

Transdifferentiation

Transdifferentiation, also known as lineage reprogramming or direct conversion, is a process where cells convert from one differentiated cell type to another without undergoing an intermediate pluripotent state or progenitor cell type. Transdifferentiation has been proposed as an approach for disease modeling, drug discovery, gene therapy and regenerative medicine.

Provided herein are methods for inducing transdifferentiation that include inhibiting or depleting CAF-1. Effects of CAF-1 inhibition treatment on transdifferentiation can be assessed during "fibroblast-to-neuron" or "B-cell to macrophage" transdifferentiation using e.g., defined transcription factors as detailed in the Examples herein. However, the effects of CAF-1 inhibition are expected to be broadly applicable to any cell transdifferentiation, particularly since CAF-1-mediated in chromatin assembly and DNA packaging necessarily occur in all cell types.

Transdifferentiation can be performed with the methods and compositions described herein, using any means known in the art. In one approach, termed the "lineage instructive approach" transcription factors from progenitor cells of the target cell type are transfected into a somatic cell to induce transdifferentiation. One of skill in the art can determine which transcription factors to use by starting with a large pool of factors and narrowing down to a specific target cell type transcription factor, or vice versa.

Another approach to transdifferentiation is the "initial epigenetic activation phase approach," where somatic cells are first transfected with pluripotent reprogramming factors temporarily (Oct4, Sox2, Nanog, etc.) before being transfected with the desired inhibitory or activating factors.

Transdifferentiation can also be induced using pharmacological agents, particularly demethylating agents such as 5-azacytidine, or 5-aza-2-deoxycytidine, zebularine, procaine, epigallocatechin-3-gallate, RG108, 1-β-D-arabinofuranosyl-5-azacytosine, dihydro-5-azacytidine or L-ethionine. 5-azacytidine has been shown to promote phenotypic transdifferentiation of cardiac cells to skeletal myoblasts. In some embodiments, growth factors can be included during transdifferentiation, Exemplary growth factors include granulocyte-macrophage stimulating factor (GM-CSF), stem cell factor (SCF), G-CSF, M-CSF, thrombopoietin, IL-2, IL-4, fibroblast growth factor (FGF), epidermal growth factor (EGF) and/or vascular endothelial growth factor. In some embodiments, more than one growth factor will be included.

Further examples of methods for transdifferentiation can be found in e.g., Vierbuchen and Wernig (2012) *Molecular Cell* 47:827-838.

Successful transdifferentiation can be determined using the presence or the absence of the expression of a marker that is specific to a target cell as an indicator. The expression of such marker can be detected by biochemical or immunochemical techniques known by persons skilled in the art. For example, immunochemical techniques such as enzyme-linked immunosorbent assay (ELISA), immunofluorescent assay (IFA), immunoelectrophoresis, immunochromatography assay, and immunohistochemical staining method can be used. In these methods, marker-specific polyclonal or monoclonal antibodies or fragments thereof, which selectively bind to antigens of various target cells, are used. Antibodies against various specific markers are marketed and can be properly obtained by persons skilled in the art. The expression of a marker that is specific to a target cell can also be detected by a molecular biological method such as RT-PCR, transcription mediated amplification (TMA), reverse transcriptase-ligase chain reaction (RT-LCR), or hybridization analysis. Alternatively, the expression of such marker can also be specifically detected by a tissue staining technique such as alizarin red staining, alcian blue staining, Oil-Red-O staining, Von Kossa staining, or indocyanine green staining using metabolic products of differentiated cells, cellular drug metabolism, or properties such as dyeing properties (e.g., a dye exclusion assay).

CAF-1 Complex

DNA is packaged into chromatin, in part to control gene expression. In order for DNA replication to occur, chromatin is disassembled and nucleosomes are transiently removed from the DNA strand. Nucleosomes quickly reassemble behind the DNA replication fork to re-package the DNA. New nucleosomes are generated at the replication fork in a reaction catalyzed by chromatin assembly factor 1 (CAF-1;

NCBI Gene ID: 41836). CAF-1 consists of three polypeptides with molecular weights of 150 (i.e., Chaf1a; NCBI Gene ID: 10036), 60 (i.e., Chaf1b; NCBI Gene ID: 8208), and 48 kDa that bind histones H3 and H4. Inhibition of the expression or activity of any or all of these subunits or an inhibitor that targets the complex (or subunits thereof) can be employed in the methods and compositions disclosed herein.

CAF-1 is also thought to play a role in depositing the histone tetramer onto replicating DNA. In addition, CAF-1 has been associated with the restoration of chromatin structure after DNA repair, and with the maintenance of heterochromatin.

Sumo2

Small ubiquitin-like modifier (Sumo) proteins are a group of small proteins that bind lysine residues of target proteins and thereby modify target protein activity, stability, and sub-cellular localization. There are several different Sumo isoforms, including Sumo1, Sumo2 (NCBI Gene ID: 6613), and Sumo 3. Sumo2 and Sumo3 proteins share a high degree of similarity (95% sequence identity), but are relatively distinct from Sumo1 (only 50% sequence identity). Like ubiquitin, the Sumo protein is synthesized as a larger precursor protein that is processed by sentrin-specific proteases to expose the two C-terminal glycine residues that provide for conjugation. Sumo conjugation (or "sumoylation") is a highly volatile process, with various enzymes involved in the conjugation, e.g., E1, E2 and Ubc9, and de-conjugating (or "de-sumoylation") e.g., SENPs, processes. A number of known Sumo conjugation targets transcription factors and other nuclear proteins involved in gene expression. A major change in levels of Sumo conjugated proteins may have a major impact on the fate of cells.

Nutd21

The Nudix (nucleoside diphosphate linked moiety X)-type motif 21 gene (NCBI Gene ID: 11051) encodes the protein "cleavage and polyadenylation specificity factor subunit 5." The gene product is one subunit of a cleavage factor required for 3' RNA cleavage and polyadenylation processing. Interaction of the protein with RNA is one of the earliest steps in the assembly of the 3' end processing complex and facilitates the recruitment of other processing factors. This gene encodes the 25 kD subunit of the protein complex, which is composed of four polypeptides.

Inhibitors of CAF-1, Sumo2 and Nutd21

Essentially any inhibitor of CAF-1, Sumo2, and/or Nutd21 can be used with the methods and treatments described herein. An inhibitor can be an RNA interference agent (e.g., shRNA, siRNA), an antibody or antigen binding agent, a small molecule, etc. One of skill in the art can readily identify inhibitors of CAF-1, Sumo2, and/or Nutd21 using cellular screening assays that are routine in the art.

As used herein, the term "inhibitor of the CAF-1 complex, Sumo2 or Nutd1" refers to a molecule or agent that significantly blocks, inhibits, reduces, or interferes with the CAF-1 complex, Sumo2, or Nutd1 biological activity in vitro, in situ, and/or in vivo, including activity of downstream pathways mediated by CAF-1, Sumo2, or Nutd1 signaling, such as, for example, RNA or protein upregulation, and/or elicitation of a cellular response to CAF-1, Sumo2, or Nutd1. Exemplary inhibitors contemplated for use in the various aspects and embodiments described herein include, but are not limited to, antibodies or antigen-binding fragments thereof that specifically bind to one or more members of the CAF-1 complex, Sumo2, Nutd1 or their isoforms; anti-sense molecules directed to a nucleic acid encoding one of the targets; short interfering RNA ("siRNA") molecules directed to a nucleic acid encoding a member of the CAF-1 complex, Sumo2, or Nutd21; an inhibitory compound; RNA or DNA aptamers that bind one or more members of the CAF-1 complex, Sumo2, Nutd1 or their isoforms, and inhibit/reduce/block activity or signaling; inhibitory soluble CAF-1, Sumo2, or Nutd21 proteins or fusion polypeptides thereof (e.g., dominant negative mutants).

As used herein, an inhibitor or antagonist has the ability to reduce the activity and/or expression of the CAF-1 complex, Sumo2, or Nutd21 in a cell by at least 5%, at least 10%, at least 20%, at least 30%, at least 40%, at least 50%, at least 60%, at least 70%, at least 80%, at least 90%, at least 95%, at least 98%, at least 99%, or more, relative to the activity or expression level in the absence of the inhibitor or antagonist. At a minimum, an inhibitor will interfere with the inhibitory effect of these factors in a reprogramming assay as described in the Examples—that is, an inhibitor will increase the speed or efficiency of reprogramming in an assay as described herein. In some embodiments, the activity or expression of the CAF-1complex can be assessed using a commercial ELISA kit (e.g., from LIFESPAN BIOSCIENCES) or as described in Verreault et al. (1996) 87(1):95-104. In some embodiments, the activity or expression of Sumo2 can be assessed using a commercial Sumoylation assay kit, for example, Sumo2-FP (UBIQ™), or SUMOylation assay kit (ABCAM™). In some embodiments, the activity of expression of Nutd21 can be assessed using Real-Time PCR primers from e.g., BIORAD, TAQMAN, etc.

In some embodiments, particularly with regard to inhibition of the CAF-1 complex, it is not desirable to inhibit the target completely. One of skill in the art can readily determine or titrate a dose of the inhibitor to achieve a desired result to be used in combination with a cellular reprogramming protocol or for administration to a subject.

RNA Interference Agents:

The use of RNA interference agents is well within the abilities of one of skill in the art and is not described in detail herein. RNA interference (RNAi) uses e.g., small interfering RNA (siRNA) duplexes that target the messenger RNA encoding the target polypeptide for selective degradation via the RNA-induced silencing complex (RISC). siRNA-dependent post-transcriptional silencing of gene expression involves cleaving the target messenger RNA molecule at a site guided by e.g., the siRNA. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" can comprise a short interfering RNA (siRNA), miRNA, shRNA or other double-stranded RNA molecule that targets a gene of interest. Such agents can be chemically synthesized, produced by in vitro transcription, or produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. Sequences encoding these shRNAs can be contained in plasmids, retroviruses, and lentiviruses and expressed from, for example, the pol III U6 promoter, or another promoter. The target gene or sequence of the RNA interfering agent can be a cellular gene or genomic sequence, e.g. a Chaf1a, Chaf1b, Sumo2, or Nutd21 sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence includes RNA derivatives and analogs that permit RNA-mediated gene silencing. Preferably, one strand of the siRNA is identical to its target. The siRNA preferably targets only one sequence. Each of the RNA interfering agents, such as siRNAs, can be screened for potential off-target effects by, for example, expression profiling. Such methods are known to one skilled in the art. In addition to expression profiling, one can also screen the potential target sequences for similar sequences in the sequence databases to identify potential sequences which may have off-target effects. Therefore, one may initially screen the proposed siRNAs to avoid potential off-target silencing using sequence identity analysis by any known sequence comparison methods, such as BLAST. siRNA sequences can also be chosen to maximize the uptake of the antisense (guide) strand of the siRNA into RISC and thereby maximize the ability of RISC to target an mRNA for degradation. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function.

siRNA sequences to target the CAF-1 complex (e.g., Chaf1a, Chaf1b etc.), Sumo2, Nutd21, can also be obtained commercially from e.g., INVITROGEN™, THERMO SCIENTIFIC™, and ORIGENE™, among others.

Antibodies and Antigen Binding Agents:

Antibodies for binding and/or inhibition of a member of the CAF-1 complex, Sumo2, or Nutd21 suitable for use in practicing the methods described herein are preferably monoclonal, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

It is noted that antibodies are widely perceived to be ineffective for targeting intracellular proteins due to relative difficulty in crossing cellular membranes. However, recent evidence indicates that unmodified antibodies can cross the plasma or cell membrane to bind and inhibit intracellular targets (see e.g., US 2014/0286937; Guo et al. (2011) *Science Translational Medicine* 3:99ra85). As such, antibodies or antibody fragments as known in the art and as described herein can be used to inhibit intracellular factors, including CAF-1 complex, Sumo2 and Nutd21. Examples of antibody fragments encompassed by the terms antibody fragment or antigen-binding fragment include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment, which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv), (x) "diabodies" with two antigen binding sites, comprising a heavy chain variable domain ($V_H$) connected to a light chain variable domain ($V_L$) in the same polypeptide chain, (xi) "linear antibodies" comprising a pair of tandem Fd segments ($V_H$—$C_H1$-$V_H$—$C_H1$) which, together with complementary light chain polypeptides, form a pair of antigen binding region; and modified versions of any of the foregoing (e.g., modified by the covalent attachment of polyalkylene glycol (e.g., polyethylene glycol, polypropylene glycol, polybutylene glycol) or other suitable polymer). Although CAF-1, Sumo2, and Nutd21 are intracellular proteins, it is now accepted that antibody agents can be used to target intracellularly (see e.g., U.S. Pat. No. 8,715,674).

Small Molecule Inhibitors:

In some embodiments of the compositions, methods, and uses described herein, an inhibitor of the CAF-1 complex, Sumo2, or Nutd21 is a small molecule inhibitor, including, but not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da. In some embodiments, an inhibitor comprises a small molecule that binds to a member of the CAF-1 complex, Sumo2, or Nutd21 and inhibits its biological activity.

Combination Treatment:

In some embodiments, inhibitors of the CAF-1 complex, Sumo2, and Nutd21 can be used in combination. For example, inhibitors targeting at least two of the CAF-1 complex, Sumo2, and/or Nutd21 can be used in combination. In other embodiments, inhibitors targeting all three of the CAF-1 complex, Sumo2, and Nutd21 can be used in combination.

Promoting Cancer Cell Differentiation

Germline deletion of CAF-1 in mice results in early embryonic lethality, whereas CAF-1 loss in embryonic stem cells causes cell cycle arrest and apoptosis. In the working examples, CAF-1 is shown to act as a general stabilizer of cell identity during normal development and differentiation, in part by maintaining epigenetic patterns in somatic cells. CAF-1 depletion in several pre-leukemic tumor cell lines, which were generated by viral expression of HoxA9, or HoxB8 in myeloid progenitor cells, triggered differentiation and subsequently growth arrest.

Accordingly, inhibitors of CAF-1 can be used to promote differentiation of a cancer cell in vivo. In other embodiments, a CAF-1 inhibitor is administered to a subject for the treatment of cancer. It is expected that a decrease of CAF-1 expression and/or activity will be effective against any cancer type that involves cancer stem cells. Cancers in general often behave like earlier developmental forms of the tissues from which they originate, such that promotion of differentiation will limit the uncontrolled proliferation that is characteristic of cancer. As such, inhibition of CAF-1 is expected to do so with broad applicability.

Some non-limiting examples of cancer that can be treated with a CAF-1 inhibitor include, but are not limited to, carcinoma, lymphoma, blastoma, sarcoma, and leukemia. Other exemplary cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the carcinoma or sarcoma includes, but is not limited to, carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include but are not limited to papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include but are not limited to, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

In one embodiment of the methods, the subject having the tumor, cancer or malignant condition is undergoing, or has undergone, treatment with a conventional cancer therapy. In some embodiments, the cancer therapy is chemotherapy, radiation therapy, immunotherapy or a combination thereof.

Inhibitors of CAF-1 can be used alone or in combination with other therapies, including chemotherapy, radiation, cancer immunotherapy, or combinations thereof. Such therapies can either directly target a tumor (e.g., by inhibition of a tumor cell protein or killing of highly mitotic cells) or provoke or accentuate an anti-tumor immune response.

Exemplary anti-cancer agents that can be used in combination with a CAF-1 inhibitor include alkylating agents such as thiotepa and CYTOXAN™; cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK. polysaccharide complex (JHS Natural Products™, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb™ Oncology, Princeton, N.J.), ABRAXANE™ Cremophorfree, albumin-engineered nanoparticle formulation of paclitaxel (American Pharmaceutical Partners™, Schaumberg, Ill.), and TAXOTERE™ doxetaxel (Rhone-Poulenc Rorer™, Antony, France); chloranbucil; GEMZAR™, gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX™); lapatinib (Tykerb™); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above. In addition, the methods of treatment can further include the use of radiation.

Dosage and Administration

In some aspects, the methods described herein provide a method for inducing cellular differentiation in vivo or a method for treating cancer in a subject. In one embodiment of this aspect and all other aspects described herein, the cancer is leukemia. In one embodiment, the subject can be a mammal. In another embodiment, the mammal can be a human, although the approach is effective with respect to all mammals. The methods comprise administering to the subject an effective amount of a pharmaceutical composition comprising an inhibitor that binds a member of the CAF-1 complex (e.g., Chaf1a, Chaf1b), or a combination thereof in a pharmaceutically acceptable carrier.

The dosage range for the agent depends upon the potency, and includes amounts large enough to produce the desired effect, e.g., cellular differentiation or treatment of cancer. The dosage should not be so large as to cause unacceptable adverse side effects. Generally, the dosage will vary with the type of inhibitor (e.g., an antibody or fragment, small molecule, siRNA, etc.), and with the age, condition, and sex of the patient. The dosage can be determined by one of skill in the art and can also be adjusted by the individual physician in the event of any complication.

Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in immune response (see "Efficacy Measurement" below). Such effective amounts can be gauged in clinical trials as well as animal studies for a given agent.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., a tumor). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Pharmaceutical Compositions

The present disclosure includes, but is not limited to, therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Efficacy Measurement

The efficacy of a given treatment for a cancer (including, but not limited to, leukemia) can be determined by the skilled clinician. However, a treatment is considered "effective treatment," as the term is used herein, if any one or all of the signs or symptoms of the cancer is/are altered in a beneficial manner, or other clinically accepted symptoms or markers of disease are improved, or ameliorated, e.g., by at least 10% following treatment with an agent that comprises an inhibitor that binds a member of the CAF-1 complex, Sumo2, or Nutd21. Efficacy can also be measured by failure of an individual to worsen as assessed by stabilization of the disease, or the need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the cancer; or (2) relieving the disease, e.g., causing regression of symptoms; and (3) preventing or reducing the likelihood of the development of the disease, or preventing secondary diseases/disorders associated with the cancer (e.g., cancer metastasis).

An effective amount for the treatment of a disease means that amount which, when administered to a mammal in need thereof, is sufficient to result in effective treatment as that term is defined herein, for that disease. Efficacy of an agent can be determined by assessing physical indicators of the disease, such as e.g., pain, tumor size, tumor growth rate, blood cell count, etc.

Kits

Also provided herein are kits for inducing cellular reprogramming. At a minimum, the kit(s) described herein comprise at least one inhibitor of the CAF-1 complex, Sumo2, or Nutd21. In one embodiment, the inhibitor comprises an inhibitor of Chaf1a and/or Chaf1b. The inhibitor can be an RNA interference agent, an antibody or antigen binding agent, a small molecule, an aptamer, an antisense molecule, a dominant negative etc. The kit can comprise a single vial of the inhibitor or can comprise individual aliquots (e.g., a unit dose).

In some embodiments, the kits comprise at least two inhibitors, at least 3, at least 4, at least 5 or more. In some embodiments, the plurality of inhibitors are packaged in separate vials. In other embodiments, the plurality of inhibitors are formulated together as a cocktail.

The kit may also comprise components for inducing cellular reprogramming, such as at least one virus, plasmid or vector comprising a nucleic acid sequence encoding a reprogramming factor (e.g., Oct4, Sox2, Klf4, c-Myc, Lin-28, Nanog, etc.). In some embodiments, the kit comprises one or more agents known to enhance efficiency of reprogramming. In some embodiments, the kit further comprises cell growth media and/or reprogramming media.

In some embodiments, the kit comprises primers for detecting cell surface markers on reprogrammed cells.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time. Instructions for use of the components of the kit is packaged therein.

The present invention may be as defined in any one of the following numbered paragraphs or in any combination of the following numbered paragraphs.

1. A method for performing cellular reprogramming, the method comprising:
   (a) contacting a somatic cell with an inhibitor of the CAF-1 complex, Nudt21, or Sumo2, and
   (b) subjecting the somatic cell to a reprogramming protocol,
thereby reprogramming the somatic cell to an induced pluripotent stem cell (iPSC).

2. The method of paragraph 1, wherein the speed and/or efficiency of cellular reprogramming to iPSCs is increased in the presence of the inhibitor as compared to the speed and/or efficiency of cellular reprogramming performed in the absence of the inhibitor.

3. The method of paragraph 1 or 2, wherein the measure of efficiency of cellular reprogramming comprises an increase in the total number of reprogrammed cells relative to reprogramming in the absence of a the inhibitor.

4. The method of paragraph 1, 2 or 3, wherein the measure of speed of cellular reprogramming comprises the appearance of reprogrammed cells at an earlier time point than occurs when reprogramming in the absence of the inhibitor.

5. The method of any one of paragraphs 1-4, wherein the inhibitor comprises an RNA interference molecule or an antibody.

6. The method of any one of paragraphs 1-5, wherein the RNA interference molecule comprises an siRNA or an shRNA.

7. The method of any one of paragraphs 1-6, wherein step (a) is performed before or during step (b).

8. The method of any one of paragraphs 1-7, wherein the reprogramming of step (b) comprises induction of Oct-4/Klf4/Sox-2/c-Myc (OKSM) expression.

9. The method of any one of paragraphs 1-8, wherein the reprogramming step does not comprise forced expression of c-Myc.

10. The method of any one of paragraphs 1-9, wherein the somatic cell comprises a fibroblast.

11. The method of any one of paragraphs 1-10, wherein the inhibitor of the CAF-1 complex inhibits the Chaf1a and/or Chaf1b subunit of the complex.

12. A method of inducing differentiation of a cancer cell or cancer stem cell in vivo, the method comprising: administering an inhibitor of the CAF-1 complex to a subject having, or suspected of having cancer, thereby inducing differentiation of the cancer cell or cancer stem cell in vivo.

13. The method of paragraph 12, wherein the cancer comprises leukemia.

14. The method of paragraph 12 or 13, wherein the inhibitor comprises an RNA interference molecule or an antibody.

15. The method of paragraph 12, 13, or 14, wherein the RNA interference molecule comprises an siRNA or an shRNA.

16. The method of any one of paragraphs 12-15, wherein the inhibitor inhibits the Chaf1a and/or Chaf1b subunit of the CAF-1 complex.

17. A composition comprising: one or more inhibitors of the CAF-1 complex, Nudt21, or Sumo2 and a pharmaceutically acceptable carrier.

18. The composition of paragraph 17, comprising inhibitors of any two or all of the CAF-1 complex, Nudt21 and Sumo2.

19. A composition for use in cellular reprogramming, the composition comprising an inhibitor of the CAF-1 complex, Nudt21, or Sumo2.

20. The composition for use of paragraph 19, further comprising a pharmaceutically acceptable carrier.

21. The composition for use of paragraph 19 or 20, wherein the inhibitor increases the total number of reprogrammed cells relative to reprogramming in the absence of a the inhibitor.

22. The composition for use of paragraph 19, 20 or 21, wherein the inhibitor promotes the appearance of reprogrammed cells at an earlier time point than occurs when cells are reprogrammed in the absence of the inhibitor.

23. The composition for use of any one of paragraphs 19-22, wherein the inhibitor comprises an RNA interference molecule or an antibody.

24. The composition for use of any one of paragraphs 19-23, wherein the RNA interference molecule comprises an siRNA or an shRNA.

25. The composition for use of any one of paragraphs 19-24, wherein cellular reprogramming comprises induction of Oct-4/Klf4/Sox-2/c-Myc (OKSM) expression.

26. The composition for use of any one of paragraphs 19-25, wherein cellular reprogramming does not comprise forced expression of c-Myc.

27. The composition for use of any one of paragraphs 19-26, wherein cellular reprogramming comprises reprogramming of a fibroblast.

28. The composition for use of any one of paragraphs 19-27, wherein the inhibitor of the CAF-1 complex inhibits the Chaf1a and/or Chaf1b subunit of the complex.

29. Use of an inhibitor of the CAF-1 complex, Nudt21, or Sumo2 for cellular reprogramming.

30. The use of paragraph 29, wherein the inhibitor increases the speed and/or efficiency of cellular reprogramming.

31. The use of paragraph 29 or 30, wherein the inhibitor comprises an RNA interference molecule or an antibody.

32. The use of paragraph 29, 30 or 31, wherein the RNA interference molecule comprises an siRNA or an shRNA.

33. The use of any one of paragraphs 29-32, wherein cellular reprogramming comprises induction of Oct-4/Klf4/Sox-2/c-Myc (OKSM) expression.

34. The use of any one of paragraphs 29-33, wherein cellular reprogramming does not comprise forced expression of c-Myc.

35. The use of any one of paragraphs 29-34, wherein cellular reprogramming comprises reprogramming of a fibroblast.

36. The use of any one of paragraphs 29-35, wherein the inhibitor of the CAF-1 complex inhibits the Chaf1a and/or Chaf1b subunit of the complex.

37. A composition for use in the treatment of cancer, the composition comprising an inhibitor of the CAF-1 complex.

38. The composition for use of paragraph 37, wherein the composition induces the differentiation of a cancer cell or cancer stem cell in vivo when administered to an individual having cancer.

39. The composition for use of paragraph 37 or 38, further comprising a pharmaceutically acceptable carrier.

40. The composition for use of paragraph 37, 38, or 39, wherein the inhibitor comprises an RNA interference molecule or an antibody.

41. The composition for use of any one of paragraphs 37-40, wherein the RNA interference molecule comprises an siRNA or an shRNA.

42. The composition for use of any one of paragraphs 37-41, wherein the cancer comprises a leukemia.

43. The composition for use of any one of paragraphs 37-42, wherein the inhibitor inhibits the Chaf1a and/or Chaf1b subunit of the CAF-1 complex.

44. Use of an inhibitor of the CAF-1 complex for the treatment of cancer, the use comprising administering the inhibitor of the CAF-1 complex to an individual having cancer.

45. The use of paragraph 44, wherein the administering induces the differentiation of a cancer cell or cancer stem cell, thereby treating the cancer.

46. The use of paragraph 44 or 45, wherein the inhibitor comprises an RNA interference molecule or an antibody.

47. The use of paragraph 44, 45, or 46, wherein the RNA interference molecule comprises an siRNA or an shRNA.

48. The use of any one of paragraphs 44-47, wherein the cancer comprises a leukemia.

49. The use of any one of paragraphs 44-48, wherein the inhibitor inhibits the Chaf1a and/or Chaf1b subunit of the CAF-1 complex.

50. A method for performing cellular transdifferentiation, the method comprising: (a) contacting a somatic cell with an inhibitor of the CAF-1 complex, and (b) subjecting the somatic cell to a transdifferentiation protocol, thereby transdifferentiating the somatic cell to a different cell type.

51. The method of paragraph 50, wherein the speed and/or efficiency of cellular transdifferentiation is increased in the presence of the inhibitor as compared to the speed and/or efficiency of cellular reprogramming performed in the absence of the inhibitor.

52. The method of paragraph 50 or 51, wherein the measure of efficiency of cellular transdifferentiation comprises an increase in the total number of transdifferentiated cells relative to transdifferentiation in the absence of a said inhibitor.

53. The method of paragraph 50, 51, or 52, wherein the measure of speed of cellular transdifferentiation comprises the appearance of transdifferentiated cells at an earlier time point than occurs when cells are transdifferentiated in the absence of said inhibitor.

54. The method of any one of paragraphs 50-53, wherein the inhibitor comprises an RNA interference molecule or an antibody.

55. The method of any one of paragraphs 50-54, wherein the RNA interference molecule comprises an siRNA or an shRNA.

56. The method of any one of paragraphs 50-55, wherein step (a) is performed before or during step (b).

57. The method of any one of paragraphs 50-56, wherein the transdifferentiation of step (b) comprises transdifferentiation of a fibroblast to a neuron or transdifferentiation of a B-cell to a macrophage.

58. The method of any one of paragraphs 50-57, wherein transdifferentiation of a fibroblast to a neuron comprises overexpression of the transcription factor Ascl1 in a fibroblast.

59. The method of any one of paragraphs 50-58, wherein transdifferentiation of a B-cell to a macrophage comprises overexpression of the myeloid transcription factor C/EBPα in a B-cell.

60. The method of any one of paragraphs 50-59, wherein the inhibitor of the CAF-1 complex inhibits the Chaf1a and/or Chaf1b subunit of said complex.

EXAMPLES

Example 1: Sumo2 and Nutd21 as Roadblocks to Reprogramming

The goal of this study was to identify novel, potent roadblocks to reprogramming by performing a serial genome-wide shRNA enrichment screen in combination with a well-defined transgenic reprogramming system. Unexpectedly, this screening strategy uncovered two post-transcriptional mechanisms, protein sumoylation and alternative polyadenylation, as strong repressors of iPSC formation.

Serial shRNA Screen for Roadblocks to Reprogramming

Figure 1B:
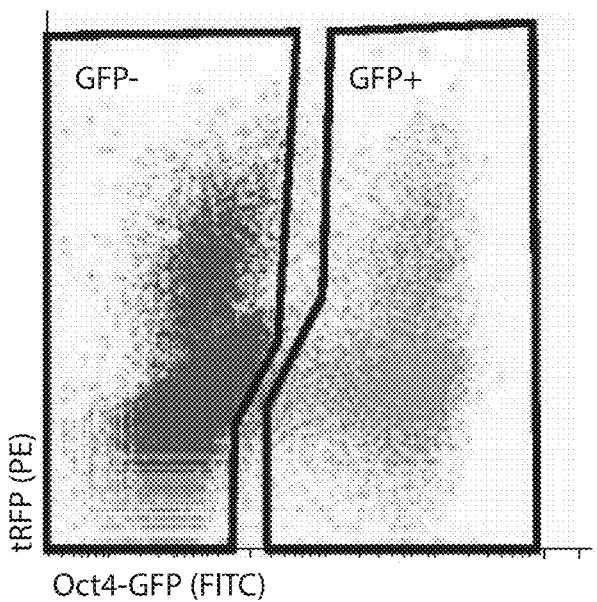

To identify roadblocks to iPSC formation in an unbiased manner, the inventors combined a well-defined transgenic reprogramming system with a genome-wide shRNA library targeting 27,478 genes with 62,877 hairpins. The inventors utilized murine embryonic fibroblasts (MEFs) carrying a doxycycline (dox)-inducible polycistronic cassette encompassing the open reading frames for Oct4, Klf4, Sox2 and c-Myc (OKSM) in the Col1a1 locus, the M2-rtTA transactivator in the Rosa26 locus and an EGFP reporter in the endogenous Pou5f1 (Oct4) locus (Stadtfeld et al., 2010). These transgenic MEFs are referred to herein as "reprogrammable cells" and the genotype as "Col1a1-tetOP-OKSM; R26-M2rtTA; Oct4-GFP". The shRNA library was generated by cloning shRNAs into the pHAGE-Mir lentiviral vector carrying a puromycin resistance gene and an tRFP reporter (Plank et al., 2013). Transduction of reprogrammable MEFs with an identical empty vector gave rise to Oct4-GFP+, tRFP+ iPSC colonies upon exposure to dox, albeit at slightly lower frequencies than uninfected cells (FIGS. 1A, 1B and data not shown), demonstrating the feasibility of a screen to identify roadblocks to iPSC generation using this lentiviral shRNA vector system.

Figure 1C:
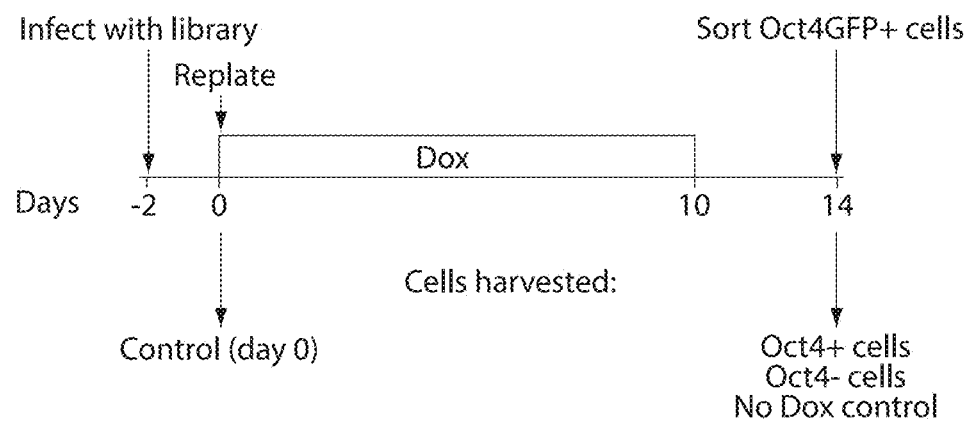
Figure 1D:
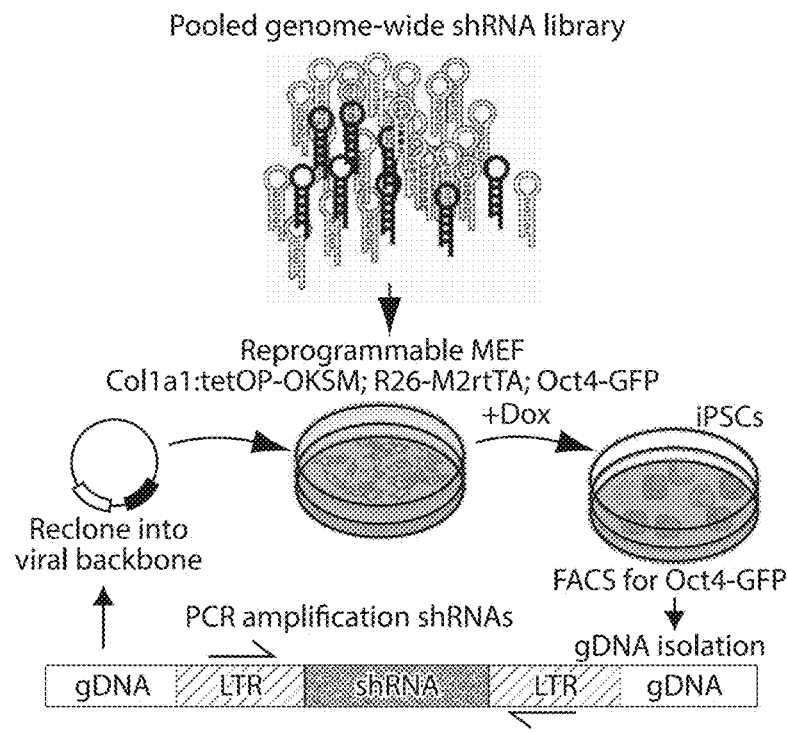
Figure 1E:
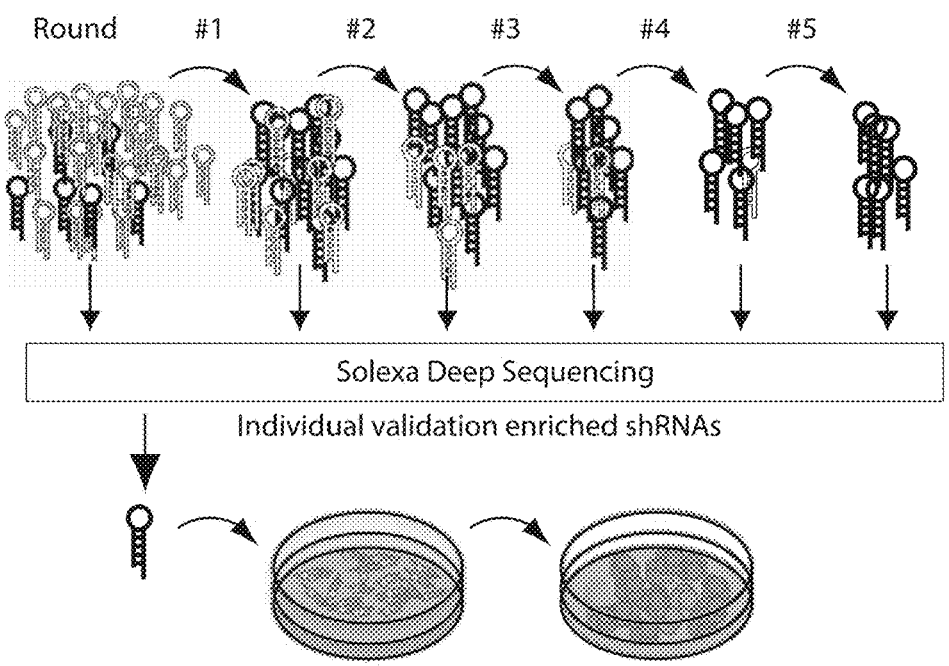
Figure 6:
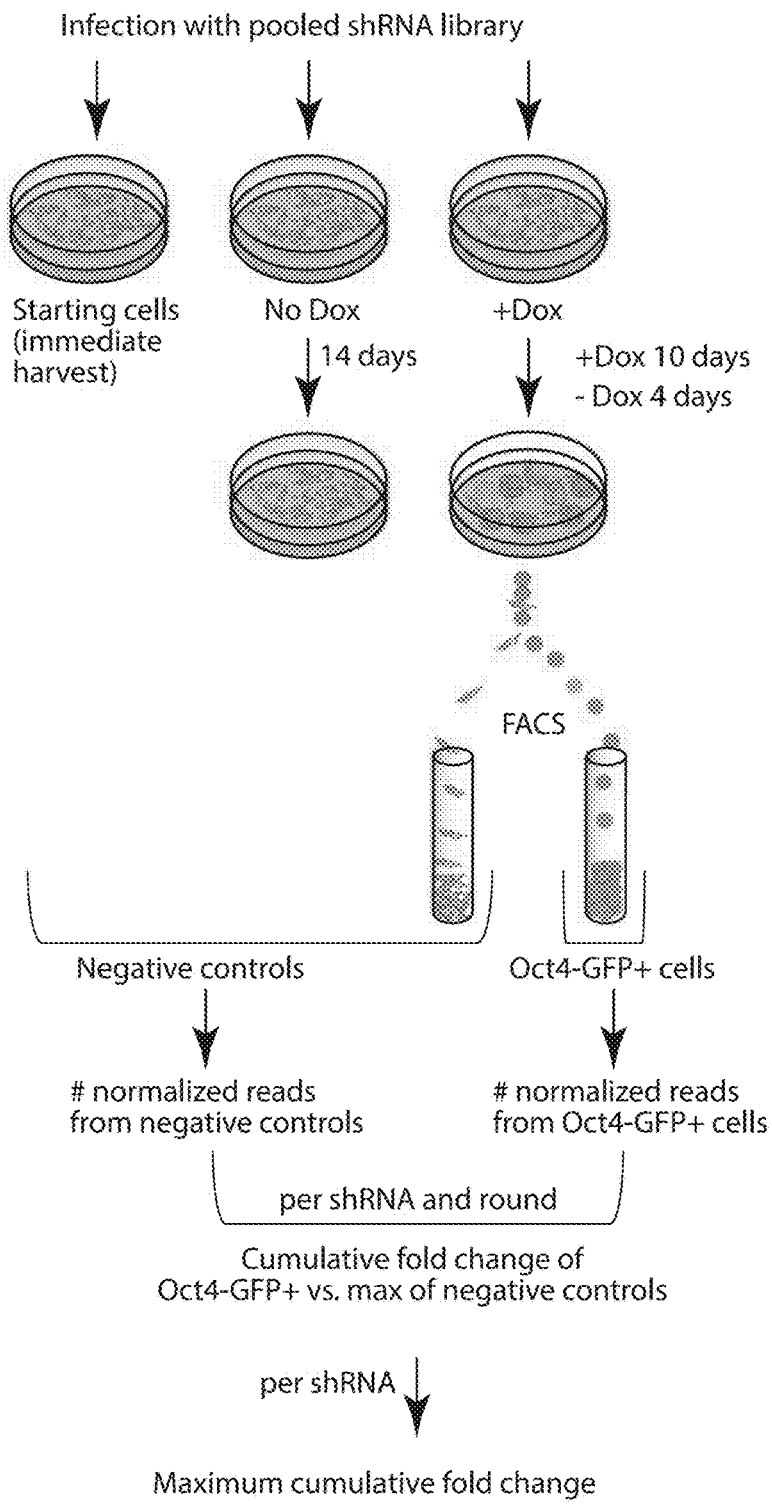
FIG. 6.

To identify shRNAs that potently enhance reprogramming with low background signal from passenger shRNAs, pooled screening strategy using serial enrichment of hairpin libraries was devised. Briefly, the inventors infected reprogrammable MEFs with the pooled shRNA library 2 days before dox induction to ensure effective suppression of targets prior to initiation of reprogramming. After 10 days of OKSM expression, dox was withdrawn for 4 days to select for stably reprogrammed, transgene-independent colonies, followed by purification of emerging Oct4-GFP+ cells by flow cytometry (FIG. 1C). Enriched hairpins were amplified by PCR from genomic DNA and subsequently re-cloned into the original viral backbone before initiating another round of viral transduction and reprogramming (FIG. 1D). In total, between 3 and 5 rounds of shRNA enrichment and iPSC generation were performed (FIG. 1E). Parallel cultures of reprogrammable MEFs were exposed to dox alone or transduced with the viral library in the absence of dox before extracting genomic DNA (FIG. 1C and FIG. 6); these samples served as controls for possible passenger hairpins that became passively enriched in expanding iPSC colonies or hairpins that merely affected the growth of non-induced reprogrammable MEFs. Library representation was determined in all samples by deep (Solexa™) sequencing of genomic DNA. To identify potential hits, the inventors utilized a set of criteria based on absolute shRNA sequence reads and shRNA enrichment scores between experimental and control samples (FIG. 6).

Nudt21 and Sumo2 Emerge as Top Candidate Roadblocks to Reprogramming

Figure 1F:
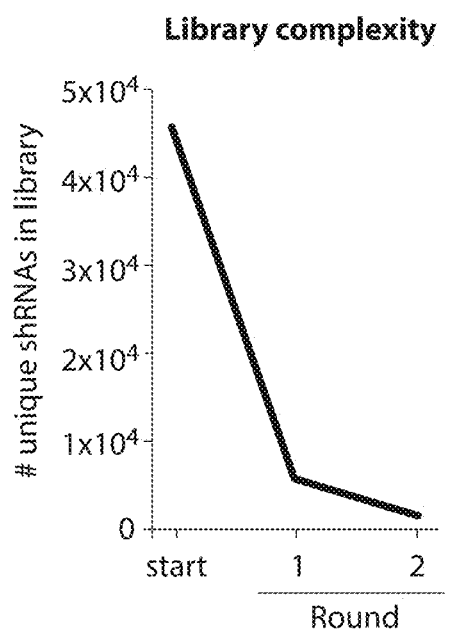
Figure 1G:
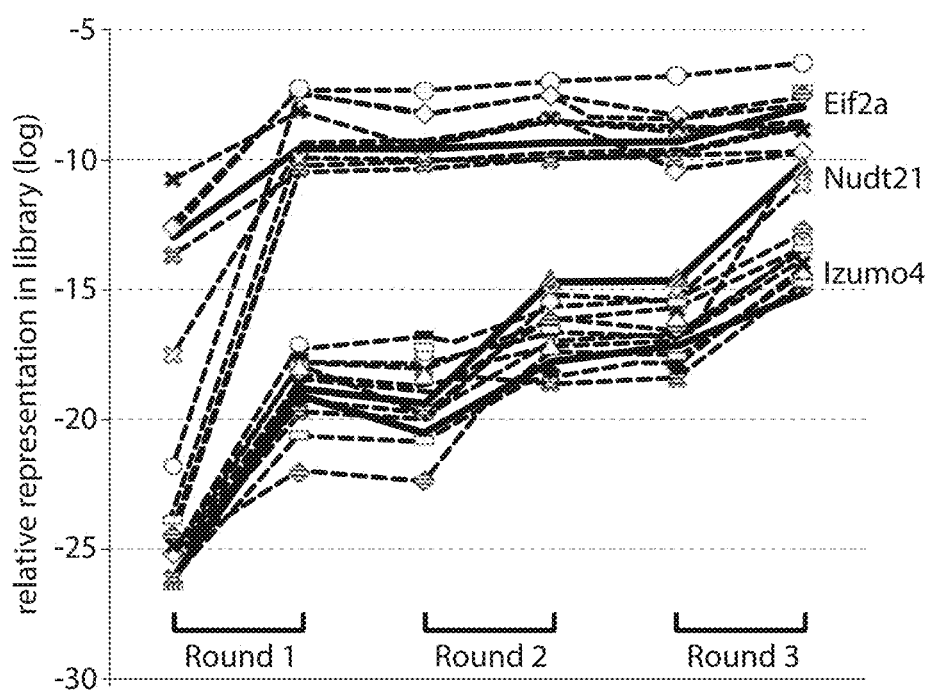
Figure 1H:
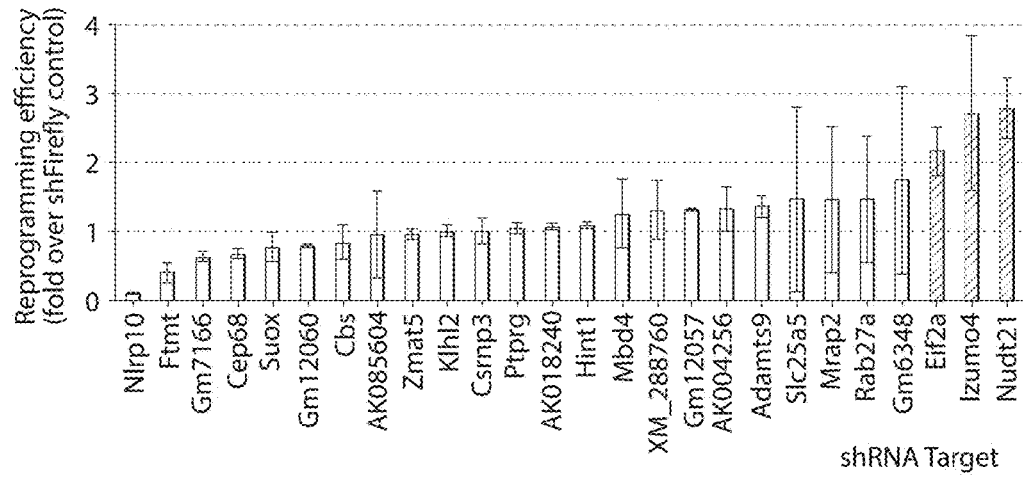

The inventors observed a steep drop in library complexity (i.e., the number of unique shRNAs detected by Solexa™ sequencing) after the first round of reprogramming but a more gradual decline in subsequent rounds (FIG. 1F, left panel). Critically, shRNA libraries prepared from rounds 1-3 enhanced the formation of iPSCs compared to uninfected controls, indicating a progressive enrichment of functional hairpins that promoted reprogramming (FIG. 1F, right panel). The inventors next determined candidate hairpins that may promote reprogramming based on (i) their enrichment across all libraries relative to controls and (ii) absolute shRNA sequence representation per library (FIG. 6). To validate candidates, the inventors recovered multiple top-scoring shRNAs by PCR from enriched shRNA libraries, subcloned hairpins into the pHAGE-Mir vector and infected reprogrammable cells individually with these constructs or a control shRNA vector targeting Firefly luciferase. FIG. 1G depicts the enrichment of 26 selected candidate shRNAs across 3 rounds of screening. Of these shRNAs, 3 hairpins enhanced iPSC formation more than 2-fold (Nudt21, Eif2a, Izumo4) in initial validation experiments with Nudt21 showing the strongest effect (FIG. 1H).

Figure 1I:
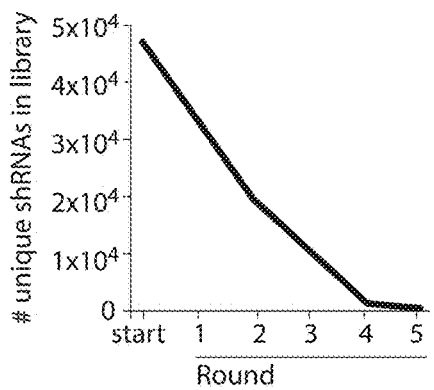
Figure 1J:
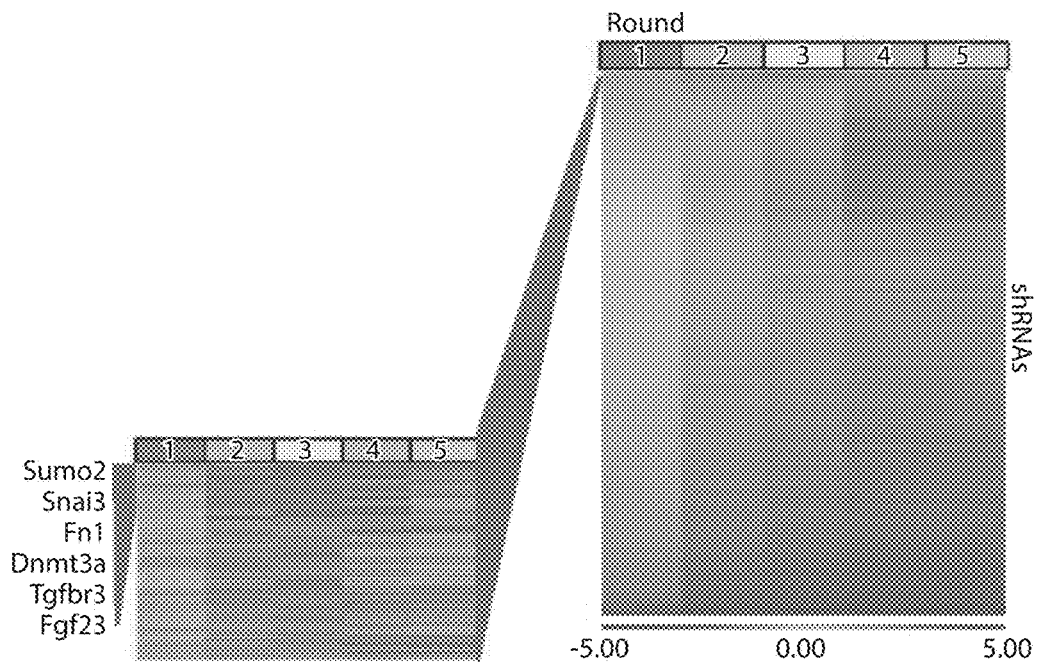
Figure 1K:
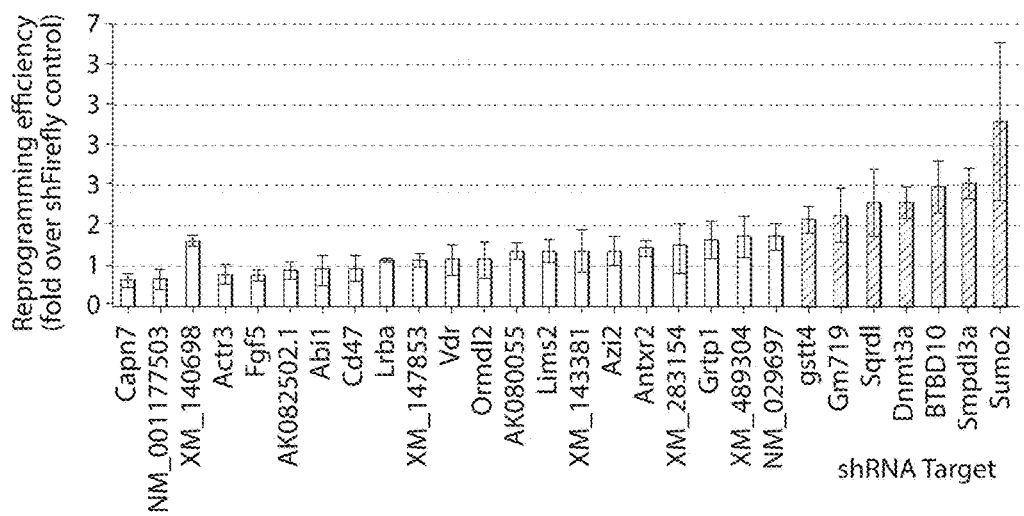

To obtain a better coverage of the library and to minimize the loss of potentially functional hairpins during the first round of reprogramming, the serial screen was repeated with a higher number of starting cells and 2 additional rounds of reprogramming and shRNA enrichment. This modification of the protocol indeed resulted in a more gradual reduction of library complexity after the first round of reprogramming and a concomitant enrichment of hundreds of hairpins that enhanced iPSC formation as a pool (FIG. 1I). Analysis of shRNAs that were consistently enriched across all 5 rounds of reprogramming using two different algorithms revealed several additional candidate barriers to reprogramming such as Fgf5, Dnmt3a, Smpdl3a and Sumo2 (FIG. 1J). Of 27 validated shRNAs, 7 showed a more than 2-fold increase in iPSC formation (Gstt4, Gm719, Sqrd1, Dnmt3a, BTBD10, Smpd3a, Sumo2) (FIG. 1K) with Sumo2 shRNA exhibiting the strongest phenotype. Given the prominent effects on reprogramming of shRNAs targeting Nudt21 from the first screen and Sumo2 from the second screen, the inventors focused on these genes for the remainder of the study.

Nudt21 (nucleoside diphosphate linked moiety X-type motif 21; also termed Cpsf5 or Cfim25) is part of the cleavage factor involved in 3' RNA cleavage and polyadenylation processing (Di Giammartino et al., 2011) while Sumo2 (small ubiquitin-like modifier 2) plays an important role in lysine sumoylation of proteins (Hickey et al., 2012).

Figure 2A:
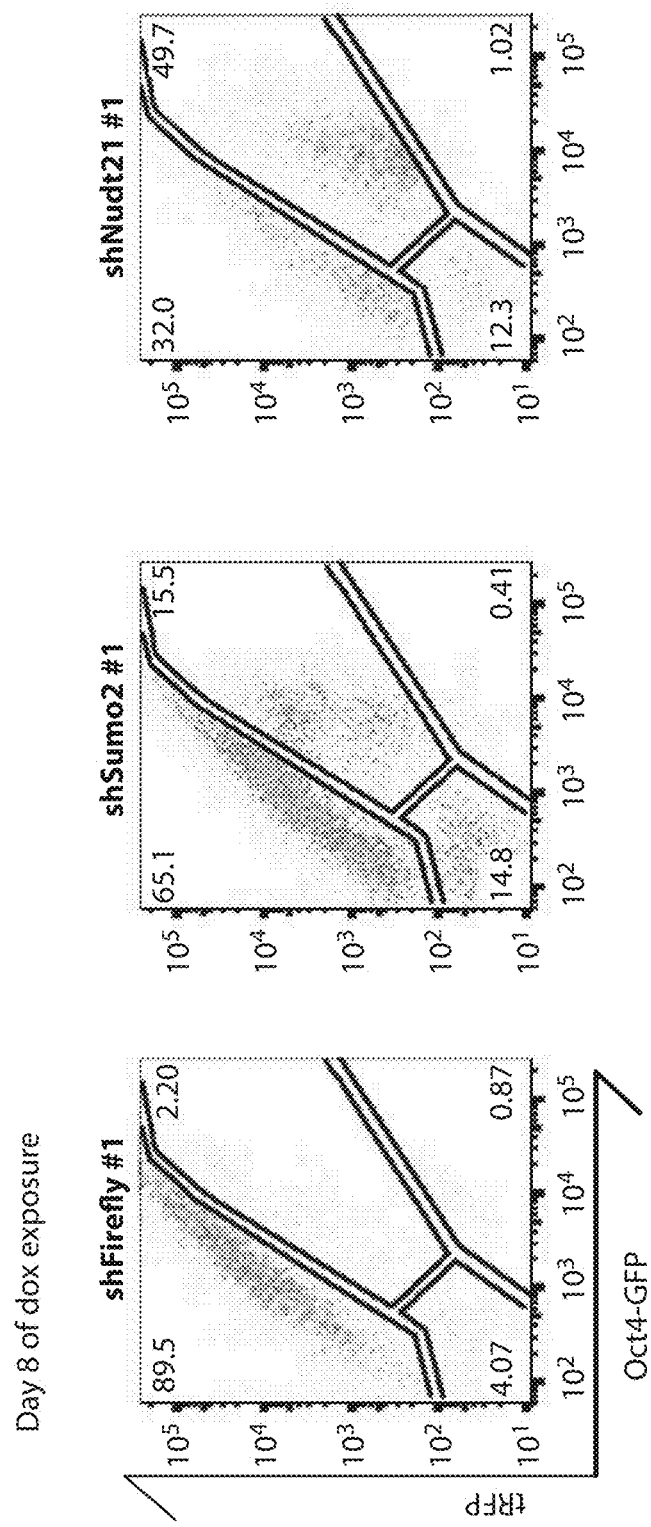
FIGS. 2A-2J.
Figure 2B:
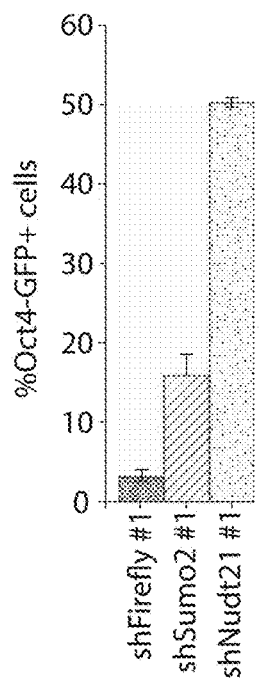
Figure 2C:
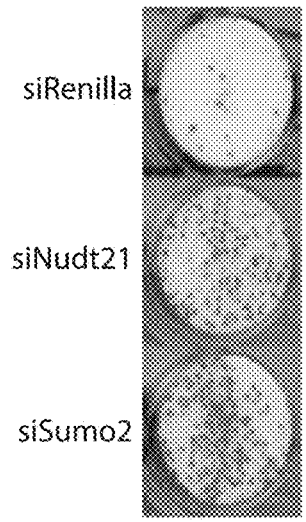
Figure 2D:
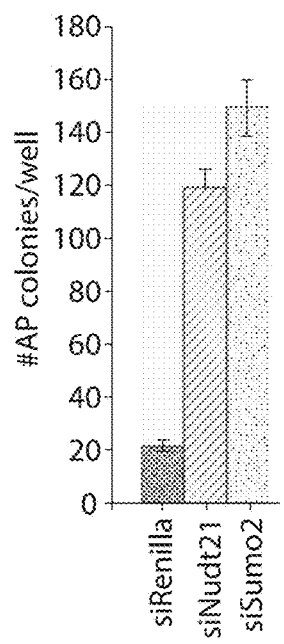
Figure 2E:
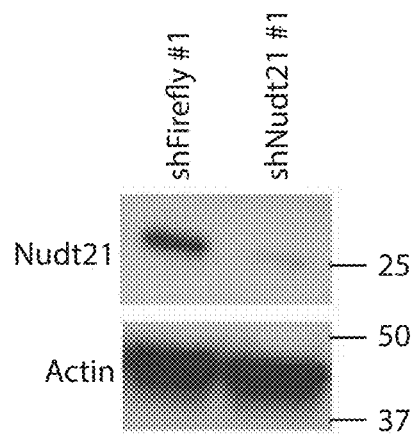
Figure 2F:
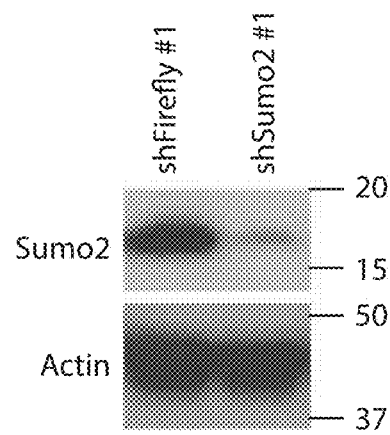
Figure 2G:
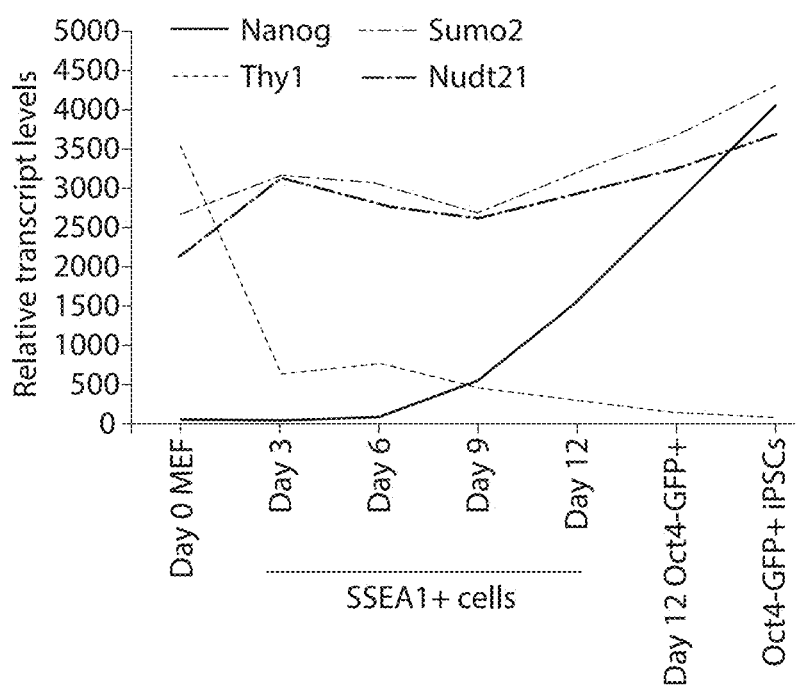
Figure 7:
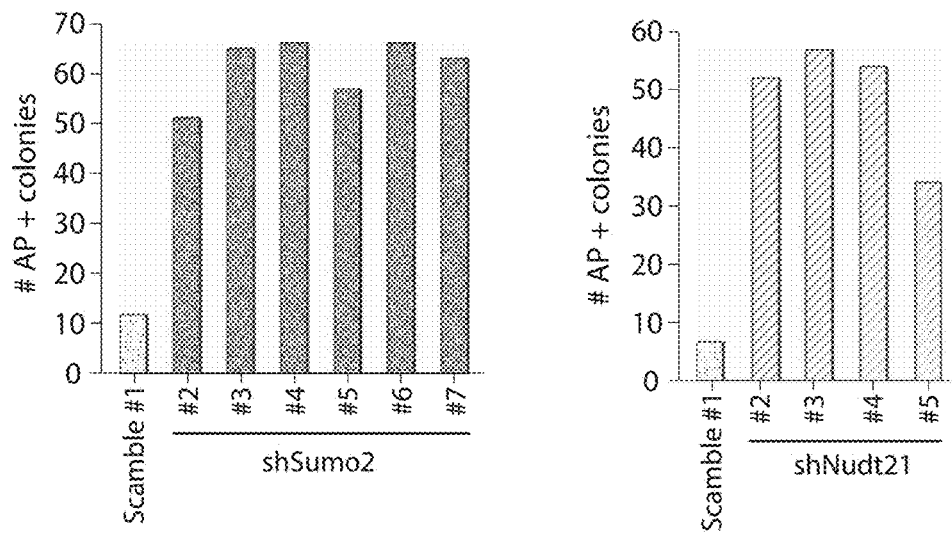
FIG. 7.
Figure 8:
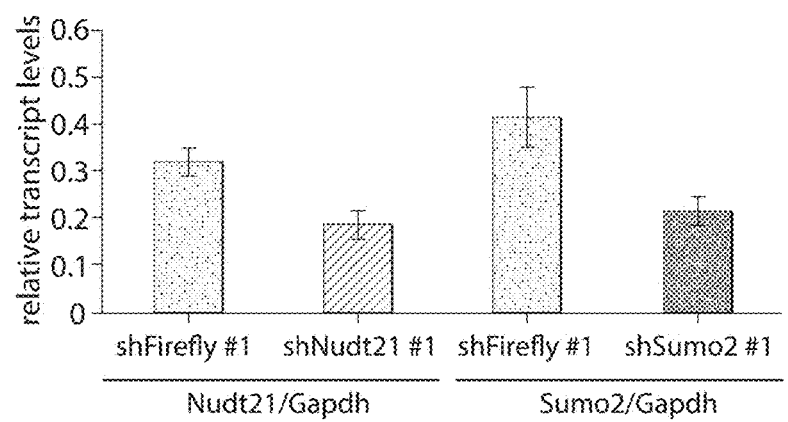
FIG. 8.
Figure 9A:
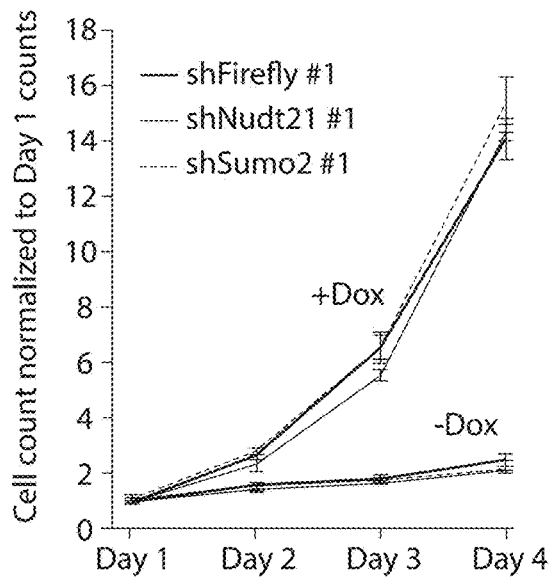
FIGS. 9A-9B.
Figure 9B:
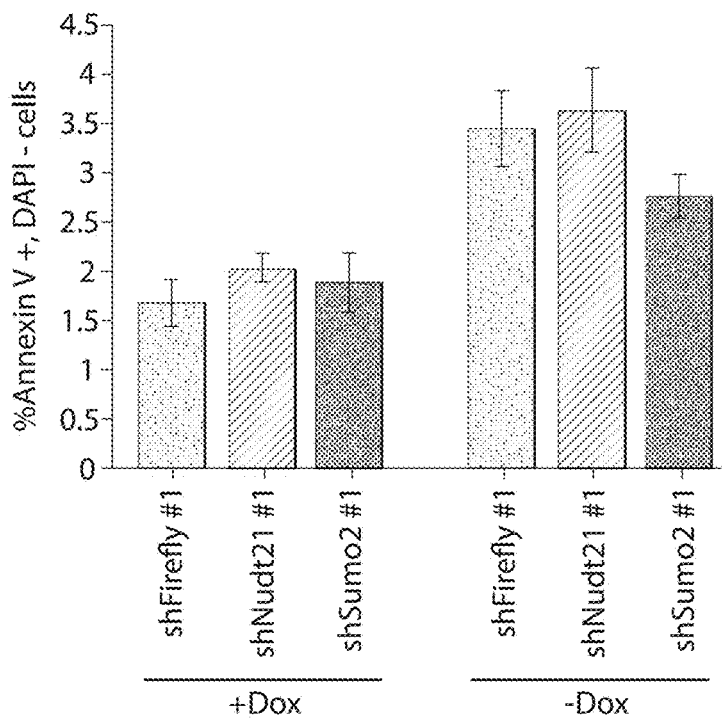

Suppression of Nudt21 or Sumo2 Promotes Pluripotency Gene Activation in Nascent iPSCs without Compromising Growth or Pluripotency Using more quantitative reprogramming assays, the inventors found that suppression of either Sumo2 or Nudt21 increased the number of transgene-independent alkaline phosphatase-positive (AP+) iPSC-like colonies up to 15-fold and the fraction of Oct4-GFP+ cells up to 25-fold (50% with Nudt21 shRNA; 16% with Sumo2 shRNA; 2% with control shRNA at day 8) (FIGS. 2A, 2B). The inventors were able to recapitulate enhanced reprogramming with 4-6 independent shRNAs as well as siRNA pools targeting Nudt21 and Sumo2, documenting the consistency of the observed phenotype using either permanent or transient knockdown approaches. (FIGS. 2C, 2D and FIG. 7). Importantly, suppression of Sumo2 and Nudt21 led to reduced transcript and protein levels of either factor, demonstrating the specificity of knockdown (FIG. 2E, 2F and FIG. 8). Moreover, iPSC generated with these shRNAs could be stably propagated over many passages and gave rise to well-differentiated teratomas, documenting that suppression of Sumo2 or Nudt21 does not compromise the self-renewal or pluripotency of iPSCs. It is noteworthy that endogenous Nudt21 and Sumo2 mRNA levels were comparable between MEFs and iPSCs and barely changed during the reprogramming process, indicating that these factors are important in both somatic and pluripotent cell types (FIG. 2G).

Figure 2H:
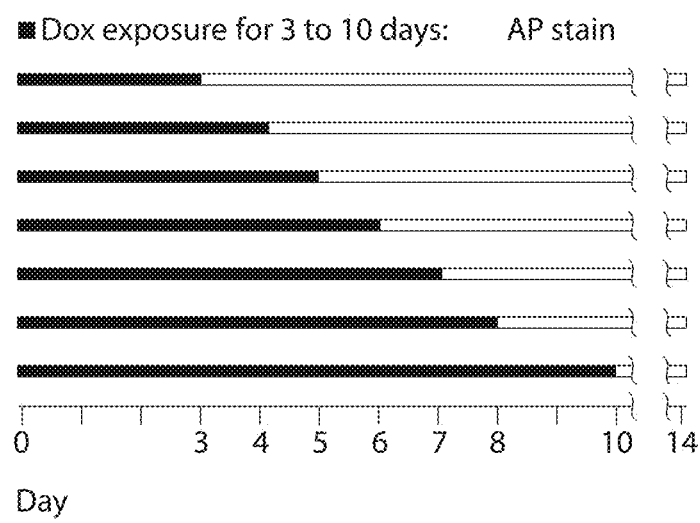
Figure 2I:
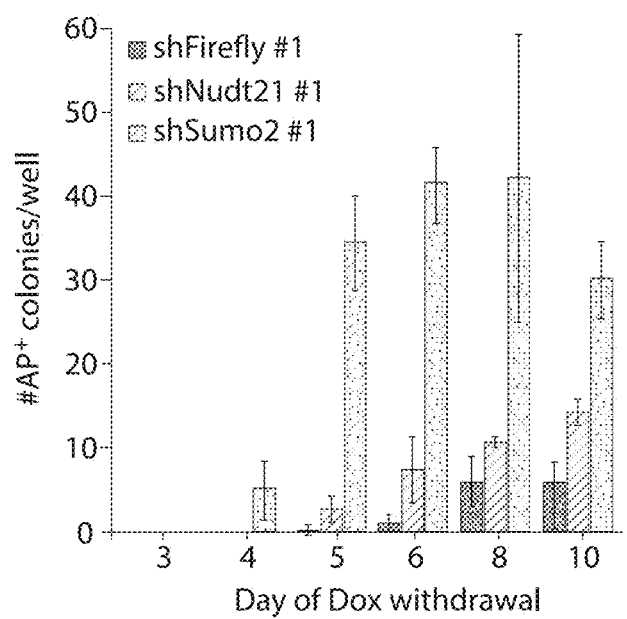
Figure 2J:
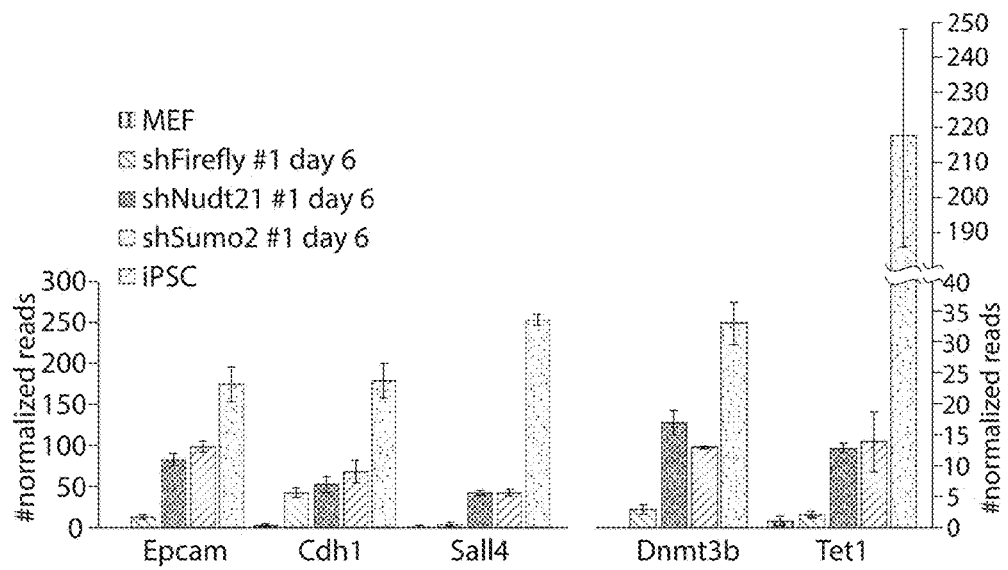

To complement the aforementioned marker-based assays of reprogramming with a functional assay, it was determined whether suppression of Sumo2 or Nudt21 could promote the formation of transgene-independent iPSC colonies after short pulses of OKSM expression (FIG. 2H). Consistent with AP and Oct4-GFP-based assays, it was found that knockdown of either molecule yielded transgene-independent iPSC colonies after only 5 days of OKSM expression, whereas stable iPSC colonies only emerged by day 8 in controls (FIG. 2I). In agreement with this observation, the inventors detected transcriptional upregulation of key ESC-associated genes (e.g., Epcam, Cdh1 and Sall4) and epigenetic regulators (e.g., Dnmt3b and Tet1) exclusively in cells expressing OKSM and either Nudt21 or Sumo2 shRNAs at day 6 of reprogramming (FIG. 2J). Critically, knockdown of neither molecule had a discernible effect on cell proliferation or apoptosis of bulk cultures, thus excluding the possibility that the observed phenotypes are due to accelerated growth or reduced cell death. Together, these results demonstrate that transient or constitutive suppression of Sumo2 and Nudt21 markedly enhances and accelerates the formation of iPSCs from somatic cells.

Nudt21 and Sumo2 Suppression Act During Early-to-Mid Stages of Reprogramming

Figure 3A:
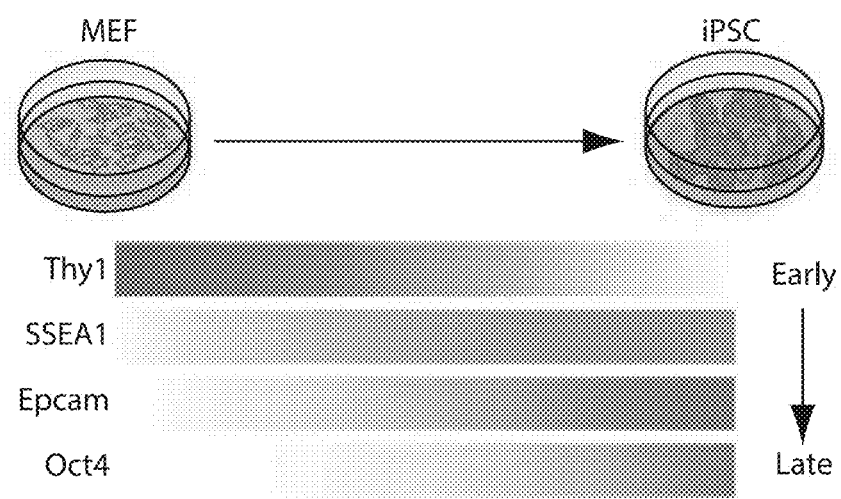
FIGS. 3A-3E.
Figure 3B:
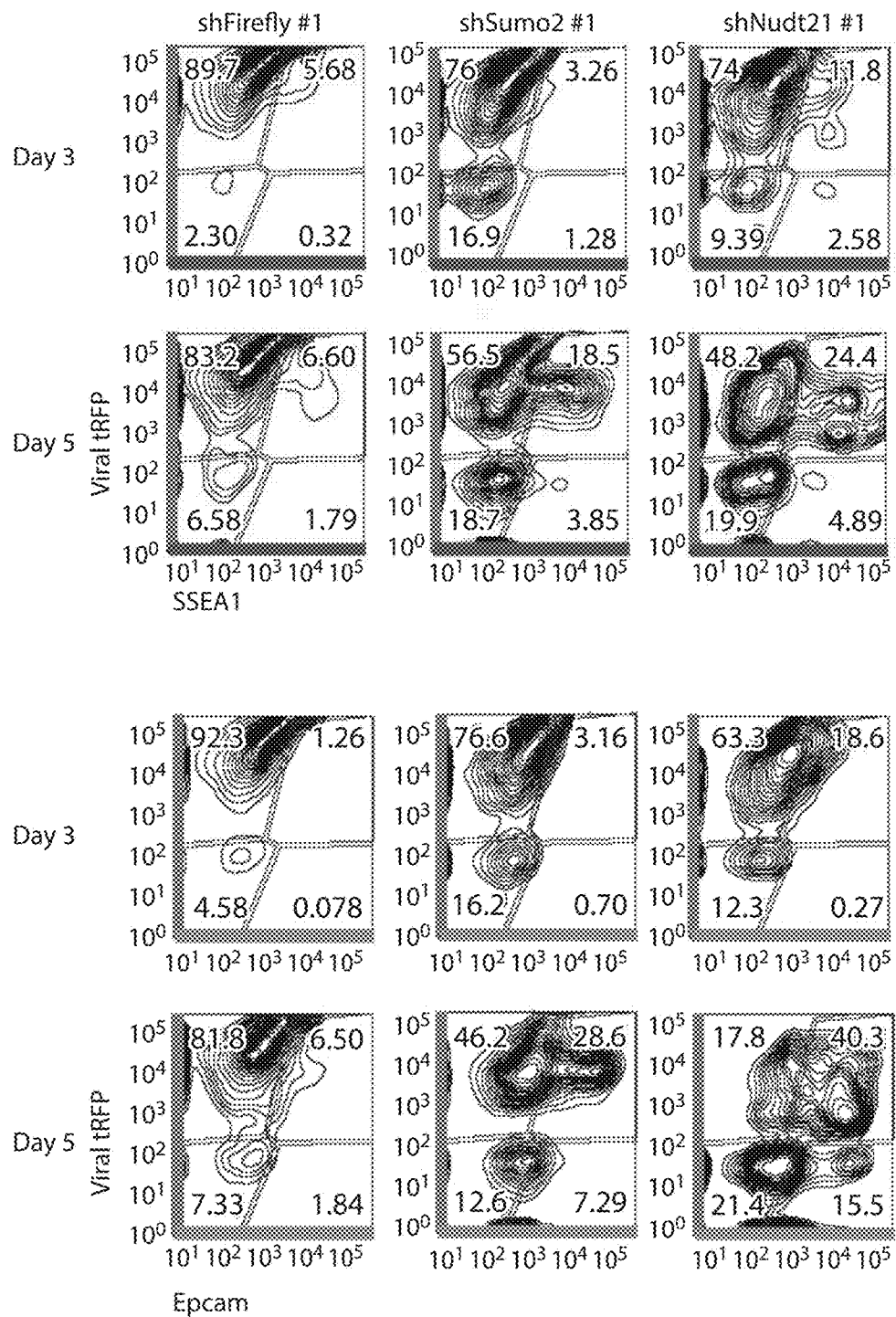
Figure 3B:
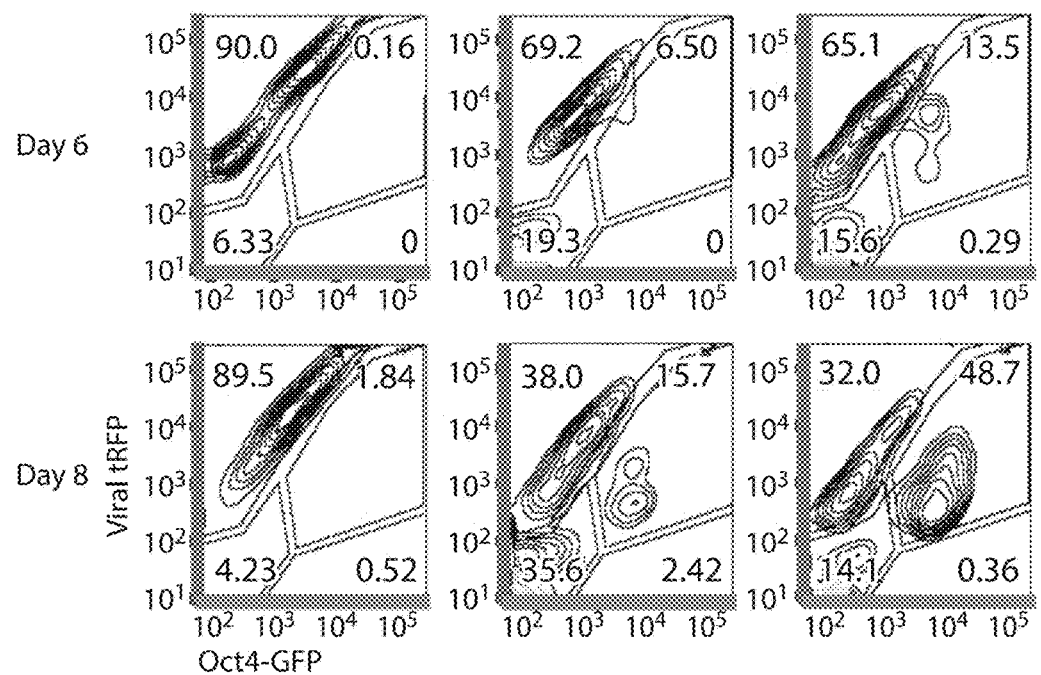
Figure 3C:
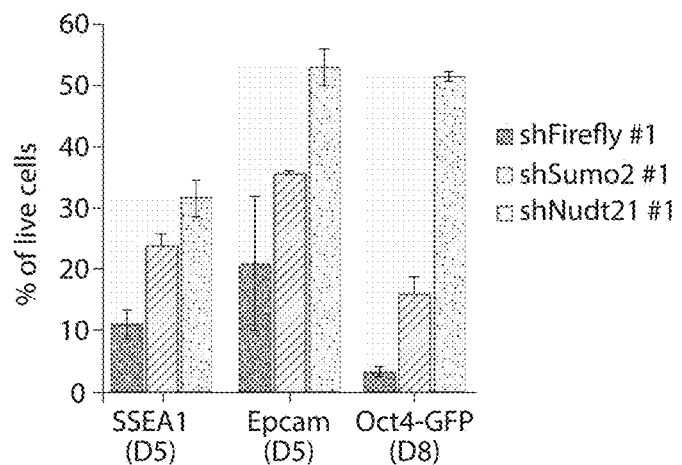

In order to understand how Sumo2 and Nudt21 suppression influences the dynamics of iPSC formation, surface markers and a reporter allele were utilized to distinguish between early, mid and late stages of reprogramming. The inventors previously showed that cells undergoing successful reprogramming initially upregulate SSEA1 (early stage), followed by sequential activation of EpCAM (mid stage) and Oct4-GFP (late stage) (Polo et al., 2012). Remarkably, Nudt21 suppression showed a noticeable increase in the fraction of SSEA1+ and EpCAM+ cells relative to controls as early as day 3 of reprogramming (14% vs. 6% for SSEA1; 19% vs. 1% for EpCAM)(FIGS. 3A, 3B). This trend continued at later stages of iPSC formation when 56% EpCAM+ cells were detectable by day 5 (8% in controls) and 49% Oct4-GFP+ cells by day 8 (2% in controls). In contrast, Sumo2 depletion had no pronounced effects on the earliest intermediates of reprogramming, as shown by comparable fractions of SSEA1+ and EpCAM+ cells at day 3 relative to controls (5% vs. 6% for SSEA1; 4% vs. 1% for EpCAM)(FIG. 3A, 3B). However, the inventors observed a 3-fold increase in the fraction of SSEA1+ cells and a 5-fold increase in the fraction of EpCAM+ cells by day 5 as well as an 8-fold increase in the fraction of Oct4-GFP+ cells by day 8 of reprogramming. A relative comparison of SSEA1+, EpCAM+ and Oct4-GFP+ cells between virally transduced (tRFP+) and untransduced (tRFP−) reprogrammable cells confirmed these observations and further demonstrated that the enhancing effect of Sumo2 and Nudt21 suppression on iPSC generation is cell-autonomous (FIG. 3C).

Figure 3D:
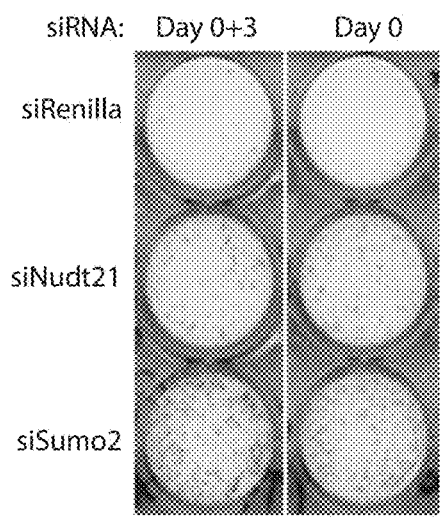
Figure 3E:
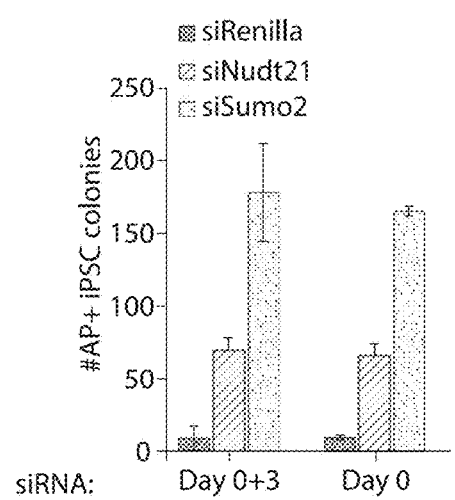

To functionally corroborate the notion that Sumo2 and Nudt21 are required during early-to-mid stages of reprogramming, the inventors determined iPSC colony formation efficiencies after transfecting reprogrammable MEFs with siRNAs against Sumo2 or Nudt21 either once (on day 0) or twice (on day 0 and day 3) (FIGS. 3D, 3E). iPSC colony formation was essentially the same when Sumo2 or Nudt21 were suppressed initially or continuously during a 6-day reprogramming period. Collectively, these phenotypic and functional assays indicate that Nudt21 suppression promotes very early stages while Sumo2 suppression promotes early-to-mid stages of reprogramming, ultimately leading to a dramatic increase in the formation of Oct4+ transgene-independent iPSCs.

Figure 4A:
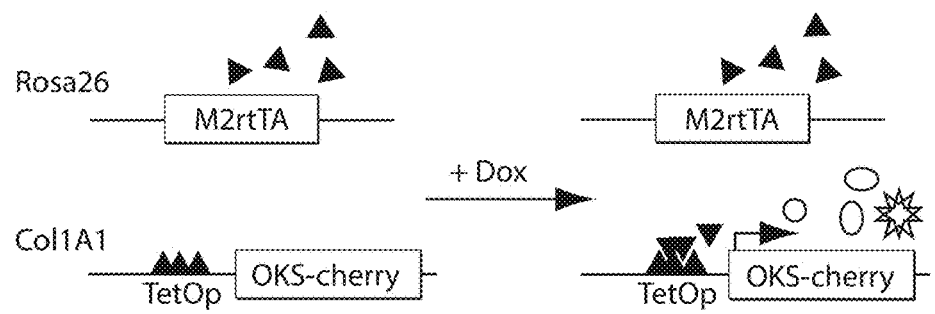
FIGS. 4A-4F.
Figure 4B:
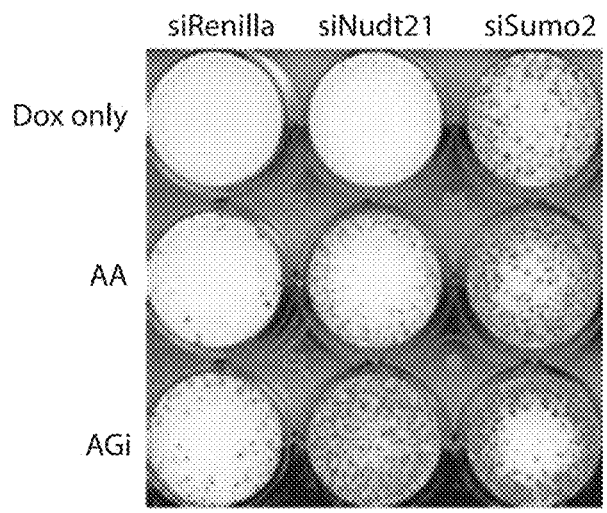
Figure 4C:
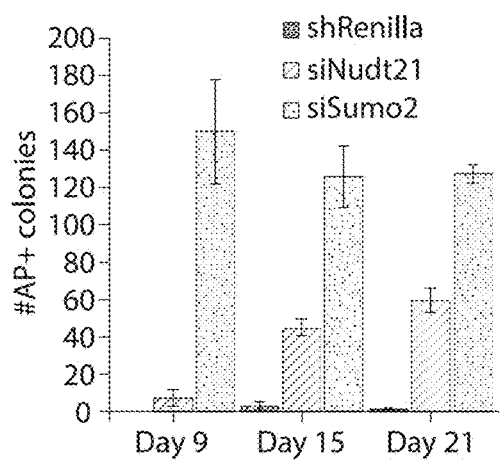
Figure 4D:
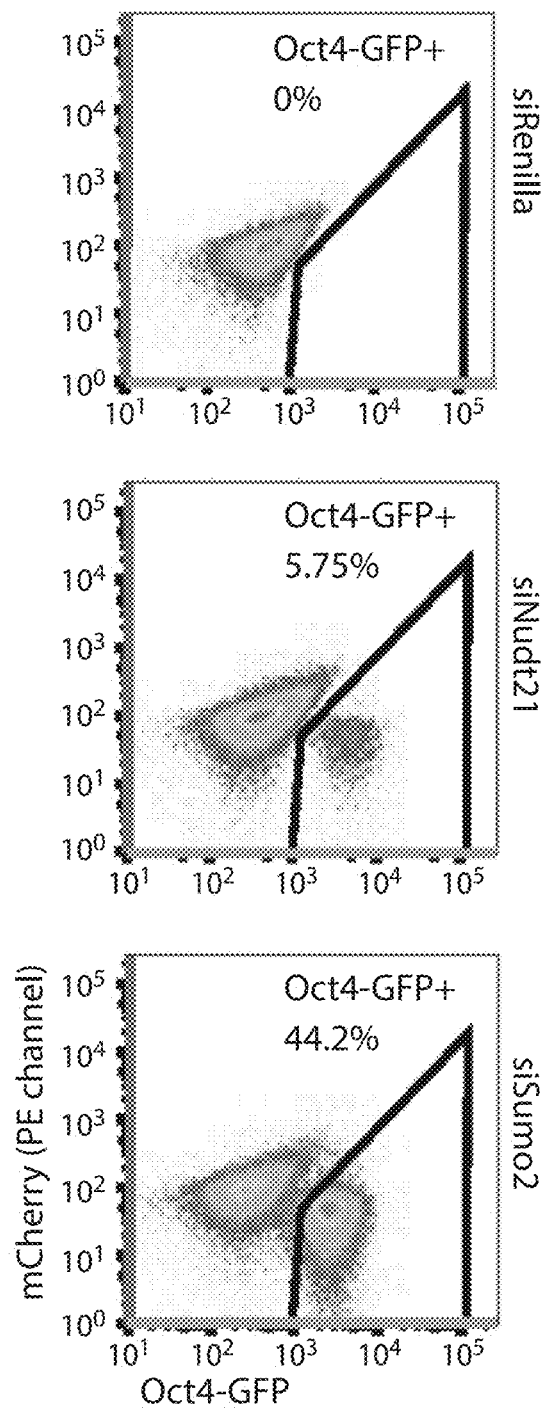

Nudt21 and Sumo2 Suppression Act Independently of c-Myc Expression and in Parallel with Small Molecule Enhancers of Reprogramming It was next investigated whether exogenous c-Myc expression was required for the enhancement of iPSC formation by Sumo2 shRNAs and Nudt21 shRNAs, as was previously observed for Mbd3 depletion (Rais et al., 2013). To this end, reprogrammable MEFs were derived from mice carrying the Col1a1-tetOP-OKS-mCherry allele (lacking the c-Myc transgene) in combination with the R26-M2rtTA allele (FIG. 4A). Exposure of these MEFs to dox alone gave rise to extremely few, if any, AP+ colonies after 9-21 days of OKSM expression, and no Oct4-GFP positive cells could be detected by day 9 of reprogramming (FIGS. 4B-4D). In stark contrast, depletion of Sumo2 or Nudt21 in these cells using transient transfection of siRNA pools readily yielded iPSC colonies and stable Oct4-GFP+ cells by flow cytometry after as little as 9 days of OKSM expression. It was concluded that suppression of Nudt21 or Sumo2 enhances reprogramming independently of exogenous c-Myc expression, thus enabling iPSC formation from cells under conditions that bypass the use of this potent oncogene.

Figure 4E:
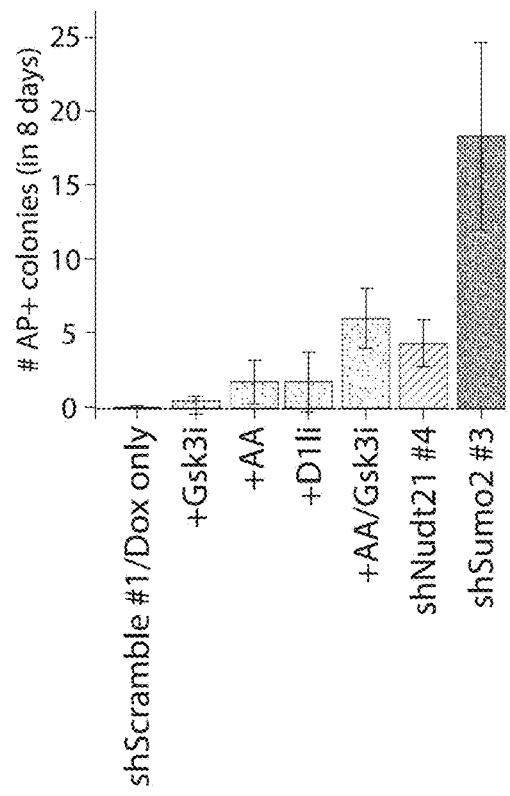
Figure 4F:
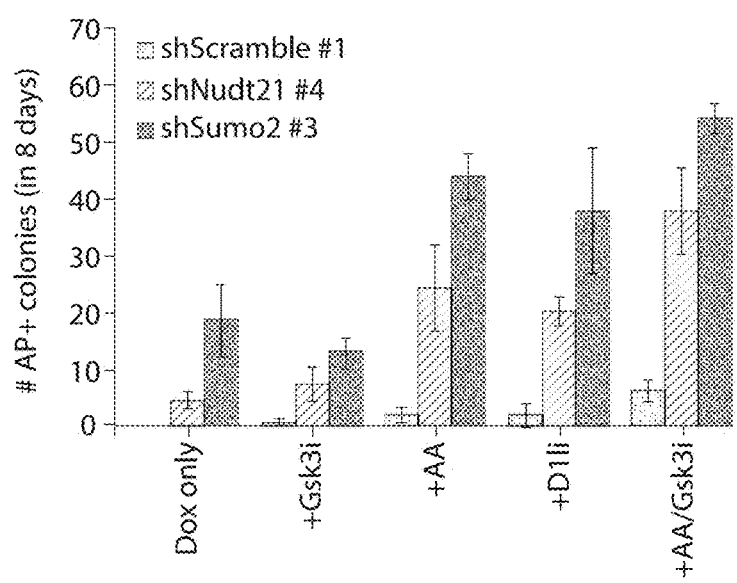

To determine whether Nudt21 and Sumo2 suppression act in parallel with small molecules that were previously shown to enhance reprogramming, the inventors treated reprogrammable cells harboring shRNAs against Sumo2, Nudt21 or Firefly luciferase with doxycycline in the presence or absence of ascorbic acid (AA)(Esteban et al., 2010), a Dotl1 inhibitor (Dotl1i)(Onder et al., 2012) and a Gsk3 inhibitor (Gsk3i)(Silva et al., 2008)(FIG. 4E). Consistent with previous reports, it was found that exposure of reprogrammable cells to each of these compounds significantly enhanced the generation of AP+ iPSC colonies, with combined ascorbate/GSK3 inhibitor treatment (AGi) exhibiting the strongest effect. Strikingly, Nudt21 suppression alone was as effective as AGi treatment while Sumo2 depletion alone even surpassed the effect of AGi on AP+ colony formation (FIG. 4E). Moreover, suppression of either Sumo2 or Nudt21 further enhanced iPSC formation in the presence of ascorbate, Gsk3i or Dotl1i (FIG. 4F). These results underscore the strong effects of individual Nudt21 and Sumo2 suppression on the reprogramming process and indicate that the sumoylation and polyadenylation pathways may act in parallel to previously described mediators of iPSC formation including ascorbic acid, H3K79 methylation and Gsk3 signaling.

Generation of iPSCs after as Little as 36-48 Hours of OKSM Expression

Figure 5D:
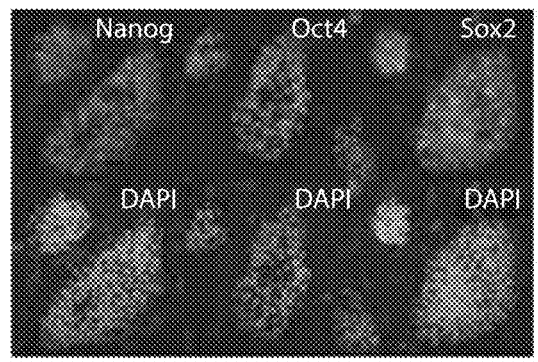
Figure 5E:
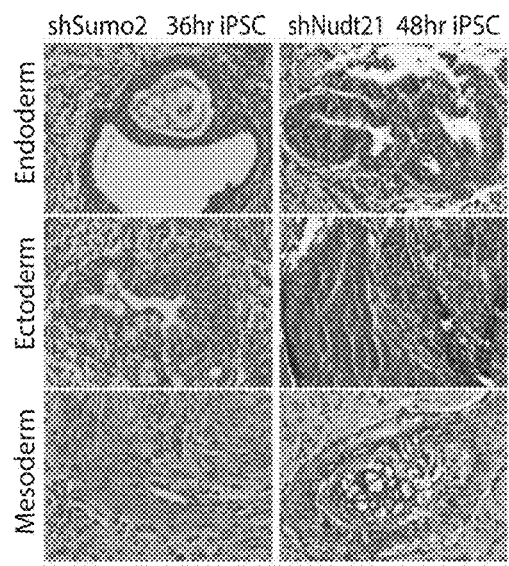
Figure 5F:
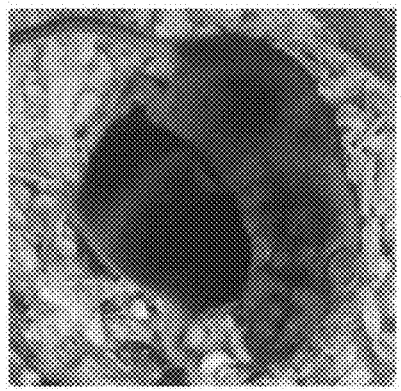

Given the additive effect of Nudt21 and Sumo2 suppression with small molecule enhancers of reprogramming, the inventors tested whether this combination treatment would allow them to further reduce the minimal time period of OKSM expression required to produce stable transgene-independent iPSCs. Early passage reprogrammable MEFs (passage 2) carrying two copies each of the Col1a1-tetOP-OKSM and R26-M2rtTA alleles were used to achieve optimal reprogramming efficiencies. MEFs exposed to Dotl1i, Gsk3i and AA required at least 3 days of OKSM expression to produce dox-independent AP+ iPSCs, which is faster than any previously reported protocol. Remarkably, suppression of either Nudt21 or Sumo2 further reduced this time window to 36 h using Sumo2 shRNAs and 48 h using Nudt21 shRNAs (FIGS. 5A-5C). Emerging iPSC colonies activated the endogenous Oct4-GFP reporter, expressed Nanog and Sox2, gave rise to well-differentiated teratomas and supported the formation of coat-color chimeras, indicating that these are authentic iPSCs (FIGS. 5C-5F). These results show that 1-2 days of OKSM expression are sufficient to produce stable, pluripotent iPSCs when either Nudt21 or Sumo2 expression is transiently suppressed.

The inventors identified Sumo2 and Nudt21 as novel roadblocks to iPSC generation by combining a well-defined transgenic reprogramming system with a genome-wide shRNA screening approach. In contrast to recent shRNA or siRNA screens conducted during iPSC formation, the inventors employed a serial shRNA enrichment strategy, which may reduce the number of false positive hits and allow for selection of shRNAs with a stronger phenotype. Indeed, suppression of the top candidates, Sumo2 and Nudt21, markedly enhanced and accelerated iPSC formation compared to individual hits that emerged from previous large-scale screens or candidates that were selected based on gene expression differences between somatic and pluripotent cells. In agreement with this notion, the expression of Sumo2 and Nudt21 did not dramatically change during reprogramming. To the inventors' knowledge, OKSM expression for 36-48 hours represents the shortest time period that has been reported to generate authentic iPSCs from differentiated cells. In addition to Sumo2 and Nudt21, this screen uncovered a number of other candidate barriers to iPSC formation, which provide a rich resource for future mechanistic studies of the reprogramming process.

Both Nudt21 and Sumo2 affect post-transcriptional mechanisms, i.e., alternative polyadenylation (APA)(Di Giammartino et al., 2011) and lysine sumoylation (Hickey et al., 2012), which have not previously been recognized as roadblocks to reprogramming. While these data indicate that both proteins function during early-to-mid stages of reprogramming in a Myc-independent manner, the precise molecular mechanisms by which each factor suppresses iPSC formation remains to be elucidated. Nudt21 reportedly suppresses the switch from distal to proximal polyadenylation sites in glioblastoma cells, leading to increased expression of transcripts involved in cellular proliferation and tumorigenicity (Masamha et al., 2014). Of interest, a global switch from distal to proximal polyadenylation sites has also been observed during cellular reprogramming of MEFs into iPSCs (Ji and Tian, 2009), thus pointing to intriguing parallels between reprogramming and cancer and providing a potential mechanism by which Nudt21 may enhance iPSC generation. Without wishing to be bound by theory, the inventors surmise that Nudt21 promotes the silencing of somatic transcripts harboring distal APA sites and the expression of pluripotency-associated transcripts harboring proximal APA sites. It should be informative to follow dynamic changes in APA usage during reprogramming in the presence and absence of Nudt21 to test this hypothesis.

The present findings have practical implications for basic science and cell therapy. The ease with which Sumo2 and Nudt21 can be inhibited using transient siRNA delivery can facilitate the mechanistic dissection of the reprogramming process in more homogeneous cell cultures. The observation that Sumo2 and Nudt21 depletion cooperate with small molecule enhancers of reprogramming but do not require exogenous c-Myc expression can further facilitate the efficient and safe generation of patient-specific iPSCs from rare donor cells.

METHODS AND MATERIALS

Tissue Culture and Virus Production

Reprogrammable Mouse Embryonic Fibroblasts (rep-MEF) were derived from day E13.5-15.5 mouse embryos carrying the Col1a1-tetOP-OKSM and Rosa26-M2rtTA alleles (Stadtfeld et al., 2010). MEFs with a Col1a1-tetOP-OKS-mCherry allele were used in some experiments (Bar-Nur et al., 2014). Reprogramming was initiated in RepMEFs by adding 20 ng/ml doxycyline (dox) and, where indicated, 25 ug/ml L-Ascorbic acid (Sigma™ A4544-25G), 3 uM GSK3 inhibitor (CHIR99021, Stemgent™ or Tocris™), Alk5 inhibitor (RepSox, R0158, Sigma-Aldrich™), 1 uM MEK inhibitor (PD0325901, Stemgent™) or Dot1l inhibitor. RepMEFs were typically expanded under hypoxic (4% oxygen) conditions until dox induction. MEFs were infected with shRNA vectors at passage 4 unless noted otherwise, allowed to recover for 48-60 hours, harvested, counted and seeded at a density of 20K cells per well of a 6-well plate. Media was changed every 2 to 3 days. Dox was withdrawn by removing media, washing with 1×PBS, and continuing culture in ESC media (Knockout DMEM, 1,000 U/ml LIF, 20% FBS). For phage or GipZ virus preparation, 293T cells were seeded and transfected at 50% confluency with PEI (Polyethylenimine) and DNA (vector+psPax2 and pDM2.G) at a ratio of 3:1 in Optimem™ media (Life Technologies™). After 24 hours, supernatant was collected through a 0.4 um filter and mixed 3:1 with fresh MEF media and polybrene (10 ug/ml) for direct infection or precipitated with PEG (Polyethylglycol) and kept at −80 C for later infections. Viral transductions were performed by spin infection for 30 minutes at 2,150 rpm at room temperature. Fresh media was added ~16 hours after infections.

siRNA Transfections

Transfections of RepMEFs with siRNAs were performed in 12-well plates at the time of dox administration. Per 12-well plate, 2 ul of Lipofectamine™ 2000 was added to 75 ul of Optimem™ (Life Technologies™) and 1.5 ul of siRNA (esiRNA, Sigma™) was added to 75 ul of Optimem™; both mixtures were separately incubated at room temperature for 5 minutes, then combined and incubated for another 15 minutes before adding the solution to the reprogramming media (normal media lacking antibiotics). After overnight incubation, the transfection media was replaced with regular reprogramming media.

Flow Cytometry

To determine viral infection efficiency and cell numbers before initiation of reprogramming, infected MEFs were harvested using 0.25% trypsin-EDTA (Life Technologies™) and kept at 4° C. A small aliquot was analyzed on the MACSQuant cytometer to determine the number of cells/ml and the percentage of tRFP+ cells. To prepare growth curves, 3 replicates were harvested at each time point to measure cell counts (DAPI-negative live cells). Intermediates of reprogramming were analyzed by staining with Thy1-Viogreen (BD™), SSEA1-APC (Biolegend™), SSEA1-PE-Cy7 (Miltenyi Biotec™), and/or Epcam-PE-Cy7 (eBioscience™) (1:200 for 30 min at 4° C.). To measure the fraction of dying cells, BD™'s Annexin V kit was used according to manufacturers' instructions. All cytometry data was analyzed and plotted using FlowJo software. Fluorescence-activated cell sorting (FACS) was performed by harvesting cells with Trypsin-EDTA (Gibco™) before resuspending cells in MEF media and subsequent filtration through 100 um and 40 um filters. For isolation of Oct4-GFP+ iPSCs, SSEA1+ cells were enriched by labeling with SSEA1 antibody coated magnetic beads and MACS sorting. The positive fraction was then purified for Oct4-GFP+ cells by FACS. For analyses of pre-MACS and post-MACS samples, aliquots were stained using Thy1-Pacific Blue (eBioscience™) and SSEA1-APC (Biolegend™) antibodies, 1:200 in 1% FBS:PBS, 30 min at 4° C. Analysis was done using the FACS Diva software.

Cell Cycle Analysis

To determine cell cycle dynamics, repMEFs treated with dox for 48 h were exposed to 20 uM BrdU (Sigma™) for 30 minutes in regular media, trypsinized and kept on ice in 100 ul 1×PBS. To fix cells, 2 ml of cold EtOH was added dropwise, incubated for 30 minutes, followed by addition of 2 ml 4N HCl and another 30 minutes of incubation. Cells were then spun down at 500 rpm for 5 min. at 4 C and resuspended in 1 ml of 0.1N $Na_2B_4O_7$, pH 8.5 and washed with staining buffer (2% FBS and 0.5% Tween 20 in PBS). Antibody for BrdU (mouse, DAKO M074401-8) was added to cells for 30 min at room temperature (RT) at a concentration of 5 ug/ml, followed by 3 washes in 1×PBS and incubation with anti-mouse FITC secondary antibody (BD Biosciences™, 55434) for 30 min at RT at a dilution of 1:100. After 3 additional washes with 1×PBS, the pellet was resuspended for analysis in 2% FBS/PBS containing 5 ug/ml propidium iodide. Resuspension volume was used to normalize for cell count of each sample. Samples were analyzed immediately on the MACSQuant cytometer.

Quantification of Reprogramming Efficiencies

For macroscopic detection of iPSC colonies, Alkaline Phosphatase (AP) staining was carried out according to manufacturer's instructions using the Vector Labs™ AP staining kit (#5100). AP staining was always performed 2 to 4 days after dox withdrawal to eliminate partially reprogrammed colonies and score for transgene independent iPSCs. Colonies were counted manually or by custom-made Nikon™ software (CL-Quant™).

Teratoma and Chimera Formation

For teratoma generation, iPSC lines (passage 6 or higher) were harvested and resuspended in 600 ul media per confluent 6-well. Mice were anesthetized with Avertin and injected with 150 ul cell suspension subcutaneously. Tumors were harvested 3 to 4 weeks after injection and analyzed histologically. For chimera production, iPSC lines were injected as single cell suspension into day 3.5 blastocysts isolated from intercrosses of C57Bl/6×BDF1 mice. Blastocysts were transferred into pseudo-pregnant Swiss Webster recipient animals.

Immunofluorescence Analysis iPSC lines (passage 6 or higher) were seeded in a 24-well plate at a low density. Once small colonies emerged, wells were washed with 1×PBS and fixed by a 5-10 minute incubation in 10% formalin at room temperature. After washes in 1×PBS, cells were blocked in 1×PBS containing 2% BSA and 0.1% Triton-X 100. Primary and secondary antibodies were diluted in blocking solution at a concentration of 1:200 and added for 1 hour at RT or overnight at 4 C. Primary antibodies were anti-mouse Nanog (Abcam™), Sox2 and Oct4 (Santa Cruz™); secondary antibodies were donkey anti-goat IgG or donkey anti-rabbit IgG Alexa Fluor 546-conjugated antibodies (Life Technologies™) After 2 washes in 1×PBS, cells were immobilized on slides in mounting media containing DAPI (Vectashield™, Vector Labs™) and analyzed.

RNA Expression Analysis

Total RNA was isolated from repMEFs in triplicates exposed to dox for 3 or 6 days using the QIAGEN™ RNeasy™ Mini kit and sequencing libraries were prepared as described (Shepard et al., 2011) and sequenced at the Tufts University Genomics core. Activation of pluripotency-associated genes at day 6 of reprogramming was determined based on these expression data. For quantitative PCR analysis, Brilliant III SYBR-green based master mix was used according to the manual (Agilent™), following RNA isolation (RNeasy™ kit, QIAGEN™) and reverse transcription (Transcriptor First Strand cDNA Synthesis Kit, Roche™) of Nudt21, Sumo2, or control knockdown samples two days after initiation of reprogramming. Samples were run in triplicate on the Lightcycler 480 (Roche™).

Western Blot Analysis

Protein lysates were run on 4-20% Mini Protean TGX gels (Bio-Rad™), blotted onto Immobilon-P membrane (EMD Millipore™) and stained with anti-Nudt21 (Santa Cruz™), anti-Sumo2 (Life Technologies™) or anti-Actin (Abcam™) antibodies.

shRNA Screen and Hits Identification

RepMEFs were expanded until passage 4 in 4% oxygen, switched to atmospheric oxygen, and infected with the pooled shRNA library as described above. For each shRNA (621,000 shRNAs in total), $1-2\times10^3$ cells were infected to achieve good coverage. Infected cells were passaged onto gelatinized 15 cm cell culture dishes (Falcon™) in reprogramming media (ESC media supplemented with ascorbic acid and doxycycline) for 10 days, and in doxycycline/ascorbic acid-free ESC media for an additional 4 days. Cells were harvested, pooled, and purified with SSEA1-linked magnetic beads using an AutoMACS sorter (Miltenyi™). SSEA1-enriched cells were then FACS-sorted for endogenous Oct4-GFP expression.

Genomic DNA was extracted from collected Oct4-GFP+ cells by lysing the cells in 10 mM Tris pH 8.0, 10 mM EDTA, 10 mM NaCl, 0.5% Sarkosyl. Lysates were treated with 0.1 mg/ml Rnase A at 37° C. for 30 min, 0.5 mg/ml Proteinase K at 55° C. for 1-2 hr, and then phenol chloroform extracted, ethanol precipitated, and resuspended in 10 mM Tris-HCl pH 8.0. For each sample, all of the genomic DNA was used as template for shRNA PCR, usually in multiple PCR reactions. Each 50 µl PCR reaction contained: 2.5 µg genomic DNA template, 200 uM dNTPs, 400 nM of each PCR primer (pHAGE-Mir-PCR: 5'-GCAAACTGGGGCACAGATGATGCGG (SEQ ID NO: 1); BC1R L: 5'-CGCCTCCCCTACCCGGTAGA) (SEQ ID NO: 2)), 1×Q5 reaction buffer, 1×Q5 high GC buffer, and 0.5 µl Q5 polymerase (NEB™). PCR was performed with the following program: 94° C. 4 min, 35 cycles of (94° C. 30 sec, 60° C. 30 sec, 72° C. 45 sec), 72° C. 10 min. PCR products (~700 bp) for each sample were pooled, ethanol precipitated, resuspended, and gel-purified using the QIAquick™ Gel Extraction Kit (Qiagen™). The purified shRNA PCR products were used to: 1) generate sublibraries for the next round of shRNA library screens; 2) generate sequencing libraries for Solexa sequencing.

For sub-library generation, the purified PCR product was digested with NotI and MluI, and the ~400 bp fragment that contains the shRNAs was gel-purified. Separately, the pHAGE-Mir plasmid was also digested with NotI and MluI to recover the ~9 kb vector backbone. 25-50 ng of the purified shRNA fragment and 125-250 ng of the vector backbone were ligated in 5 ul ligation reaction using NEB™ T4 ligase. 1 ul ligation reaction was used to transform 20 ul Electromax competent cells DH10b (Life Technology™) with electroporation. 1 ul of the transformation reaction was plated on one 10-cm LB-Amp (100 ug/ml) plate to estimate the total number of colonies, and the rest of the transformation reaction was plated on two 15-cm LB-Carbenicillin (100 ug/ml) plates and grown overnight at 37° C. To maintain the representation of the library, at least 100× coverage was needed (i.e., colony number=100× number of shRNAs in the library). When necessary, the entire ligation reaction may be used for transformation in multiple electroporation reactions to increase the number of colonies. The next day, lawn formed on the two 15-cm plates were scraped off and cultured in 300 ml LB-Carbenicillin (100 ug/ml) medium and grown at 30° C. for 2-3 hrs. The bacteria was collected and the cloned sub-library DNA was extracted by the Genelute™ Maxiprep kit (Sigma™).

For Solexa sequencing, the purified shRNA PCR product was used as template for another round of PCR: 500 ng purified shRNA PCR product, 200 uM dNTPs, 2 uM of each PCR primer (p5 and p7), 1×Q5 reaction buffer, 1×Q5 high GC buffer, and 1 µl Q5 polymerase (NEB™) in 100 ul PCR reaction. PCR was performed with the following program: 94° C. 4 min, 2 cycles of (94° C. 30 sec, 50° C. 20 sec, 72° C. 30 sec), 20 cycles of (94° C. 30 sec, 60° C. 20 sec, 72° C. 30 sec), 72° C. 10 min. PCR products (~120 bp) were and gel-purified using the QIAquick™ Gel Extraction Kit (Qiagen™). Gel-purified products were submitted for Solexa™ sequencing on the Illumina™ MiSeq instrument, using a custom sequencing primer: mir30-EcoRI: 5'-TAGCCCCT-TGAATTCCGAGGCAGTAGGCA (SEQ ID NO: 3).

PCR Primers:

```
p5-miSeq:
                                    (SEQ ID NO: 4)
5'-ATGATACGGCGACCACCGAGATCTACACCTAAAGTAGCCCCTTGAAT
TC;

p7-miSeq-1:
                                    (SEQ ID NO: 5)
5'-CAAGCAGAAGACGGCATACGAGACGATAGTGAAGCCACAGATGTA;

p7-miSeq-2:
                                    (SEQ ID NO: 6)
5'-CAAGCAGAAGACGGCATACGAGACACTAGTGAAGCCACAGATGTA;

p7-miSeq-3:
                                    (SEQ ID NO: 7)
5'-CAAGCAGAAGACGGCATACGAGACTATAGTGAAGCCACAGATGTA;

p7-miSeq-4:
                                    (SEQ ID NO: 8)
5'-CAAGCAGAAGACGGCATACGAGACCTTAGTGAAGCCACAGATGTA.
```

Different p7 primers were used for multiplexing purpose.

Single-end 51 bp reads were obtained using the Illumina HiSeq or MiSeq instrument. The reads are expected to have an initial 22 nucleotides that identify the shRNA, followed by a constant region that is the same for all shRNAs and a 2 nucleotide barcode to identify the sample. Reads that contain perfect matches at the following 6 nucleotides were first extracted from the sequencing data: the 2 nucleotides adjacent to the initial 22 base sequence and the 2 nucleotides adjacent to the barcode on both sides. The shRNAs were then identified by requiring an exact match of the 22 nucleotides to the sequences in the shRNA library annotation file. The samples were identified by the 2 nucleotide barcodes.

The total number of reads that were identified for each shRNA, sample, and round were counted. The counts were normalized to be directly comparable between samples and rounds by first dividing by the total number of counts for that sample and round and then multiplying by the total number of shRNAs in the initial library. A pseudocount of 1 was added to each normalized count to downweight enrichment derived from low read counts and to avoid division by zero in calculating fold-changes.

The enrichment for each shRNA in each round was calculated as the log 2 fold change of the Oct4-GFP+ normalized counts over the maximum of the normalized counts of the controls (T0, No-Dox, and Oct4-GFP−). The cumulative enrichment for each shRNA in each round was calculated as the sum of the log 2 fold changes for that round and all previous rounds. The overall enrichment of each shRNA was defined as the maximum of the cumulative enrichment scores among all rounds.

The heat map for FIG. 1J was plotted using the cumulative enrichment scores. Only shRNAs that have at least one read in the Oct4-GFP+ sample in at least two rounds were used in the plot, resulting a total of 23,853 shRNAs.

TABLE 1

List of Primers

| Target | Purpose | Forward oligo | Reverse Oligo |
|---|---|---|---|
| Nudt21 | qPCR | CGGCTTCTTTTACTTC TGCATAC (SEQ ID NO: 9) | GGGGTATGGACCCATC ATTT (SEQ ID NO: 14) |
| Sumo2 | qPCR | AAGGAAGGAGTCAAGA CTGAGAA (SEQ ID NO: 10) | CGGAATCTGATCTGCC TCATTG (SEQ ID NO: 15) |
| GAPDH | qPCR | AGG TCG GTG TGA ACG GAT TTG (SEQ ID NO: 11) | TGT AGA CCA TGT AGT TGA GGT CA (SEQ ID NO: 16) |
| phage vector | recloning shRNA | PCR5-3: GCAAACTGGGGCACA GATGATGCGG | BC1R: CGCCTCCCCTACCCGG TAGA |
| phage vector | sequencing shRNA | TAGCCCCTTGAATTCC GAGGCAGTAGGCA (SEQ ID NO: 3) | N/A |
| phage vector | half hairpin amplification for sequencing library | JH353F: TAGTGAAGCCACAGA TGTA (SEQ ID NO: 12) | BC1R: CGCCTCCCCTACCCGG TAGA (SEQ ID NO: 2) |

TABLE 1-continued

List of Primers

| Target | Purpose | Forward oligo | Reverse Oligo |
|---|---|---|---|
| half hairpin amplicon | adaptor addition for Solexa sequencing | P5 + mir3: AATGATACGGCGACC ACCGACTAAAGTAGC CCCTTGAATTC (SEQ ID NO: 13) | P7 + loop: Barcode xx = GA, TG or AT: CAAGCAGAAGACGGCA TACGAxxTAGTGAAGC CACAGATGTA (SEQ ID NO: 17) |

REFERENCES FOR EXAMPLE 1

Apostolou, E., and Hochedlinger, K. (2013). Chromatin dynamics during cellular reprogramming. Nature 502, 462-471.

Di Giammartino, D. C., Nishida, K., and Manley, J. L. (2011). Mechanisms and consequences of alternative polyadenylation. Molecular cell 43, 853-866.

Esteban, M. A., Wang, T., Qin, B., Yang, J., Qin, D., Cai, J., Li, W., Weng, Z., Chen, J., Ni, S., et al. (2010). Vitamin C enhances the generation of mouse and human induced pluripotent stem cells. Cell stem cell 6, 71-79.

Hickey, C. M., Wilson, N. R., and Hochstrasser, M. (2012). Function and regulation of SUMO proteases. Nature reviews Molecular cell biology 13, 755-766.

Jackson-Grusby, L., Beard, C., Possemato, R., Tudor, M., Fambrough, D., Csankovszki, G., Dausman, J., Lee, P., Wilson, C., Lander, E., et al. (2001). Loss of genomic methylation causes p53-dependent apoptosis and epigenetic deregulation. Nature genetics 27, 31-39.

Ji, Z., and Tian, B. (2009). Reprogramming of 3' untranslated regions of mRNAs by alternative polyadenylation in generation of pluripotent stem cells from different cell types. PloS one 4, e8419.

Kawamura, T., Suzuki, J., Wang, Y. V., Menendez, S., Morera, L. B., Raya, A., Wahl, G. M., and Izpisua Belmonte, J. C. (2009). Linking the p53 tumour suppressor pathway to somatic cell reprogramming. Nature 460, 1140-1144.

Li, H., Collado, M., Villasante, A., Strati, K., Ortega, S., Canamero, M., Blasco, M. A., and Serrano, M. (2009). The Ink4/Arf locus is a barrier for iPS cell reprogramming. Nature 460, 1136-1139.

Masamha, C. P., Xia, Z., Yang, J., Albrecht, T. R., Li, M., Shyu, A. B., Li, W., and Wagner, E. J. (2014). CFIm25 links alternative polyadenylation to glioblastoma tumour suppression. Nature 510, 412-416.

Mikkelsen, T. S., Hanna, J., Zhang, X., Ku, M., Wernig, M., Schorderet, P., Bernstein, B. E., Jaenisch, R., Lander, E. S., and Meissner, A. (2008). Dissecting direct reprogramming through integrative genomic analysis. Nature 454, 49-55.

Neyret-Kahn, H., Benhamed, M., Ye, T., Le Gras, S., Cossec, J. C., Lapaquette, P., Bischof, O., Ouspenskaia, M., Dasso, M., Seeler, J., et al. (2013). Sumoylation at chromatin governs coordinated repression of a transcriptional program essential for cell growth and proliferation. Genome research 23, 1563-1579.

Onder, T. T., Kara, N., Cherry, A., Sinha, A. U., Zhu, N., Bernt, K. M., Callan, P., Marcarci, B. O., Unternaehrer, J., Gupta, P. B., et al. (2012). Chromatin-modifying enzymes as modulators of reprogramming. Nature 483, 598-602.

Plank, M., Hu, G., Silva, A. S., Wood, S. H., Hesketh, E. E., Janssens, G., Macedo, A., de Magalhaes, J. P., and Church, G. M. (2013). An analysis and validation pipeline for large-scale RNAi-based screens. Scientific reports 3, 1076.

Poleshko, A., Kossenkov, A. V., Shalginskikh, N., Pecherskaya, A., Einarson, M. B., Marie Skalka, A., and Katz, R. A. (2014). Human factors and pathways essential for mediating epigenetic gene silencing. Epigenetics: official journal of the DNA Methylation Society 9, 1280-1289.

Polo, J. M., Anderssen, E., Walsh, R. M., Schwarz, B. A., Nefzger, C. M., Lim, S. M., Borkent, M., Apostolou, E., Alaei, S., Cloutier, J., et al. (2012). A molecular roadmap of reprogramming somatic cells into iPS cells. Cell 151, 1617-1632.

Qin, H., Diaz, A., Blouin, L., Lebbink, R. J., Patena, W., Tanbun, P., LeProust, E. M., McManus, M. T., Song, J. S., and Ramalho-Santos, M. (2014). Systematic identification of barriers to human iPSC generation. Cell 158, 449-461.

Rais, Y., Zviran, A., Geula, S., Gafni, O., Chomsky, E., Viukov, S., Mansour, A. A., Caspi, I., Krupalnik, V., Zerbib, M., et al. (2013). Deterministic direct reprogramming of somatic cells to pluripotency. Nature 502, 65-70.

Samavarchi-Tehrani, P., Golipour, A., David, L., Sung, H. K., Beyer, T. A., Datti, A., Woltjen, K., Nagy, A., and Wrana, J. L. (2010). Functional genomics reveals a BMP-driven mesenchymal-to-epithelial transition in the initiation of somatic cell reprogramming. Cell stem cell 7, 64-77.

Silva, J., Barrandon, O., Nichols, J., Kawaguchi, J., Theunissen, T. W., and Smith, A. (2008). Promotion of reprogramming to ground state pluripotency by signal inhibition. PLoS Biol 6, e253.

Stadtfeld, M., and Hochedlinger, K. (2010). Induced pluripotency: history, mechanisms, and applications. Genes Dev 24, 2239-2263.

Stadtfeld, M., Maherali, N., Borkent, M., and Hochedlinger, K. (2010). A reprogrammable mouse strain from gene-targeted embryonic stem cells. Nat Methods 7, 53-55.

Tahmasebi, S., Ghorbani, M., Savage, P., Gocevski, G., and Yang, X. J. (2014). The SUMO conjugating enzyme Ubc9 is required for inducing and maintaining stem cell pluripotency. Stem Cells 32, 1012-1020.

Tahmasebi, S., Ghorbani, M., Savage, P., Yan, K., Gocevski, G., Xiao, L., You, L., and Yang, X. J. (2013). Sumoylation of Kruppel-like factor 4 inhibits pluripotency induction but promotes adipocyte differentiation. The Journal of biological chemistry 288, 12791-12804.

Takahashi, K., and Yamanaka, S. (2006). Induction of pluripotent stem cells from mouse embryonic and adult fibroblast cultures by defined factors. Cell 126, 663-676.

Tsuruzoe, S., Ishihara, K., Uchimura, Y., Watanabe, S., Sekita, Y., Aoto, T., Saitoh, H., Yuasa, Y., Niwa, H., Kawasuji, M., et al. (2006). Inhibition of DNA binding of Sox2 by the SUMO conjugation. Biochemical and biophysical research communications 351, 920-926.

Utikal, J., Polo, J. M., Stadtfeld, M., Maherali, N., Kulalert, W., Walsh, R. M., Khalil, A., Rheinwald, J. G., and Hochedlinger, K. (2009). Immortalization eliminates a roadblock during cellular reprogramming into iPS cells. Nature 460, 1145-1148.

Wang, L., Wansleeben, C., Zhao, S., Miao, P., Paschen, W., and Yang, W. (2014). SUMO2 is essential while SUMO3 is dispensable for mouse embryonic development. EMBO reports 15, 878-885.

Wang, T., Chen, K., Zeng, X., Yang, J., Wu, Y., Shi, X., Qin, B., Zeng, L., Esteban, M. A., Pan, G., et al. (2011). The histone demethylases Jhdm1a/1b enhance somatic cell reprogramming in a vitamin-C-dependent manner. Cell stem cell 9, 575-587.

Wu, Y., Guo, Z., Wu, H., Wang, X., Yang, L., Shi, X., Du, J., Tang, B., Li, W., Yang, L., et al. (2012). SUMOylation represses Nanog expression via modulating transcription factors Oct4 and Sox2. PloS one 7, e39606.

Yang, C. S., Chang, K. Y., and Rana, T. M. (2014). Genome-wide functional analysis reveals factors needed at the transition steps of induced reprogramming. Cell reports 8, 327-337.

Example 2: The Histone Chaperone CAF-1 Safeguards Somatic Cell Identity During Transcription Factor-Induced Reprogramming The generation of iPSCs from somatic cells upon forced expression of the transcription factors Oct4, Klf4, Sox2 and c-Myc (OKSM) is a highly dynamic and lengthy process that proceeds through heterogeneous intermediate cell populations, which poses challenges for genetic and biochemical dissection of the underlying mechanisms (9, 10). Previous efforts to identify chromatin modulators of iPSC formation included gain and loss of function screens as well as transcriptional profiling of bulk or FACS-enriched cell populations undergoing reprogramming. While informative, these approaches remain limited in several ways. For example, iPSC modulators that do not change transcriptionally are typically overlooked when analyzing expression dynamics in reprogramming intermediates (11). Moreover, known repressors of iPSC formation such as p53, Mbd3, Dot11, and Dnmt1 were either predicted or identified from small sets of candidate gene lists, leaving open the possibility that major roadblocks to reprogramming remain to be discovered (12-15). Genome-wide RNAi screens are challenging due to various technical limitations such as lack of effective shRNAs when expressed from a single genomic copy, prevalent off-target effects, as well as biases in the library representation or the screening readout (11, 16, 17). Indeed, previous RNAi screens identified a number of chromatin regulators of iPSC formation with little to no overlap among independent studies. Furthermore, certain chromatin regulators reportedly have opposing effects on iPSC generation when tested in different cellular contexts and culture conditions, indicating that they may not act as universal barriers to reprogramming (14, 18-23). Although these functional and molecular analyses of iPSC formation provided important insights into transcription factor-induced reprogramming, the cellular and molecular mechanisms inherent to the induction of pluripotency and their parallels to other types of cell fate change remain largely elusive (24, 25).

To systematically explore chromatin factors involved in the maintenance of somatic cell identity, the inventors assembled custom-designed microRNA-based shRNA libraries targeting known and predicted chromatin regulators. 243 known chromatin regulators were used in an arrayed screening approach during the reprogramming of fibroblasts into iPSCs (26). This screen validated previously implicated chromatin pathways and revealed novel, more potent repressors of reprogramming. Through a series of cellular and molecular studies, the inventors demonstrate that suppression of a histone chaperone complex most dramatically enhances and accelerates iPSC reprogramming as well as other cell fate transitions. It is proposed that this complex functions as a key determinant of cell identity by influencing chromatin structure and transcription factor binding.

Chromatin Focused shRNAmir Screens Systematically Identify Global Suppressors of Reprogramming.

To explore chromatin barriers to induced pluripotency in a systematic and comprehensive manner, the inventors used a chromatin-focused screening method to identify microRNA-based shRNA (shRNAmir) libraries in a highly standardized reprogramming assay. Specifically, they utilized transgenic ("reprogrammable") mouse embryonic fibroblasts (MEF) harboring a doxycycline (dox)-inducible polycistronic OKSM cassette and a constitutive M2-rtTA driver (26). By ensuring controllable and homogeneous factor expression, this system enables the generation of stable, transgene-independent iPSCs with reproducible kinetics and frequencies. The screening platform further provides a means to study changes in the temporal requirement for OKSM overexpression while suppressing candidate chromatin barriers during induced pluripotency.

Figure 10A:
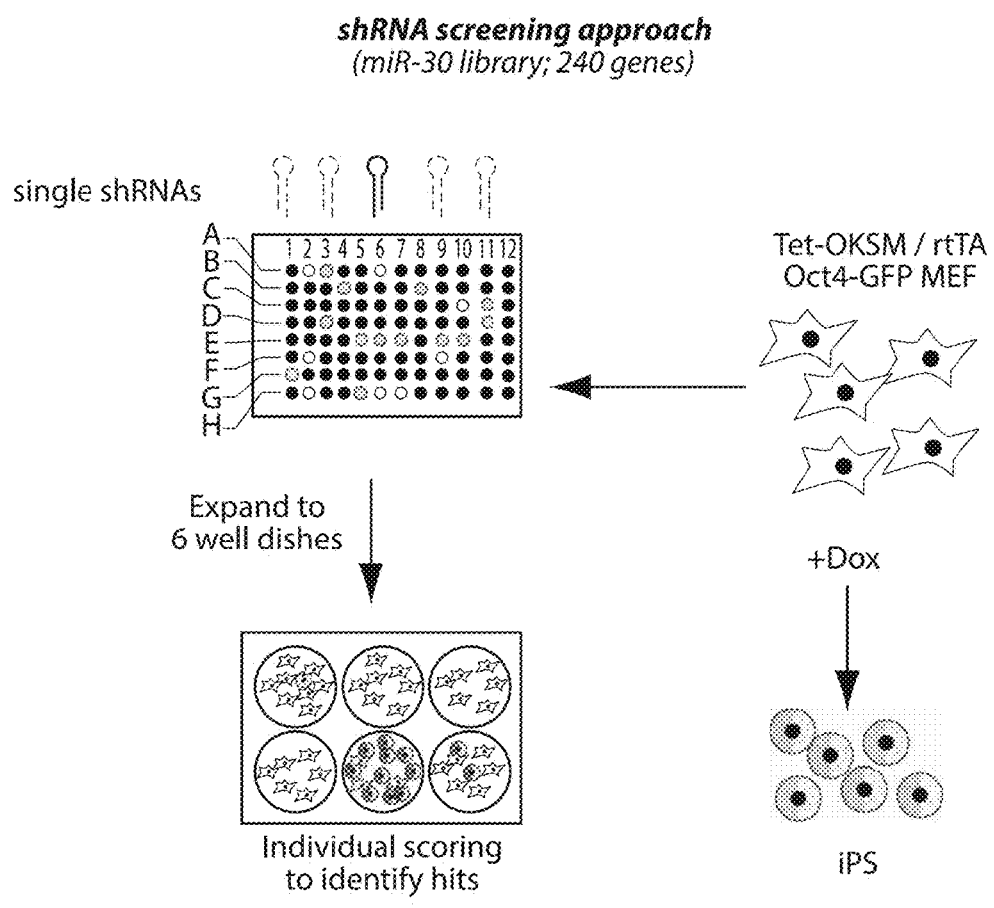
FIGS. 10A-10B.
Figure 12A:
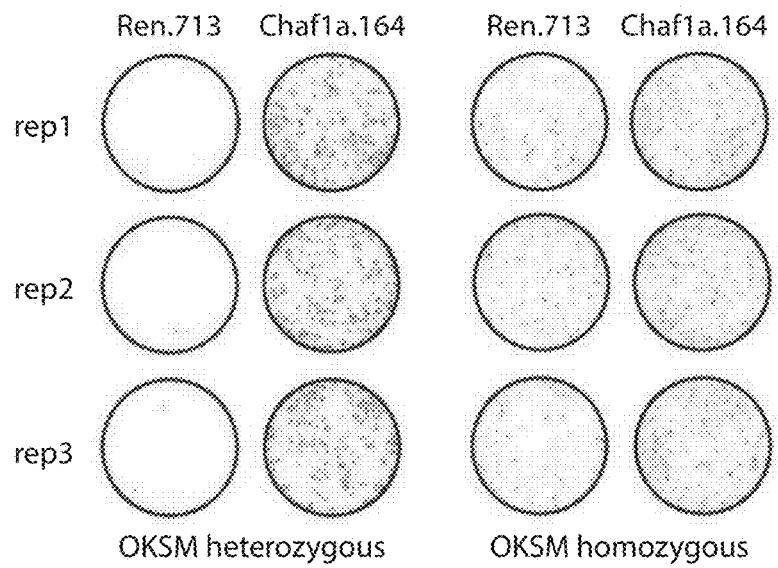
FIGS. 12A-12E.

An arrayed screening strategy was designed using a previously described miR30-based shRNA library targeting 243 known chromatin regulators (27) (FIG. 12A). A total of 1,071 experimental and four control shRNAmirs were cloned into a constitutive retroviral expression vector (pLMN) and transduced one-by-one into reprogrammable MEFs (FIG. 10A). Cells were induced to reprogram by addition of dox, followed by a period of dox withdrawal to select for transgene-independent iPSC colonies. Alkaline phosphatase positive (AP+) iPSC-like colonies were quantified using customized image analysis software, and reprogramming efficiency ratios were calculated relative to a control shRNA targeting Renilla luciferase (Ren.713).

Nucleosome Assembly as a Major Roadblock to iPSC Formation

Figure 10B:
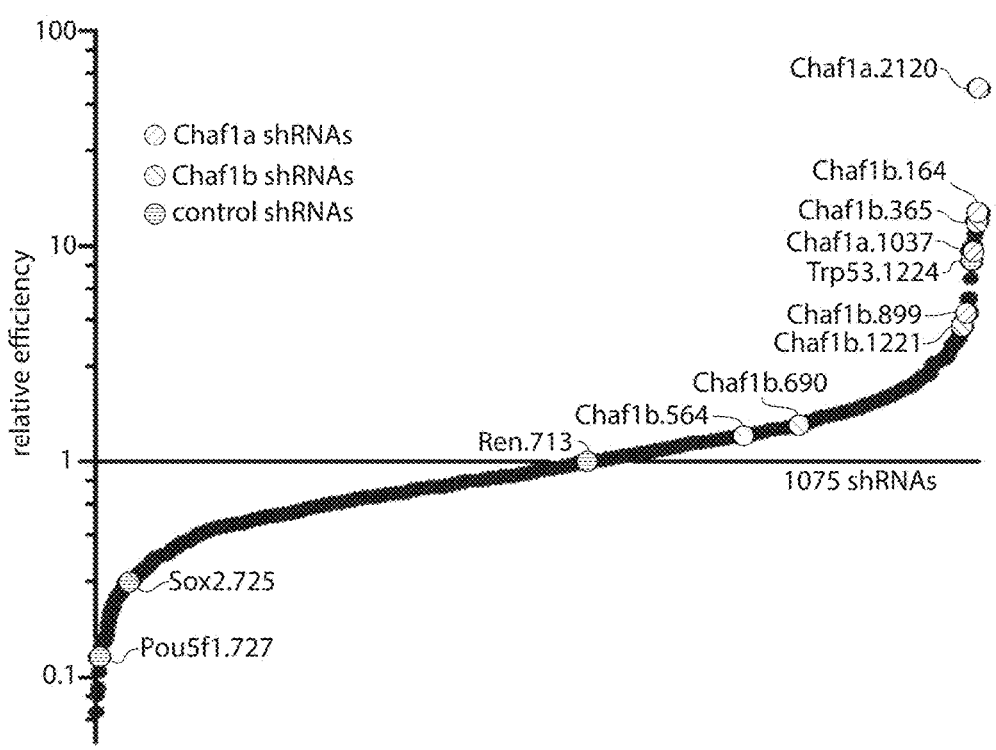
Figure 11A:
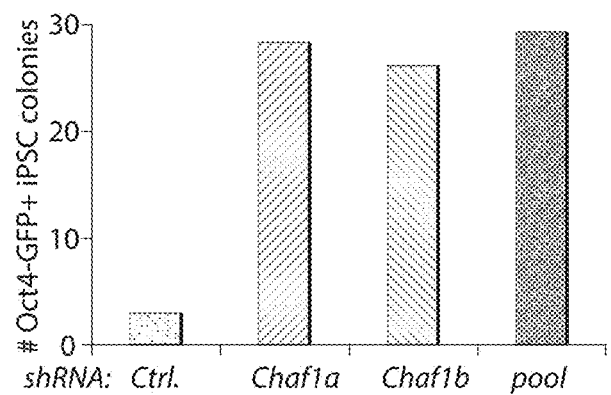
FIGS. 11A-11C.
Figure 15A:
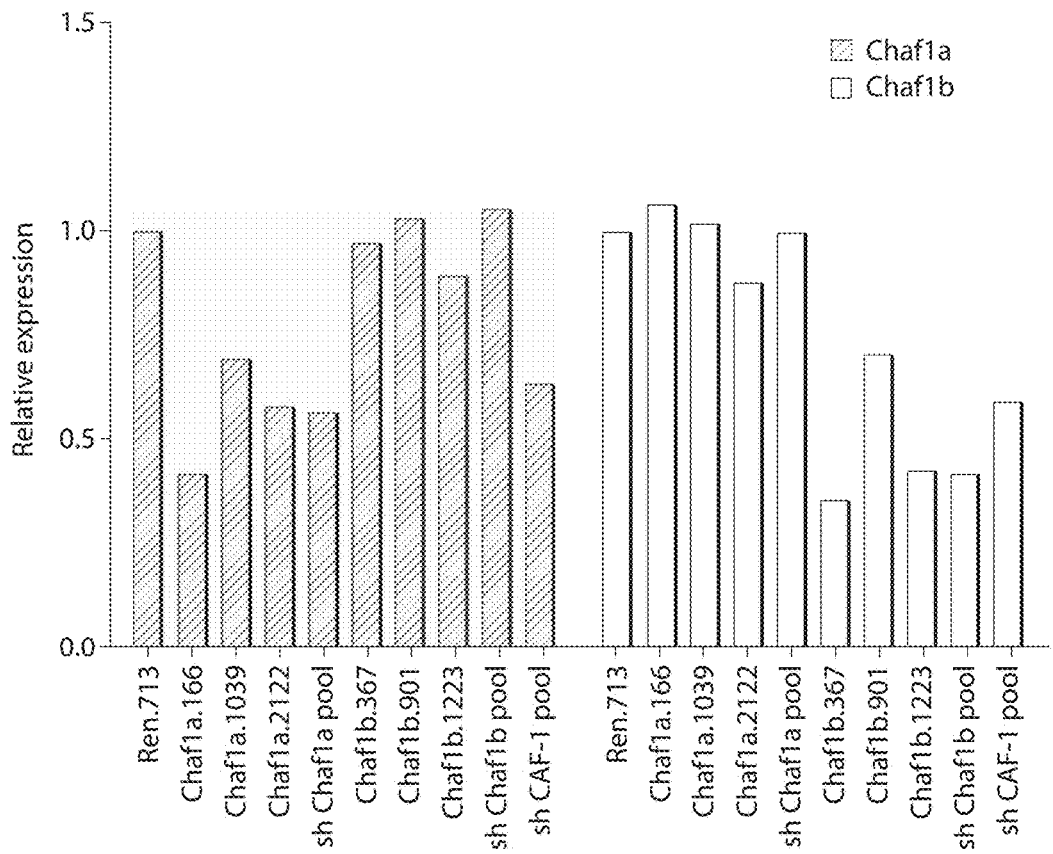
FIGS. 15A-15B.
Figure 15B:
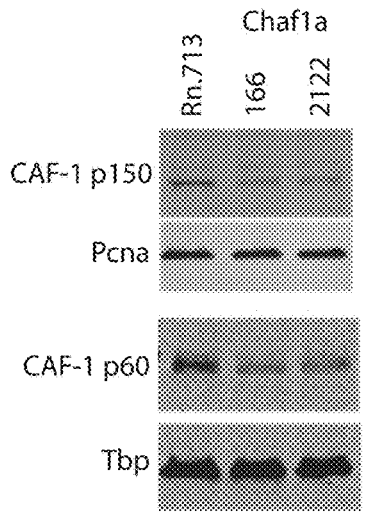
Figure 16A:
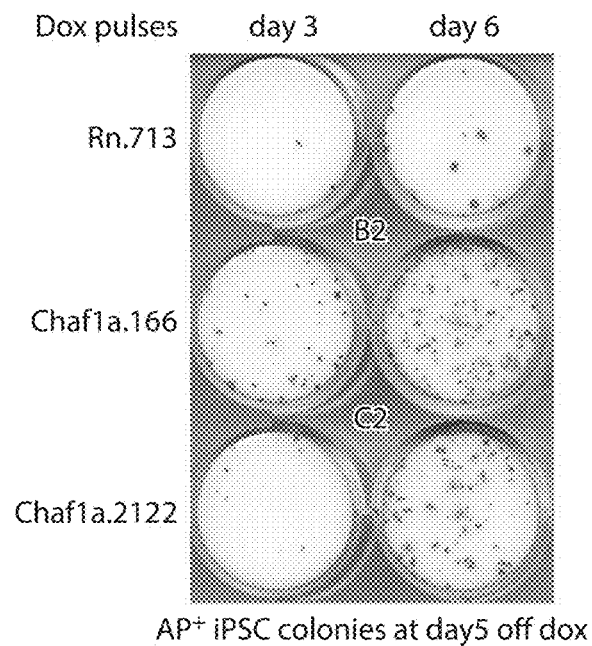
FIGS. 16A-16C.
Figure 16B:
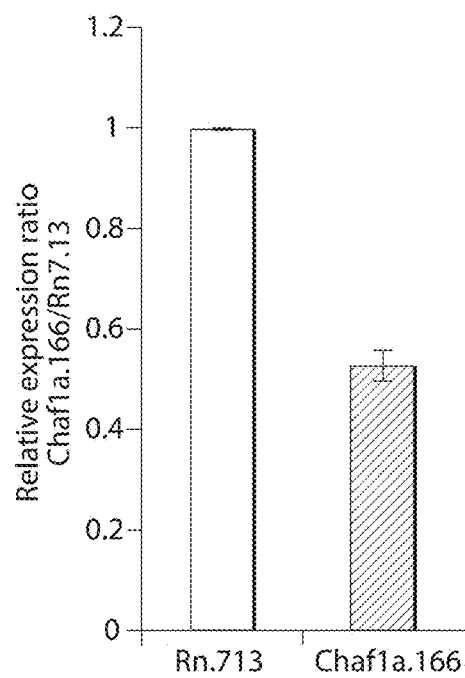
Figure 16C:
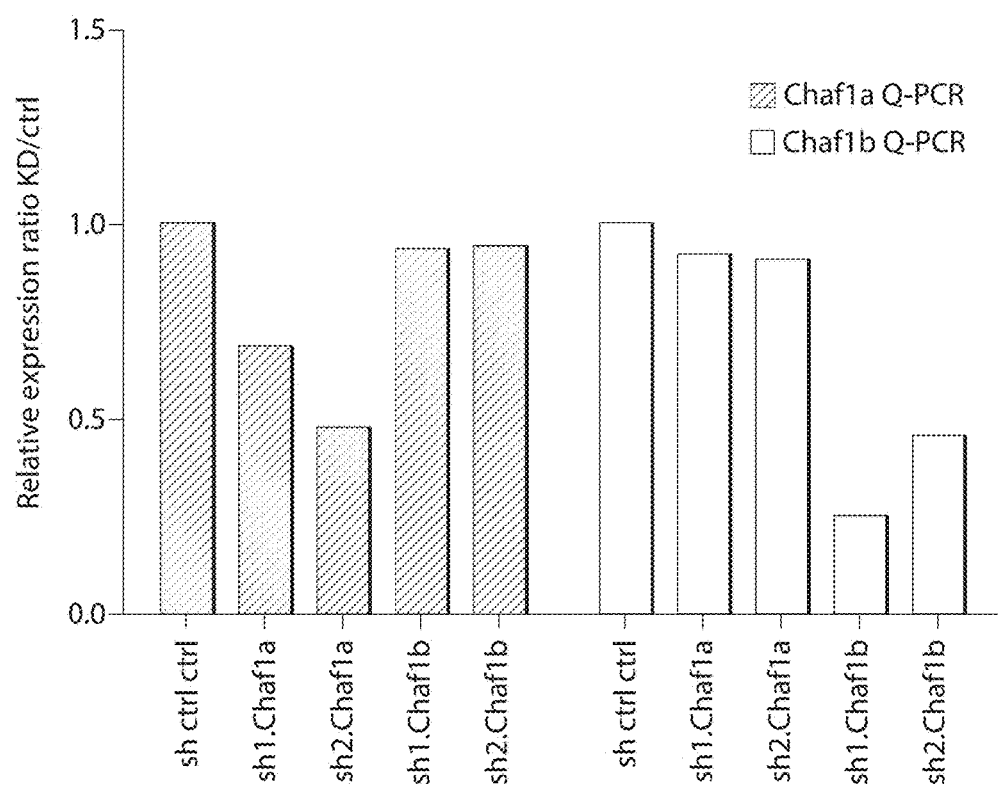
Figure 17A:
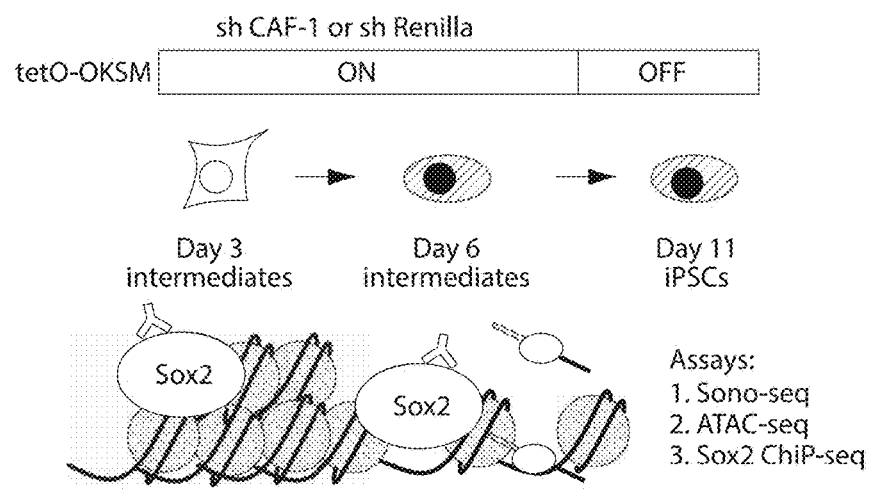
FIGS. 17A-17C.
Figure 17B:
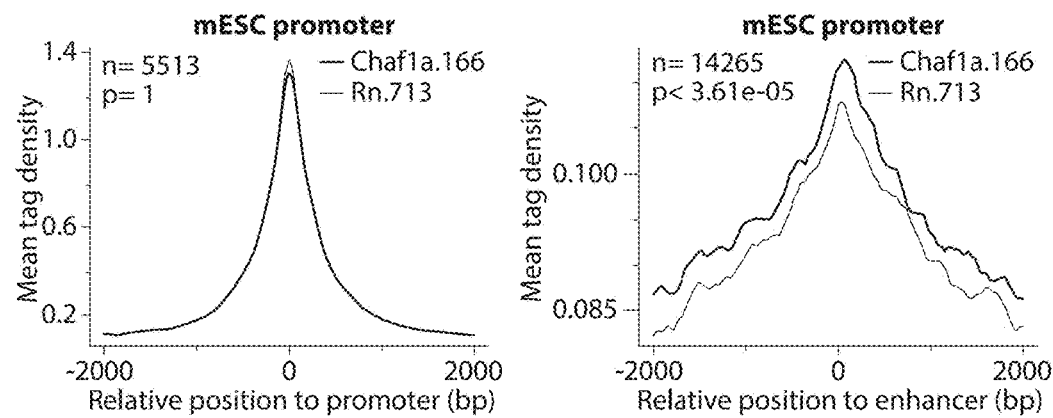
Figure 17C:
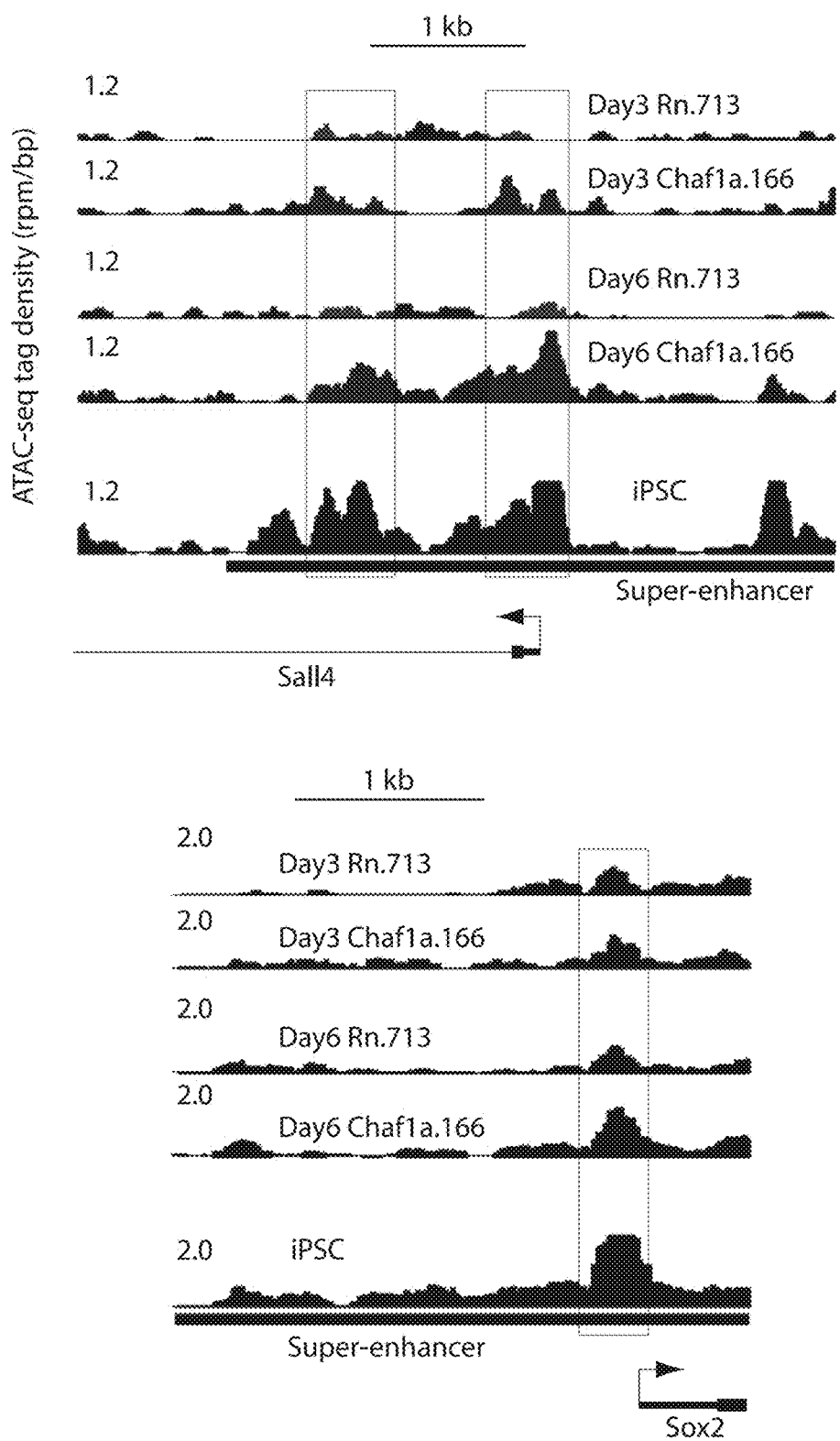

The screen identified shRNAs that strongly and consistently promoted iPSC formation. The most prominent hits that emerged from the screen were Chaf1a and Chaf1b, two subunits of the chromatin assembly factor complex CAF-1. Among the 22 shRNAs that enhanced iPSC formation more than four-fold in the arrayed screen, the inventors identified six shRNAs targeting Chaf1a or Chaf1b (three shRNAs each) including the three top-scoring shRNAs overall (FIG. 10B, 11A). Importantly, all tested top-scoring shRNAs targeting Chaf1a and Chaf1b reduced the expression of their predicted target genes (FIGS. 15A, 15B).

Suppression of CAF-1 Accelerates iPSC Formation

Figure 11B:
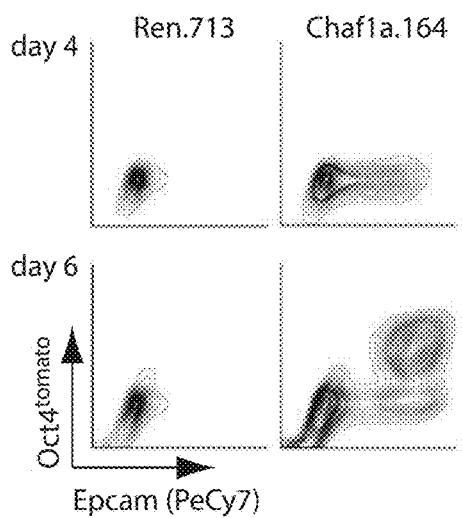

To gain insights into the dynamics of reprogramming in the absence of the identified chromatin barriers, the inventors followed the emergence of Epcam+ (early programming marker) and Oct4-tomato (late reprogramming marker) cells over time. This showed that Chaf1a suppression increased the fraction of both Epcam+ and Oct4-tomato+ cells at day four and six of reprogramming (FIG. 11B).

Figure 11C:
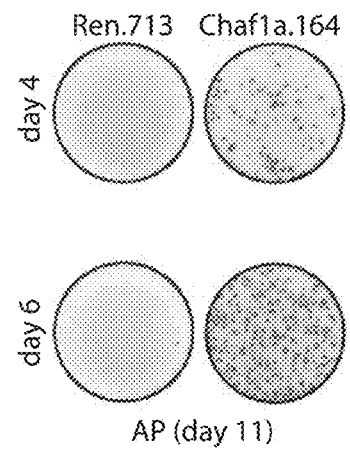

To complement these reporter and marker-based assays with a functional readout, the inventors examined the ability of candidate hairpins to facilitate transgene-independent clonal growth, a hallmark of authentic iPSCs. Suppression of Chaf1a indeed gave rise to transgene-independent AP+ cells after as little as four days of OSKM expression when no iPSCs were yet detectable in control shRNA-treated cells (FIG. 11C). Based on the identification of Chaf1a and Chaf1b as the top hits in two independent chromatin-focused reprogramming screens and their dramatic effects on both the dynamics and efficiency of iPSC formation, further analyses were focused on these two components of the CAF-1 complex.

It was ensured that suppression of CAF-1 subunits does not significantly influence expression of the Col1a1::tetOP-OKSM; R26-M2rtTA system at the RNA or protein level, ruling out the possibility that the observed phenotype is due to direct modulation of the reprogramming transgenes. Moreover, the reprogramming increase elicited by Chaf1b shRNAs could be rescued by overexpression of an shRNA-resistant version of human CHAF1B cDNA, demonstrating specificity of the effect. Lastly, knockdown of either CAF-1 subunit did not increase cell proliferation rates in the presence of OKSM induction, thus excluding that the dramatic increase in Oct4-GFP+ cells upon CAF-1 suppression is simply due to an expansion of reprogrammed cells or a loss of unreprogrammed cells.

Reprogramming Phenotype Depends on Optimal CAF-1 and OKSM Dose

Figure 12B:
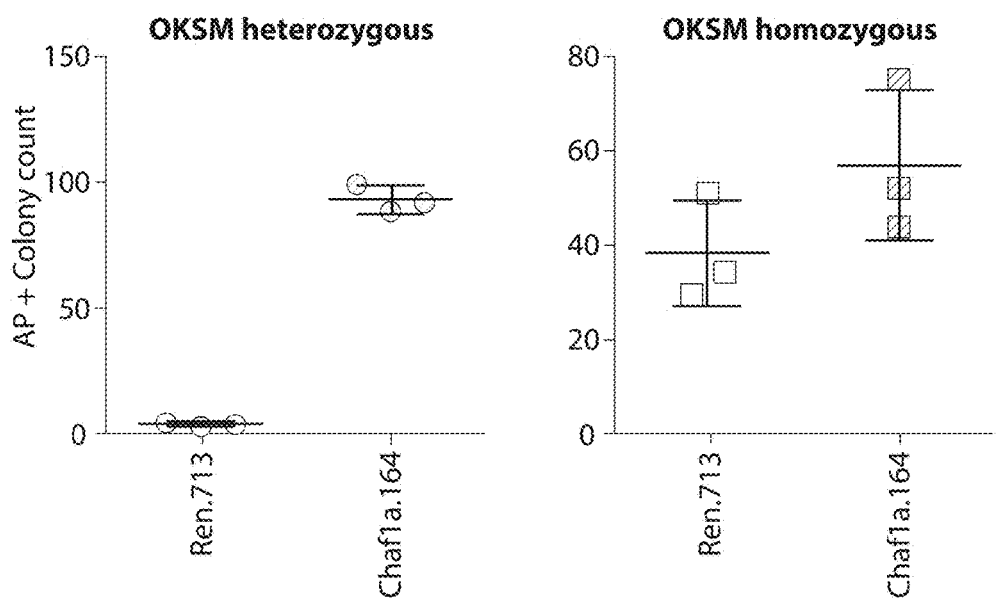
Figure 12C:
Figure 12D:
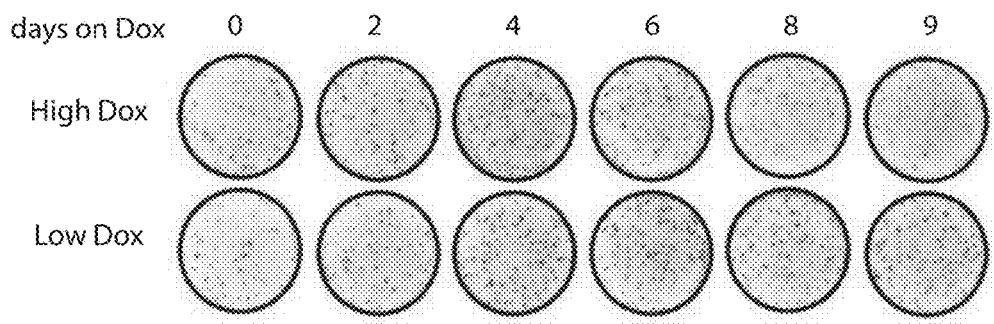
Figure 12E:
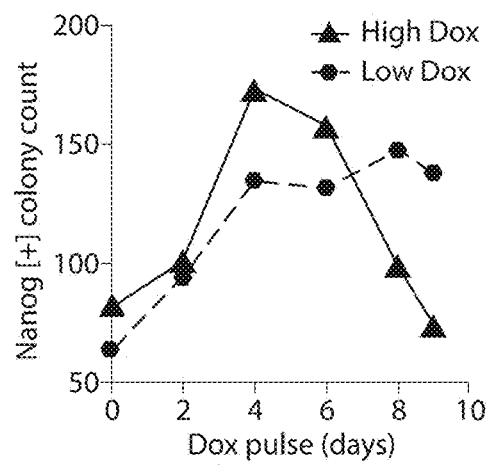

To determine whether CAF-1's effect on reprogramming depends on OKSM expression levels, iPSC formation efficiencies between reprogrammable MEFs carrying either one or two copies of the Col1a1::tetOP-OKSM and R26-M2rtTA alleles were compared; it was previously shown that increasing the dose of OKSM and M2-rtTA using this transgenic system profoundly influences reprogramming efficiency and speed[6,16]. While CAF-1 suppression in heterozygous MEFs increased iPSC formation by orders of magnitude, CAF-1 suppression in homozygous MEFs resulted in a more modest increase in iPSC numbers (FIG. 12A, 12B). Consistently, it was observed that CAF-1 knockdown had a much stronger effect on reprogramming efficiency when infecting MEFs with viral vectors achieving either temporally restricted or moderate OKSM expression compared to vectors achieving high OKSM expression levels over prolonged periods of time Enhanced iPSC formation upon CAF-1 knockdown was further observed with an independent transgenic reprogramming system producing OKSM at different stoichiometries compared to our Col1a1::tetOP-OKSM cassette[30]. These results show that the reprogramming phenotype upon CAF-1 suppression is influenced by both the levels and the duration of OKSM expression.

CAF-1 is essential for embryonic growth and the viability of cultured cells[27-29,31]. In line with this observation, it was found that the top-scoring shRNAs targeting CAF-1 components compromised the growth of NIH3T3 cells in the absence of OKSM expression. To test whether the duration and degree of CAF-1 suppression also affects reprogramming efficiency, transgenic MEFs carrying a dox-inducible Chaf1a shRNA linked to an RFP reporter in the Col1a1 locus were generated. When exposing these cells to either low or high concentrations of dox, a concomitant change in RFP reporter signal and Chaf1a protein levels (data not shown) was observed. Infection of transgenic MEFs with a constitutive lentiviral vector expressing OKSM in the presence of low doses of dox for 2, 4, 6, 8 or 9 days resulted in a progressive increase in the formation of Nanog+ iPSC colonies, which plateaued by day 6. In contrast, exposure of replicate cultures to high doses of dox increased reprogramming efficiency until day 4 but decreased iPSC colony numbers thereafter. Collectively, these data indicate that enhanced reprogramming is also dependent on CAF-1 dose, with early CAF-1 suppression being beneficial but long term, potent suppression being detrimental to iPSC derivation.

Figure 13A:
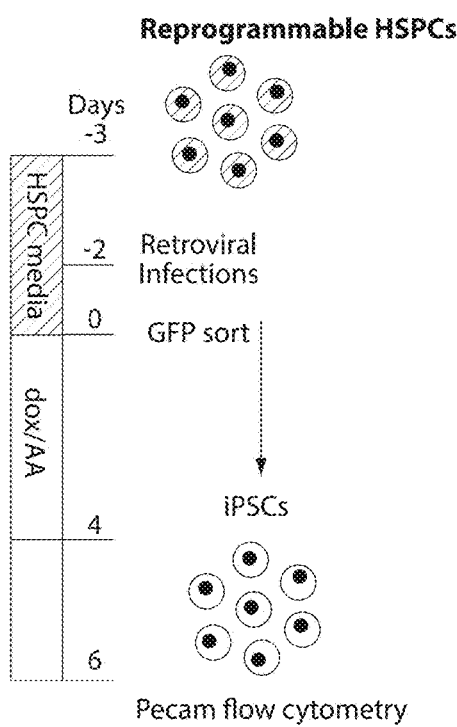
Figure 13B:
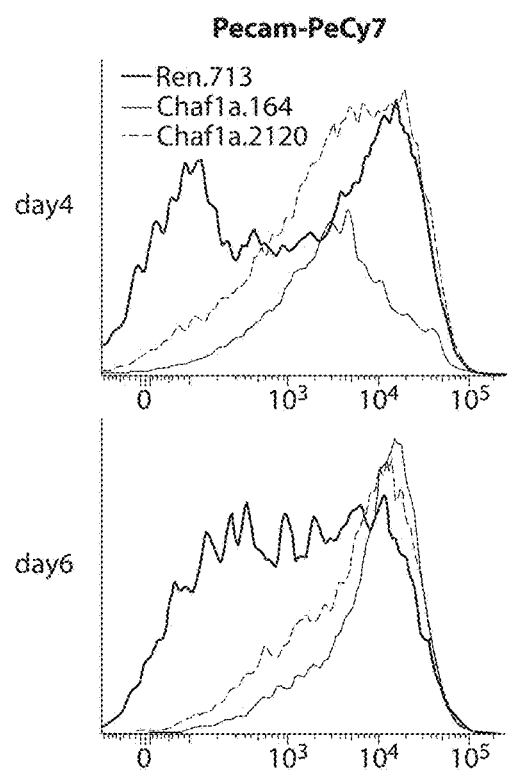

CAF-1 Depletion Enhances Reprogramming and Direct Lineage Conversion of Different Cell Types To investigate whether CAF-1 acts as a gatekeeper of cellular identity across different cell types, the inventors expanded their analysis from fibroblasts to blood progenitors. To this end, the inventors tested the effect of Chaf1a knockdown on the reprogramming potential of hematopoietic stem and progenitors cells (HSPCs) isolated from fetal livers of reprogrammable mice (FIG. 13A). The inventors monitored expression of the surface molecule Pecam over time, which coincides with activation of the Oct4-GFP reporter during reprogramming (10). After four days of OKSM induction, Pecam expression was detectable in 56% of control HSPCs, while Chaf1a suppression by two independent shRNAs enhanced this fraction to over 90% (FIG. 13B, 13C). By day six, essentially all Chaf1a shRNA treated cells (97%) had completed reprogramming as judged by Pecam surface expression, whereas only 76% of control cells had acquired a Pecam+ iPSC-like state. Consistently, suppression of Chaf1a gave rise to more transgene-independent colonies compared to controls at each examined time point. Hence, CAF-1 also functions as a barrier to iPSC formation in a cell type that is less differentiated and intrinsically more amenable to reprogramming compared to MEFs.

Figure 13F:
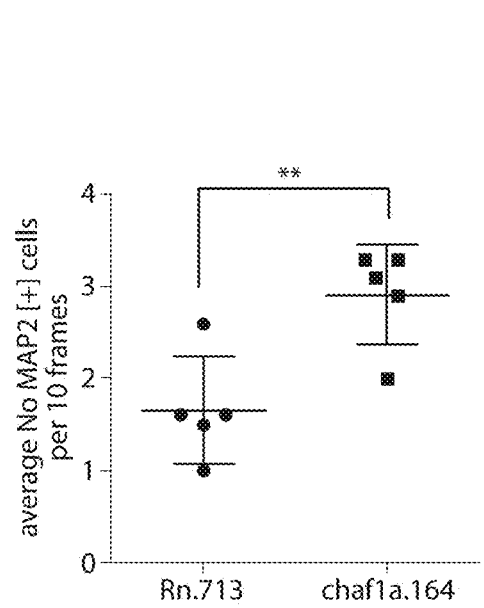

To assess whether CAF-1 stabilizes somatic cell identity in cell fate-conversion systems other than OKSM-mediated reprogramming, the inventors first examined the transdifferentiation of fibroblasts into induced neuronal (iN) cells upon overexpression of the transcription factor Ascl1 in MEFs (40). The inventors transduced transgenic MEFs harboring dox-inducible shRNAs targeting Renilla luciferase or Chaf1a with a dox-inducible Ascl1-expressing lentivirus and measured iN formation at day 13. CAF-1 knockdown consistently resulted in a two-fold increase (P=0.003) in the number of Map2+ neurons in four independent experiments (FIGS. 13E, 13F).

Figure 13G:
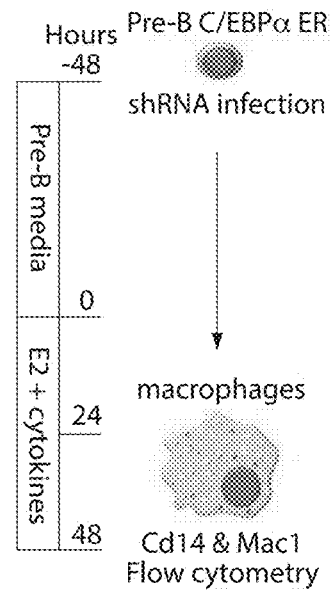
Figure 13H:
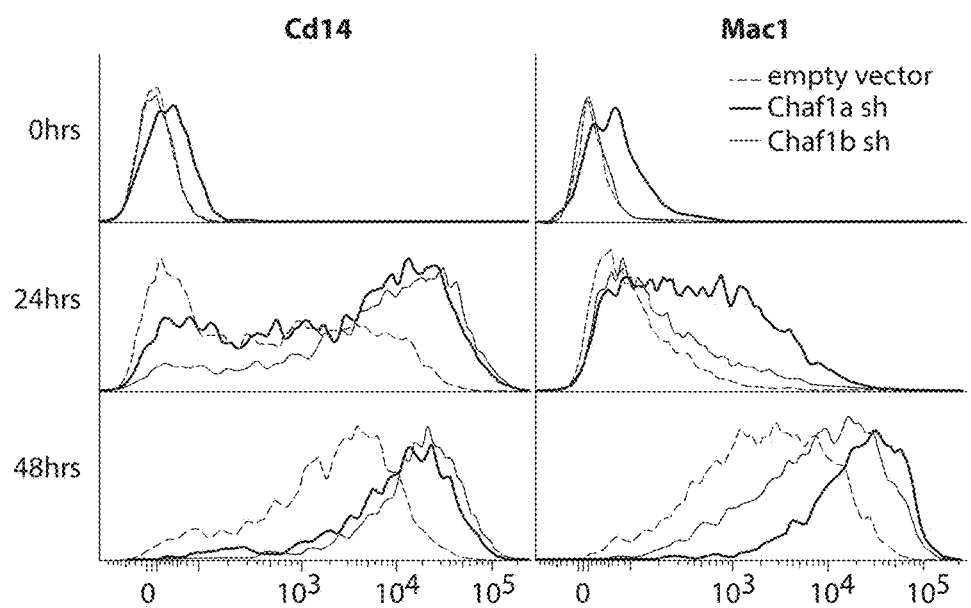
Figure 13I:
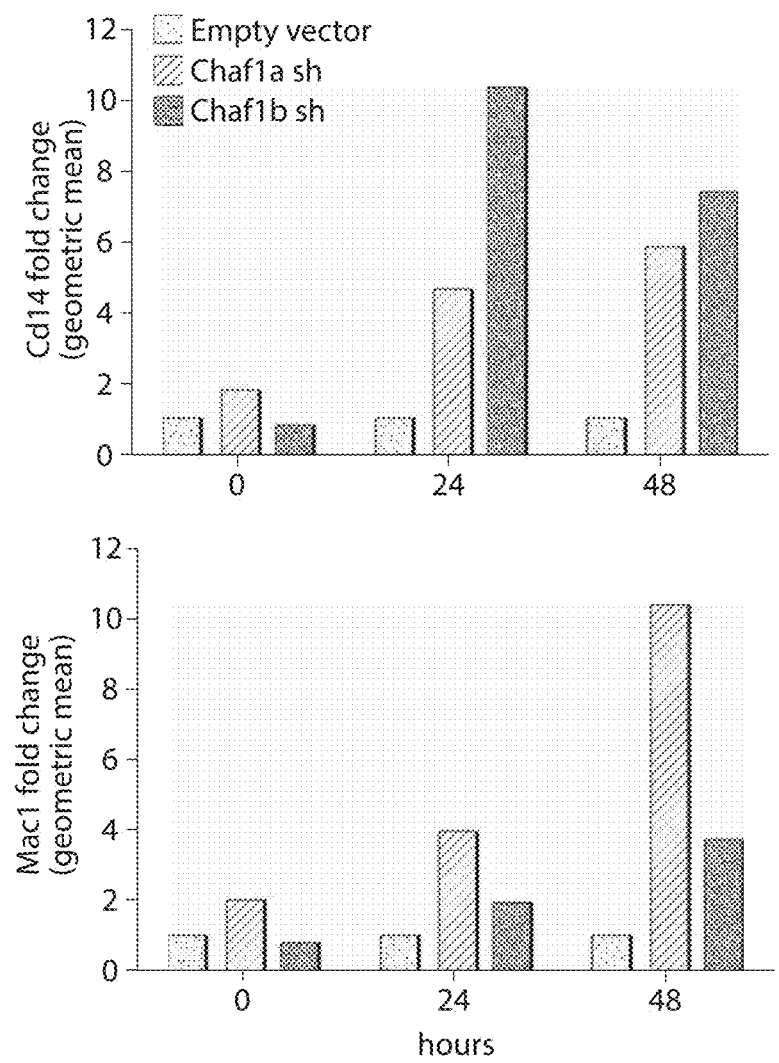

The inventors next tested the effect of CAF-1 suppression during the conversion of pre-B cells into macrophages upon overexpression of the myeloid transcription factor C/EBPα (FIG. 13G). Exposure of a C/EBPα-inducible pre-B cell line to estradiol reportedly triggers conversion into macrophages within 48 hours at 100% efficiency (41). Remarkably, knockdown of CAF-1 in this cell line resulted in an up to five-fold increase in the expression of the myeloid markers Cd14 and Mac1 after as little as 24 hours of estradiol treatment (FIG. 13H, 13I). Although the fractions of Cd14+ and Mac1+ cells were comparable between CAF-1 shRNA and control shRNA conditions at 48 hours, the expression levels of both differentiation markers were noticeably higher in CAF-1 depleted cells (FIG. 13H). Taken together, these data demonstrate that CAF-1 suppression not only enhances the induction of pluripotency from different cell types but also facilitates cellular transdifferentiation, indicating that reduced expression of CAF-1 generally promotes cellular plasticity during transcription factor-induced cell fate conversions.

Depletion of CAF-1 Promotes Chromatin Accessibility at Enhancer Elements and Facilitates Transcription Factor Binding Since CAF-1 functions as a histone chaperone that assembles nascent nucleosomes during DNA replication (42), it was reasoned that its reduced levels may result in a more accessible chromatin structure and thus facilitate transcription factor binding to their target loci. To interrogate possible differences in chromatin structure between CAF-1 depleted and control cells undergoing reprogramming, the inventors first performed SONO-Seq (43) analysis, which allows mapping of accessible chromatin regions due to their increased susceptibility to sonication. The inventors analyzed bulk cultures expressing OKSM for three days when no stable iPSCs are yet present. Given the importance of regulatory elements in defining cell identity (44), the study focused analysis on all annotated ESC-specific promoter and enhancer regions, as defined by recent ChIP-Seq analyses of post-translational histone modifications and p300 occupancy (45). Notably, while promoter elements showed no discernible difference in accessibility (P value=0.51), the inventors observed a significant enrichment of SONO-seq signal at ESC-specific enhancer elements in CAF-1 depleted cells at day three of OKSM expression (value $<2.64 \times 10^{-12}$). This observation indicates that CAF-1 suppression results in a more accessible local chromatin environment over ESC-specific enhancer elements early in reprogramming.

To validate these observations and generate a higher resolution map of chromatin accessibility in early reprogramming intermediates, the inventors performed an assay for transposase accessible chromatin using sequencing (ATAC-seq), which detects integrations of the Tn5-tagged transposase in open chromatin regions (46). In agreement with the SONO-seq data, ATAC-Seq analysis of early reprogramming intermediates show a more accessible chromatin configuration at ESC-specific enhancers upon CAF-1 depletion compared to controls (P value $<3.61 \times 10^{-5}$). The inventors next interrogated "super-enhancers", a recently described class of major lineage-specific regulatory elements in ESCs and other cell types (47-49). CAF-1 knockdown caused a significant increase in chromatin accessibility when considering all 231 reported ESC-specific super-enhancers compared to controls at day three of iPSC formation (P value $<1.28 \times 10^{-5}$). This difference became much more pronounced at day six of reprogramming, consistent with transitioning of the cells towards a pluripotent state.

When focusing on individual super-enhancers, it was observed that some loci (e.g., Sox2 and Sall4; 42 super-enhancers in total) but not others were significantly more accessible by ATAC-seq analysis in CAF-1 depleted cells compared to controls. Taken together, these results show that CAF-1 suppression facilitates a more accessible local chromatin structure at pluripotency-specific enhancer elements, including super-enhancers. Lastly, the inventors performed ChIP-Seq analysis for Sox2 at day three of OKSM expression in order to test the hypothesis that increased chromatin accessibility at enhancer elements influences reprogramming factor binding. Indeed, the inventors detected a significant increase in Sox2 binding to ESC-specific regulatory elements in CAF-1 knockdown cells compared to controls (FIG. 13C; P value $<2.2e^{-16}$). While the majority of Sox2 binding sites (around 90%) were shared between CAF-1 knockdown and control cells, roughly 10% were significantly enriched in cells expressing either CAF-1 shRNA (1,329 peaks) or Renilla shRNA (1,806 peaks) (FIG. 13D, left panel). Remarkably, binding sites unique to CAF-1 depleted cells were strongly enriched for ESC-specific Sox2 targets (50) relative to control cells (FIG. 13D, right panel). Consistently, ESC-specific super-enhancer elements were three-fold more abundant among the unique Sox2 sites in CAF-1 knockdown cells compared to controls (15 vs. 5). Of the 15 Sox2-bound super-enhancers unique to CAF-1 knockdown cells, seven (47%) also showed a more accessible chromatin structure by ATAC-Seq analysis (e.g., Sall1 and Mycn loci; FIG. 13E). Collectively, these results indicate that loss of CAF-1 contributes to reprogramming, at least in part, by increasing chromatin accessibility at pluripotency-specific enhancer elements and by promoting binding of reprogramming transcription factors such as Sox2 to its target genes.

Figure 14A:
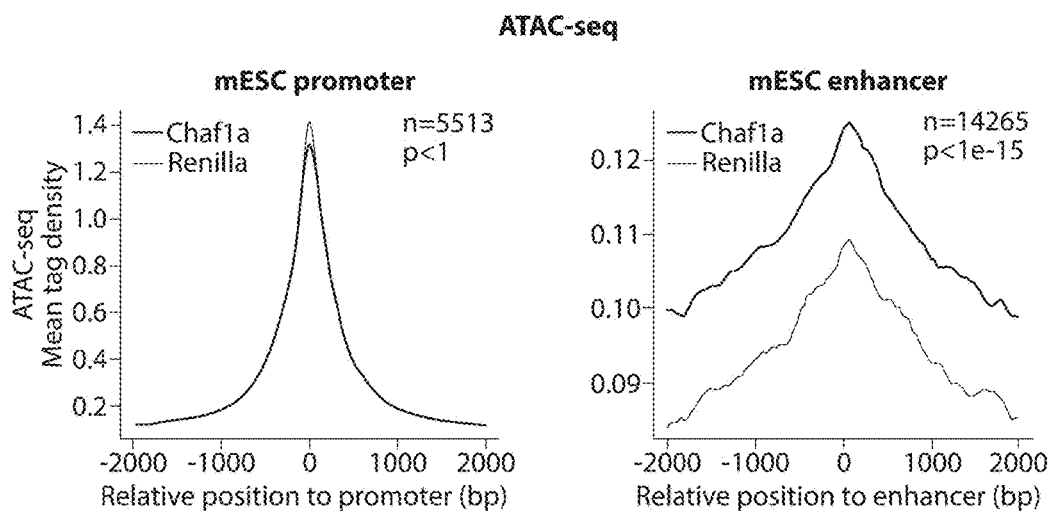
FIGS. 14A-14F.
Figure 14B:
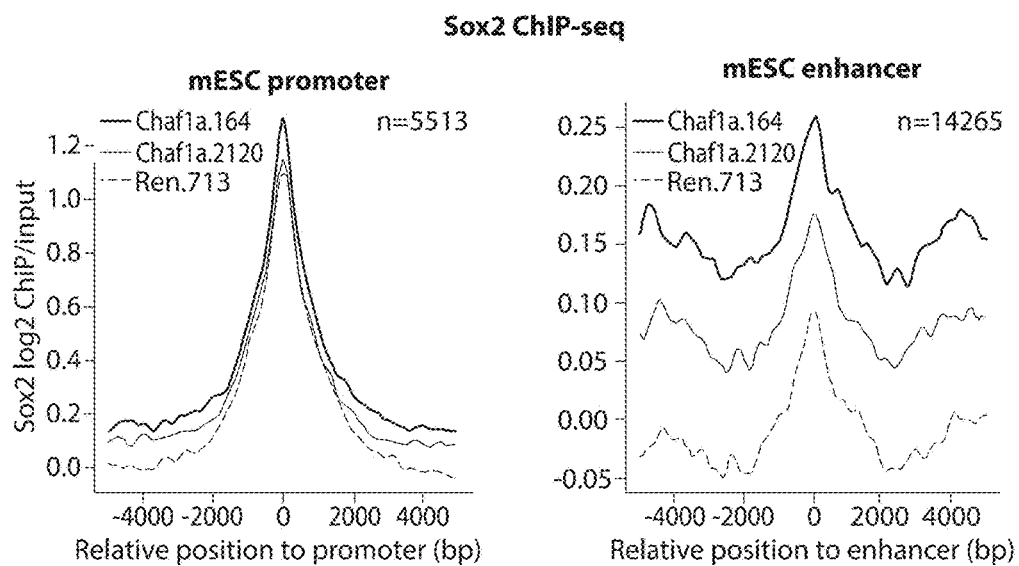
Figure 14C:
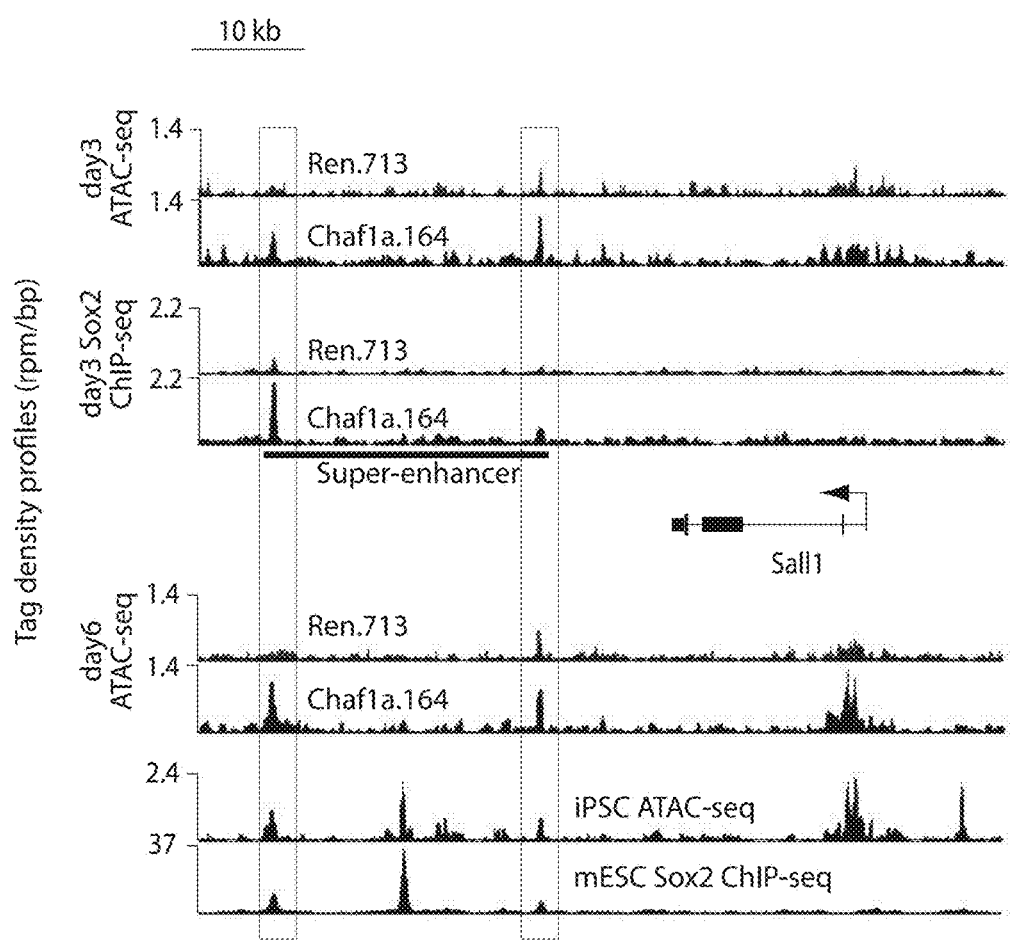
Figure 14D:
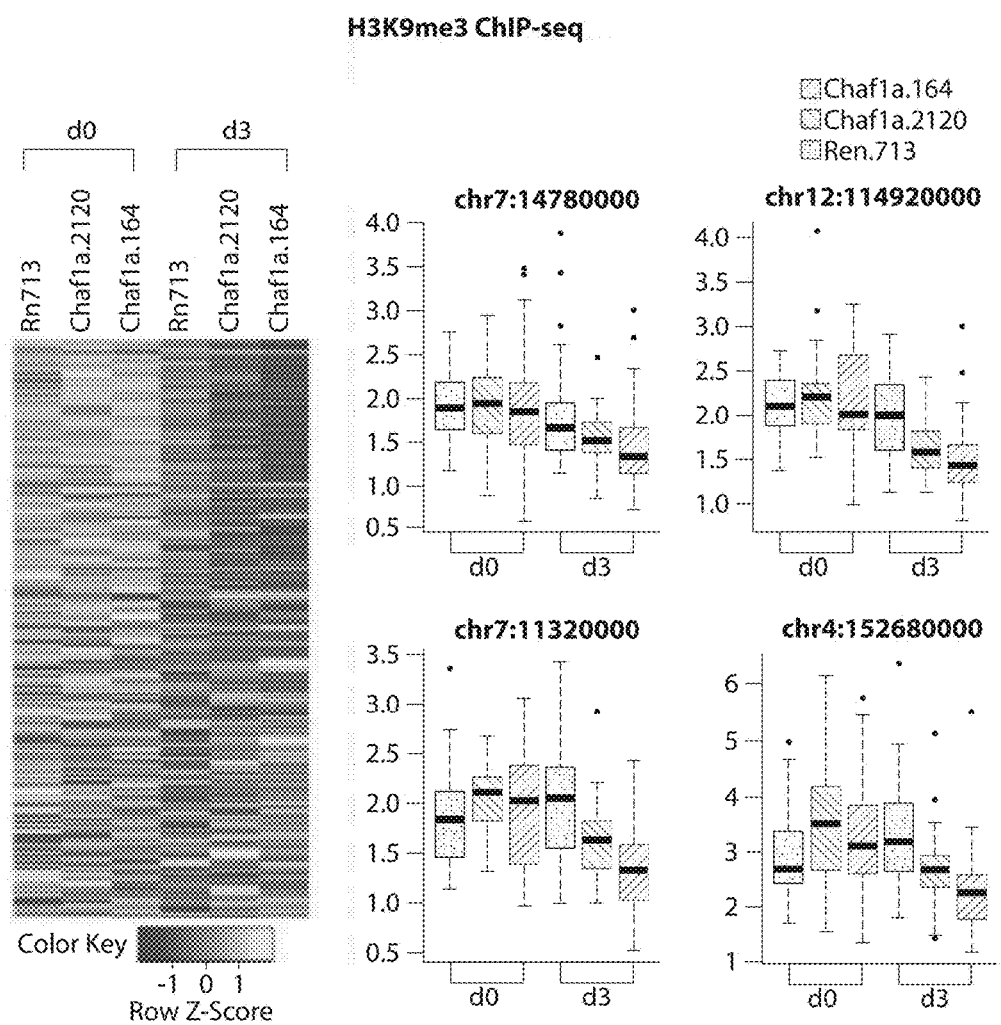
Figure 14E:
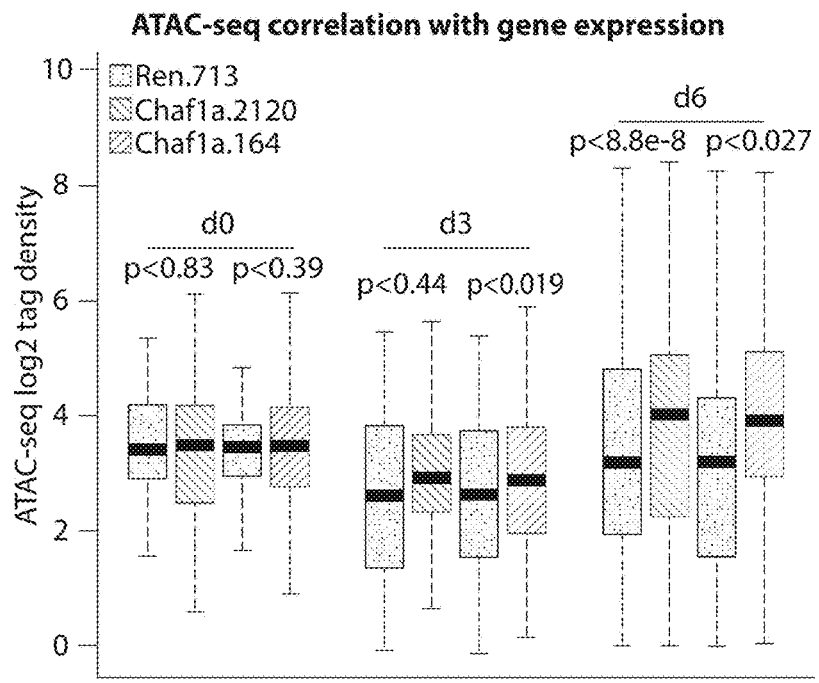
Figure 14F:
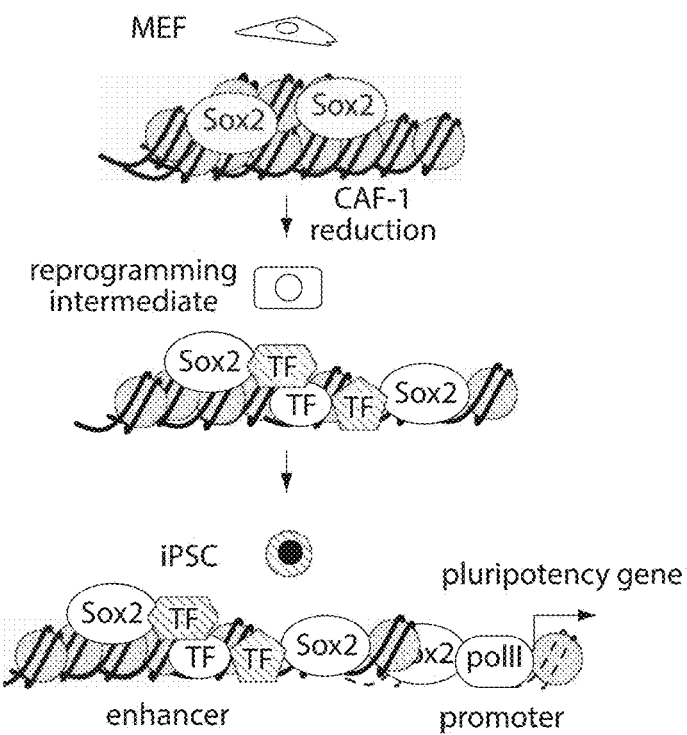

CAF-1 Suppression Alters Local Heterochromatin Domains and Primes Pluripotency Genes for Transcriptional Activation Considering that CAF-1 plays crucial roles not only in histone exchange but also heterochromatin maintenance[27,31,44], the global distribution of the heterochromatin mark H3K9me3 during reprogramming was examined. Significant differences were not detected in H3K9me3 levels across pluripotency-associated enhancers or transposable elements, which represent abundant and prototypical heterochromatic regions. Likewise, RNA-Seq analysis of the same intermediates failed to show differential expression of transposable elements between control and CAF-1 knockdown cells throughout the reprogramming time course. However, a local depletion of H3K9 trimethylation was detected at a subset of somatic heterochromatin areas termed "reprogramming-resistant regions", which have recently been linked to the low efficiency of somatic cell nuclear transfer[45] (FIG. 14D). It is inferred from these data that CAF-1 inhibition, in concert with OKSM expression, causes local changes in this key repressive histone modification, which may prime chromatin structure for efficient transcriptional activation.

Finally, it was investigated whether the observed CAF-1 shRNA-induced chromatin changes affect gene expression of associated genes. Of note, no major gene expression differences were detectable between control and CAF-1 shRNA samples at day three of reprogramming (data not shown). However, a subset of genes with increased chromatin accessibility at day three was transcriptionally upregulated by day six of reprogramming in CAF-1 knockdown intermediates (e.g., Utf1, Epcam, Nr0b1, Tdgf1, Sall4), supporting the view that CAF-1 suppression primes the genome for subsequent transcriptional activation. Altogether, these genome-wide assays support the conclusion that CAF-1 suppression, in collaboration with potent coactivators, facilitates the transcriptional activation of somatically silenced genes.

The inventors have combined a highly standardized iPSC reprogramming assay and two innovative shRNA screening approaches to systematically explore chromatin barriers to cellular reprogramming. Remarkably, the most potent roadblocks emerging from these screens was the nucleosome assembly complex CAF-1, which has not been identified in previous genome-wide or focused screens for iPSC reprogramming barriers (11, 13, 14, 16, 17). Of note, CAF-1 and several other roadblocks uncovered in our screens (e.g. Brd4, Dnmt1) are essential genes (51-56), that would not have been identified with alternative screening methods involving the complete and permanent ablation of gene function.

Together, these findings highlight the advantage of RNAi technology for generating hypomorphic states of gene function in order to dissect basic cellular processes with a comprehensive functional genetics approach.

In addition to identifying CAF-1 as the most prominent roadblock to iPSC formation in two independent screens, this study provides evidence that CAF-1 suppression facilitates transcription factor-driven cell fate changes in at least two additional systems: direct conversion of fibroblasts to neurons and B cells to macrophages. Consistent with the role of CAF-1 in replication-coupled nucleosome assembly, it was found that its suppression has a more pronounced effect on cellular plasticity in systems that involve multiple rounds of cell division (i.e., iPSC formation from MEFs) compared to those that require only 1-3 divisions (i.e., direct lineage conversion) or those that exhibit intrinsically high proliferation rates (i.e., iPSC induction from HSPCs). Based on these observations, it is tempting to speculate that a tolerable reduction in the expression of other components associated with the DNA replication machinery may also facilitate cell fate change. In support of this idea, hypomorphic alleles of the essential proliferating cell nuclear antigen (PCNA) gene, which acts as a scaffold for proteins involved in DNA replication, suppress position effect variegation in flies (57). The methyltransferase Dnmt1 represents another fork component that is involved in the maintenance of cell identity (3) and scores in the present screen as a chromatin barrier. Although knockdown or pharmacological inhibition of Dnmt1 also facilitates iPSC formation and transdifferentiation of MEFs into myogenic cells (12, 58, 59), the screens described herein indicate that interference with nucleosome assembly may represent a more potent and broadly applicable strategy to facilitate cell fate change.

Without wishing to be bound by theory, the inventors propose that CAF-1 contributes to the maintenance of somatic cell identity in replicative cells by safeguarding chromatin structure. According to this model, suppression of CAF-1 triggers dilution of newly assembled nucleosomes at key enhancer elements and loosening of chromatin structure in conjunction with forced expression of lineage-specifying transcription factors. These combined changes may generate an accessible chromatin landscape for efficient transcription factor binding and subsequent robust activation of key target genes. Other histone chaperones may compensate for the loss of CAF-1 during reprogramming.

Indeed, suppression of the CAF-1 subunit p60 in human cells triggers compensatory deposition of the histone variant H3.3 by the chaperone HIRA (60, 61). Of interest, H3.3 deposition on chromatin has recently been associated with enhanced reprogramming in the context of somatic cell nuclear transfer (62-64). Given that CAF-1 associates with regulators of heterochromatin, it will further be interesting to ascertain whether its suppression during iPSC formation also influences heterochromatin domains, which are thought to resist reprogramming (29-31,65).

The present study provides fundamental insight into chromatin-associated mechanisms regulating somatic cell identity, and indicates novel strategies for controlling cell fate transitions for therapeutic purposes. For example, the inventors anticipate that some of the chromatin barriers to iPSC formation identified here also contribute to normal development and tumorigenesis. Targeting of these chromatin factors in diseased or damaged tissues can thus help to eliminate aberrant cells or promote cellular regeneration, respectively. The dose dependency of the top hits indicates that one can accomplish this goal with inhibitors that trigger such cell fate changes in vitro or in vivo with low cellular toxicity.

METHODS AND MATERIALS

Cell Culture and Media

Packaging cells (Platinum-E™ Retroviral Packaging Cell Line) for producing Retrovirus were cultured in DMEM supplemented with 15% FBS, 100 U ml-1 penicillin, 100 μg ml-1 streptomycin, sodium pyruvate (1 mM) and L-glutamine (4 mM) at 37° C. with 5% $CO_2$. Mouse embryonic fibroblasts (MEF) were cultured in DMEM supplemented with 15% FBS, 100 U ml-1 penicillin, 100 μg ml-1 streptomycin, sodium pyruvate (1 mM), L-glutamine (4 mM), L-ascorbic acid (50 uM) at 37° C. with low oxygen (4.5% $O_2$). iPSCs were derived in DMEM supplemented with 15% FBS, 100 U ml-1 penicillin, 100 μg ml-1 streptomycin, sodium pyruvate (1 mM), L-glutamine (4 mM), 1000 U/ml LIF, 0.1 mM 2-mercaptoethanol, and 50 μg ml-1 ascorbic acid at 37° C. with 5% $CO_2$ and 4.5% $O_2$. iPSCs for blastocyst injection were cultured on feeders in DMEM supplemented with 13% Knockout Serum Replacement (Gibco™), 2% FBS, 100 U ml-1 penicillin, 100 μg ml-1 streptomycin, sodium pyruvate (1 mM), L-glutamine (4 mM), L-ascorbic acid (50 uM), 1000 U/ml LIF, beta mercaptoethanol, MEK inhibitor (1 μM) and GSK3 inhibitor (3 μM) at 37° C. with 5% $CO_2$. Conventional reprogramming media consisted of DMEM supplemented with 15% FBS, 100 U ml-1 penicillin, 100 μg ml-1 streptomycin, sodium pyruvate (1 mM), L-glutamine (4 mM), 1000 U/ml LIF, 0.1 mM 2-mercaptoethanol unless otherwise noted. For some experiments, media was supplemented with MEK inhibitor (1 μM), GSK3 inhibitor (3 μM), Dotl1 inhibitor (1 uM) or ascorbate (50 ug/ml).

Primary MEFs were derived from E13.5 embryos isolated from intercrosses between mice homozygous for Col1a1::tetOP-OKSM; Oct4-GFP and Rosa26 M2rtTA, respectively. Embryos were dissected carefully excluding internal organs, heads, limbs and tails and only carcasses were used for MEF derivation. Tissues were chopped into small clumps using scalpels, trypsinized and cultured in MEF medium at low $O_2$ (4%). MEFs were frozen at passage 0 upon derivation and used at passage 1 for all downstream transduction and reprogramming experiments. All MEFs were cultured at low $O_2$ (4%) and supplemented with ascorbate to prevent replicative senescence before OKSM overexpression.

Reprogramming experiments were initiated at low oxygen levels during dox induction and completed at normal oxygen levels (20%) for mir-E experiments. Mir-30 assays were performed continuously at normal oxygen levels. HSPCs were isolated from fetal livers of the same mid-gestation reprogrammable transgenic embryos used for MEFs derivation, dissociated by vigorous pipetting with a 1 ml tip, filtered using 35 μm nylon mesh, followed by red blood cell lysis and cultured in RPMI/FBS media supplemented with stem cell factor (SCF), Il3 and Il6 cytokines and transduced as indicated in the schematic (FIG. 13A).

Arrayed shRNA Library and Screen

Single shRNA clones were picked from the master library at CSHL, arrayed in 12×96 well plates and sequence-verified individually using miR30 backbone primers. An additional 200 unmatched clones were re-picked and sequenced to allow maximum coverage of the library. Double transgenic reprogrammable MEFs carrying the OKSM inducible cassette and constitutive rtTA (Col1a1::tetOP-OKSM; R26-M2rtTA) were seeded at 10e4 cells per well in 96 well plates in duplicates and infected with the corresponding retroviral virus particles freshly produced and filtered in 96 well format.

48 hrs post transduction, MEFs from each row were trypsinized and transposed into 6 well dished coated with 0.2% gelatin in standard reprogramming media supplemented with dox and G418 at 0.2 mg/ml for the first six days of OKSM expression. Dox was withdrawn at day 12, allowing stable iPSCs to form. iPSC colonies were then stained for alkaline phosphatase expression using Vector Red™ Alkaline Phosphatase Substrate Kit (VectorLabs™) according to the supplier's protocol. Plates were scanned with a Perfection V500 Photo scanner (Epson™) and automated counting was performed using a proprietary image-processing algorithm by Nikon™. Reprogramming efficiency was calculated based on infection efficiency and normalized to infections with control shRNAs targeting the luciferase Renilla transcript.

Retrovirus Production, Transduction of MEFs and Derivation of iPSCs

Retroviral constructs were introduced into Platinum-E™ Retroviral Packaging cells using calcium phosphate transfection or lipofection as previously described (Zuber, J. et al. (2011) Nature Biotechnology 29:79-83). shRNAs were transduced into primary MEFs carrying the Col1a1::tetOP-OKSM and R26-M2rtTA alleles as well as a Pou5f1-EGFP reporter at single copies. For transduction, 180,000 cells were plated per well of a 6-well dish; all vectors were transduced in biological triplicate. After 36 hrs, transduced cells were selected with 0.5 mg ml-1 G418 for 3 days and 0.25 mg ml-1 G418 for an additional 3 days. 3 days after shRNA transduction, infected cells were washed with PBS (1×) and trypsinized with Trypsin-EDTA (1×) and 20,000 cells were plated into a 6-well. OSKM expression was induced for 7 days and cells were cultured in DMEM supplemented with 15% FBS, 100 U ml-1 penicillin, 100 μg ml-1 streptomycin, sodium pyruvate (1 mM), L-glutamine (4 mM), 1000 U/ml LIF, 0.1 mM 2-Mercaptoethanol, 50 μg ml-1 sodium ascorbate and 1 μg ml-1 doxycycline at 37° C. with lox oxygen (4.5% $O_2$) and 5% $CO_2$. After 7 days of OSKM expression, cells were cultured for an additional 4 days without doxycycline to withdraw OSKM transgene expression at 37° C. with 5% $CO_2$, ambient oxygen. Following trypsinization, cells were analyzed for Oct4-GFP expression using a FACS BD LSRFortessa™ (BD Biosciences™), data were analyzed using FlowJo™.

Phenotypic Characterization of iPSCs

Alkaline phosphatase activity was measured using an enzymatic assay for alkaline phosphatase (VECTOR Red™ Alkaline Phosphatase (AP) Substrate Kit) according to the manufacturer's protocol.

Flow Cytometry Analysis of Reprogramming Intermediates

Reprogramming intermediates and Pecam stains were performed as previously described[6]. All samples were analyzed on a MACSQuant™ fluorescence cytometer (Miltenyi™).

Transdifferentiation Assays

Induced neurons were generated as described in the experimental scheme (FIG. 13D). CAF-1 or Renilla RNAi inducible transgenic MEFs were transduced with Ascl1-inducible lentivirus, exposed to dox 24 hrs post induction, cultured in MEF media for the first 48 hrs and switched to serum-free neuronal media (N3B27) supplemented with dox for an additional 11 days. Cultures were fixed and stained for MAP2 as previously described[33]. Pre-B cells (C10 line) were cultured in RPMI Medium, 10% charcoal stripped FBS (Invitrogen™), 2 mM L-Glutamine, 100 unit/ml penicillin, 1000 ug/ml streptomycin), 55 uM beta-mercaptoethanol. Pre-B cells were transduced 48 hrs before initiating macrophage transdifferentiation with estradiol (E2). For transdifferentiation assays, cultures were transduced with lentiviral pLKO vectors obtained from the Broad Institute's RNAi consortium (empty vector "null control" or vector carrying stem-loop shRNAs targeting Chaf1a and Chaf1b subunits). Following selection of transduced cells with puromycin, cells were seeded at 1e6 cells/ml and supplemented with E2 and macrophage cytokines (IL3 and CSF) as previously described[34]. All time points were analyzed for Cd14 and Mac1 expression by flow cytometry on the same day.

Quantitative RT-PCR

RNA was extracted (Qiagen RNeasy™ mini kit) and reverse transcribed (GE Illustra™ ready-to-go RT-PCR beads) according to the supplier's instruction. Quantitative PCR was performed using SybrGreen™ mix and a BIO-RAD™ CFX connect cycler. Primers used were:

```
b-Act-F      GCTGTATTCCCCTCCATCGTG;         (SEQ ID NO: 18)

b-Act-R      CACGGTTGGCCTTAGGGTTCAG;        (SEQ ID NO: 19)

Chaf1b-R     GGCTCCTTGCTGTCATTCATCTTCCAC;   (SEQ ID NO: 20)

Chaf1b-F     CACCGCCGTCAGGATCTGGAAGTTGG;    (SEQ ID NO: 21)

Chaf1a-R     GTGTCTTCCTCAACTTTCTCCTTGG;     (SEQ ID NO: 22)

Chaf1a-F     CGCGGACAGCCGCGGCCGTGGATTGC.    (SEQ ID NO: 23)
```

SDS-PAGE and Western Blot Analysis

Whole-cell lysates from reprogramming intermediates were run on 4-20% gradient SDS-polyacrylamide gels and transferred to nitrocellulose membrane (Bio-Rad™) by standard methods. Membranes were blocked for 1 h in 5% non-fat dry milk in 1×TBS with 0.05% Tween-20 (TBST), rinsed, and incubated with primary antibody diluted in 3% BSA in TBST overnight at 4° C. The following primary antibodies were used: anti-Chaf1a (sc-10206, Santa Cruz™), anti-Chaf1b (sc-393662, Santa Cruz™), anti-TBP (ab818, Abcam™), HRP conjugate anti actin (AC-15, Sigma™) Blots were washed in TBST, incubated with HRP-conjugated secondary antibodies for semi-quantitative Western blot analysis and IR dye 800CW or IR dye 680RD for quantitative westerns, as indicated. Secondary antibodies for both methods were incubated in 5% milk in TBST for 1 hour at room temperature (except for anti-β-ACTIN-Peroxidase antibody, which was incubated for 15 min), and washed again. HRP signal was detected by Enhanced ChemiLuminescence™ (Perkin Elmer™) Fluorescent infrared signal was detected using LI-COR Odyssey™ imaging system.

ATAC-Seq Chromatin Assay

To generate ATAC-seq libraries, 50,000 cells were used and libraries were constructed as previously described[39]. Briefly, cells were washed in PBS twice, counted and nuclei were isolated from 100,000 cells using 100 ul hypotonic buffer (10 mM Tris pH 7.4, 10 mM NaCl, 3 mM MgCl2, 0.1% NP40) to generate two independent transposition reactions. Nuclei were split in half and treated with 2.5 µL Tn5 Transposase (Illumina™) for 30 min at 37° C. DNA from transposed nuclei was then isolated and PCR-amplified using barcoded Nextera™ primers (Illumina™). Library QC was carried out using high sensitivity DNA bioanalyzer assay and qubit measurement and sequenced using paired end sequencing (PE50) on Illumina™ Hi-Seq 2500 platform.

Sono-Seq and ChIP-Seq Chromatin Assays

For all ChIP experiments, 10e7 reprogramming intermediates were collected per library. Chromatin precipitation assays were performed as previously described (Bernstein, B. et al. (2005) Cell 120:169-181) using goat polyclonal anti-Sox2 antibody (AF2018, R&D™). Briefly, cells were cross-linked on plate in 1% methanol-free formaldehyde and snap-frozen in liquid nitrogen until processed.

Nuclei were isolated using 1 ml of cell lysis buffer (20 mM Tris pH8, 85 mM KCL, 0.5% NP40 and 1×HALT protease inhibitor cocktail), resuspended in nuclear lysis buffer (10 mM Tris-HCL pH7.5, 1% NP40, 0.5% Na deoxycholate, 0.1% SDS, 1×HALT protease inhibitor cocktail) and sonicated using optimized pulses of a Branson sonifier (1 min ON/OFF pulses for 5 cycles) for ChIP-seq libraries and S220 Covaris™ sonicator (Settings: duty cycle 5%, intensity 6, cycles/burst 200, pulse length 60 s, 20 cycles, 8° C.) for sono-seq input preparations. Sonications were verified for both methods using the 2100 Bioanalyzer™. Immunoprecipitations were carried out by first adjusting salt concentration in sheared chromatin to 167 mM NaCl and adding antibodies (bug of Sox2 antibody) and incubated for 3-4 hrs at 4 C. 50 µl Protein G Dynabeads (Invitrogen™) were prepared for each IP reaction by washing 2-3 times in ChIP dilution buffer (16.7 mM Tris-HCl pH 8.1, 167 mM NaCl, 0.01% SDS, 1.1% Triton X-100, 1.2 mM EDTA) and added for an additional hour to pull down bound chromatin. Bead complexes were then washed 6 times in RIPA buffer (20 mM Tris-HCL pH8.1, 1 mM EDTA, 140 mM NaCl, 1% Triton X-100, 0.1% SDS, 0.1% Na deoxycholate), then two times with RIPA with high salt concentration (500 mM), then 2 washes in LiCL buffer (10 mM tris-HCL pH 8.1, 1 mM EDTA, 1% DOC, 1% NP40, 250 mM LiCL) and 2 final washes in TE buffer. Complexes were then eluted and reverse cross-linked in 50 ul ChIP elution buffer (10 mM Tris-HCL pH8, 5 mM EDTA, 300 mM NaCl, 01% SDS) and 8 ul of reverse crosslinking buffer (250 mM Tris-HCl pH 6.5, 1.25M NaCl, 62.5 mM EDTA, 5 mg/mL Proteinase K, 62.5 ug/mL RNAse A) by incubation at 65° C. for 6 h. DNA was isolated using Ampure™ SPRI beads and yield quantified using Qubit™ fluorometer. ChIP-seq libraries were constructed from 10 ng of immunoprecipitated DNA using the NEBNext™ ChIP-Seq Library Prep Reagent Set for Illumina™ (New England Biolabs™), following the supplier's protocol. Briefly, purified DNA was end-repaired and dA-tailed. Following subsequent ligation of sequencing adaptors, ligated DNA was size-selected to isolate fragments in the range of 300-550 bp in length using Egels. Adaptor-ligated fragments were enriched in a 14-cycle PCR using Illumina™ multiplexing primers. Libraries were purified, analyzed for correct size distribution using dsDNA High Sensitivity Chips on a 2100 Bioanalyzer™ (Agilent™), pooled and submitted for single-end 50 bp Illumina™ GAII high-throughput sequencing.

Sono-Seq Bioinformatics Analysis

The reads were aligned to mm9 using Bowtie with a unique mapping option (Langmead et al. (2009) Genome Biology 10:R25). The smoothed tag density profiles were generated using get.smoothed.tag.density function of the SPP R package with a 100-bp Gaussian kernel, 50-bp step and library size normalization (Kharchenko, P et al. (2008) Nature Biotechnology 26:1351-1359). The positions of promoters and enhancers in ESCs and MEFs were obtained from publicly available data set[38]. To access the significance of the difference in the enrichment values between CAF-1 and Renilla knockdown samples, a paired Wilcoxon rank sum test was used.

ATAC-Seq Bioinformatics Analysis

The reads were aligned to the mouse genome mm9 using BWA version 0.7.8 with -q 5-132-k 2 and paired option (Li and Durbin. (2009) Bioinformatics 25:1754-1760). Non-primary mapping, failed QC, duplicates and non-paired reads were filtered. Reads from different chromosomes and chrM were also filtered. Only uniquely mapped reads were used for the analysis. The read density profiles were generated using 150 bp window with a 20 bp step and were normalized by the library size. For the comparison between Chaf1a.166 mutant and Renilla mutant, the read density profiles were further normalized using the mean values of all annotated promoters from mm9. The positions of promoters and enhancers in mESC and MEF were obtained from publicly available data sets in Sono-seq analyses[38]. The coordinates of the metagene plot in super-enhancers were used from recently published datasets[42]. For each superenhancer region, the tag density signals were averaged into 101 bins, with the margin of 5 kb outside of super-enhancers. Significantly enriched regions were detected using Hotspot with FDR=0.01 74. The differential sites between CAF-1 KD and *Renilla* KD were identified using DiffBind with p=0.05 for the consensus ATAC-seq peaks (Ross-Innes et al (2012) *Nature* 481:389-393). DiffBind uses statistical routines developed in edgeR (Robinson, M D et al. (2010) *Bioinformatics* 26:139-140. A one-sided paired Wilcoxon rank sum test was used for the comparison in the enrichment values between CAF-1 KD and *Renilla* KD.

Sox2 ChIP-Seq Bioinformatics Analysis

The reads were aligned to mm9 using Bowtie with a unique mapping option (Langmead et al. (2009) *Genome Biology* 10:R25). The smoothed tag density profiles for Sox2 were generated using get.smoothed.tag.density function of the SPP R package with a 100-bp window, 50-bp step and library size normalization as in Sono-seq analyses. The log 2 fold enrichment profiles were generated using get.smoothed.enrichment.mle in SPP R package. The same coordinates of promoters and enhancers in mESC and MEF were used as in Sono-seq and ATAC-seq analyses. A paired Wilcoxon rank sum test was used for the comparison in the enrichment values between CAF-1 KD and *Renilla* KD for Sox2. For the peak comparison in Sox2 between CAF-1 KD and *Renilla* KD, first the reads were subsampled to make the sequencing depth the same from each condition as the number of peaks called tends to increase as sequencing depth is deeper. The significantly enriched peaks compared inputs were detected using SPP find.binding.positions function with e-value+10 (Kharchenko, P et al. (2008), supra). The overlapped peaks were compared with a margin of 200 bp distance. For the unique peaks, peaks which were present only from one condition (CAF-1 KD or *Renilla* KD) were first identified. For the peaks which were present from one condition, the enrichment values (input-subtracted tag counts) were compared between CAF-1 KD and *Renilla* KD. If the ratios between the enrichment values between conditions were >2 fold, the peaks were considered as "unique" for one of the conditions. mESC Sox2 data was used from publicly available data sets[43] and analyzed as described above.

H3K9Me3 ChIP-Seq Bioinformatics Analyses

ChIP sequencing data was mapped to the mouse genome (mm9) with Bowtie 0.12.7 allowing up to three mismatches, and retaining uniquely mapping reads. To assess H3K9me3 signal distribution genome-wide, we divided the genome in 5 Kb intervals, and for each interval, the ratio of RPM normalized signal in the IP and input samples was calculated. Intervals with less than 10 reads in the input samples (~10% of all) were excluded from further analyses due to low coverage. Intervals overlapping specific regions were extracted using the bedtools suite (Quinlan et al. (2010) *Bioinformatics* 26:841-842. RRR region annotations were obtained from Matoba et al[45], and signal across all included 5 Kb intervals was averaged.

For H3K9me3 enrichment over TE bodies, the mm10 genome version was used, as this release contains the most recent TE annotations. The genomic regions corresponding to TE families annotated in the mm10 RepeatMasker track in the UCSC genome browser were extracted, and the normalized read counts in IP to input samples were calculated for each family. Due to the repetitive nature of TEs, all results were further validated considering reads that map to multiple (up to 10000) positions in the genome, and scaling read counts by the number of valid alignments. This threshold for multiple mapping positions was chosen as it was previously shown to approximate results obtained allowing unlimited mapping positions, but at a significantly improved computation speed (Pezic et al. (2014) *Genes & Development* 28:1410-1428). In all analyses, signal estimates based on uniquely mapping reads, and based on reads mapping to multiple genomic positions, produced similar results.

RNA-Seq Analysis of Genes and Transposable Element Bioinformatics Analysis

RNA sequencing data was first pre-processed using Reaper (Davis, M P et al. (2013) *Methods* 63:41-49) to remove any Illumina adapter sequences and computationally depleted of ribosomal RNA sequences (GenBank identifiers: 18S, NR_003278.3; 28S, NR_003279.1; 5S, D14832.1; and 5.8S, K01367.1) using Bowtie 0.12.7 allowing 3 mismatches 71. For protein-coding gene expression analyses, pre-processed data was mapped to the mouse genome (mm10) using Bowtie 0.12.7 71 allowing 3 mismatches, and retaining uniquely mapping reads. Mouse transcript annotations were obtained from RefSeq, and reads corresponding to the exonic regions of each gene were calculated using a custom phyton script. For overlapping genes, reads corresponding to overlapping regions were divided equally. Gene differential expression was analysed using the DESeq R package80.

For TE expression analyses, data was mapped to the mm10 genome with 0 mismatches and considering reads that map to up to 10000 genomic positions as in ChIP sequencing analyses. The number of reads corresponding to TE regions annotated by the UCSC RepeatMasker track were calculated, scaling by the number of valid alignments for each read. Scaled reads for each TE family were summed, and normalized as RPM. Heatmaps were generated using the gplots R package, and differential expression analyses were performed using the DESeq R package (Anders and Huber. (2010) *Genome Biology* 11:R106). Comparisons of RNA-sequencing results from analyses based on uniquely mapping reads, and based on reads mapping to multiple genomic positions, showed very similar results.

Statistical Analyses

Unpaired student t test was used for statistical analysis in replicates of cell biology experiments. All error bars represent means±SEM or STDEV of independent biological replicates as indicated. A probability value of p<0.05 was considered statistically significant. Numbers of replicate experiments (n) are shown in figure legends. All graphs with no error bars represent n=1. To assess significant differences in signal enrichment at ESC promoters, enhancers or superenhancers by Sono-seq, ATAC-seq and ChIP-seq analysis upon CAF-1 knockdown or *Renilla* knockdown, a paired Wilcoxon rank sum test was used, where it is assumed that populations do not follow normal distributions. To identify differential ATAC-seq peaks between CAF-1 and *Renilla* knockdown samples, negative binomial models were used.

REFERENCES FOR BACKGROUND AND EXAMPLE 2

1 Burton, A. & Torres-Padilla, M. E. Chromatin dynamics in the regulation of cell fate allocation during early embryogenesis. *Nature reviews. Molecular cell biology* 15, 723-734, doi:10.1038/nrm3885 (2014).

2 Levine, M., Cattoglio, C. & Tjian, R. Looping back to leap forward: transcription enters a new era. *Cell* 157, 13-25, doi:10.1016/j.cell.2014.02.009 (2014).

3 Margueron, R. & Reinberg, D. Chromatin structure and the inheritance of epigenetic information. *Nature reviews. Genetics* 11, 285-296, doi:10.1038/nrg2752 (2010).

4 Yue, F. et al. A comparative encyclopedia of DNA elements in the mouse genome. *Nature* 515, 355-364, doi:10.1038/nature13992 (2014).

5 Lee, T. I. & Young, R. A. Transcriptional regulation and its misregulation in disease. *Cell* 152, 1237-1251, doi:10.1016/j.cell.2013.02.014 (2013).

6 Takahashi, K. & Yamanaka, S. Induction of pluripotent stem cells from mouse embryonic and adult fibroblast cultures by defined factors. *Cell* 126, 663-676, doi:10.1016/j.cell.2006.07.024 (2006).

7 Vierbuchen, T. & Wernig, M. Molecular roadblocks for cellular reprogramming. *Molecular cell* 47, 827-838, doi:10.1016/j.molcel.2012.09.008 (2012).

8 Iwafuchi-Doi, M. & Zaret, K. S. Pioneer transcription factors in cell reprogramming. *Genes & development* 28, 2679-2692, doi:10.1101/gad.253443.114 (2014).

9 Stadtfeld, M. & Hochedlinger, K. Induced pluripotency: history, mechanisms, and applications. *Genes & development* 24, 2239-2263, doi:10.1101/gad.1963910 (2010).

10 Polo, J. M. et al. A molecular roadmap of reprogramming somatic cells into iPS cells. *Cell* 151, 1617-1632, doi:10.1016/j.cell.2012.11.039 (2012).

11 Yang, C. S., Chang, K. Y. & Rana, T. M. Genome-wide functional analysis reveals factors needed at the transition steps of induced reprogramming. Cell reports 8, 327-337, doi:10.1016/j.celrep.2014.07.002 (2014).

12 Mikkelsen, T. S. et al. Dissecting direct reprogramming through integrative genomic analysis. *Nature* 454, 49-55, doi:10.1038/nature07056 (2008).

13 Onder, T. T. et al. Chromatin-modifying enzymes as modulators of reprogramming. *Nature* 483, 598-602, doi:10.1038/nature10953 (2012).

14 Rais, Y. et al. Deterministic direct reprogramming of somatic cells to pluripotency. *Nature* 502, 65-70, doi:10.1038/nature12587 (2013).

15 Krizhanovsky, V. & Lowe, S. W. Stem cells: The promises and perils of p53. *Nature* 460, 1085-1086, doi:10.1038/4601085a (2009).

16 Dejosez, M., Ura, H., Brandt, V. L. & Zwaka, T. P. Safeguards for cell cooperation in mouse embryogenesis shown by genome-wide cheater screen. *Science* 341, 1511-1514, doi:10.1126/science.1241628 (2013).

17 Qin, H. et al. Systematic identification of barriers to human iPSC generation. *Cell* 158, 449-461, doi:10.1016/j.cell.2014.05.040 (2014).

18 dos Santos, R. L. et al. MBD3/NuRD facilitates induction of pluripotency in a context-dependent manner. *Cell stem cell* 15, 102-110, doi:10.1016/j.stem.2014.04.019 (2014).

19 Luo, M. et al. NuRD blocks reprogramming of mouse somatic cells into pluripotent stem cells. *Stem cells* 31, 1278-1286, doi:10.1002/stem.1374 (2013).

20 Schwarz, B. A., Bar-Nur, O., Silva, J. C. & Hochedlinger, K. Nanog is dispensable for the generation of induced pluripotent stem cells. *Current biology: CB* 24, 347-350, doi:10.1016/j.cub.2013.12.050 (2014).

21 Stuart, H. T. et al. NANOG amplifies STAT3 activation and they synergistically induce the naive pluripotent program. *Current biology: CB* 24, 340-346, doi:10.1016/j.cub.2013.12.040 (2014).

22 Carter, A. C., Davis-Dusenbery, B. N., Koszka, K., Ichida, J. K. & Eggan, K. Nanog-independent reprogramming to iPSCs with canonical factors. *Stem cell reports* 2, 119-126, doi:10.1016/j.stemcr.2013.12.010 (2014).

23 Theunissen, T. W. et al. Nanog overcomes reprogramming barriers and induces pluripotency in minimal conditions. *Current biology: CB* 21, 65-71, doi:10.1016/j.cub.2010.11.074 (2011).

24 Apostolou, E. & Hochedlinger, K. Chromatin dynamics during cellular reprogramming. *Nature* 502, 462-471, doi:10.1038/nature12749 (2013).

25 Suva, M. L., Riggi, N. & Bernstein, B. E. Epigenetic reprogramming in cancer. *Science* 339, 1567-1570, doi:10.1126/science.1230184 (2013).

26 Stadtfeld, M., Maherali, N., Borkent, M. & Hochedlinger, K. A reprogrammable mouse strain from gene-targeted embryonic stem cells. *Nature methods* 7, 53-55, doi:10.1038/nmeth.1409 (2010).

27 Zuber, J. et al. RNAi screen identifies Brd4 as a therapeutic target in acute myeloid leukaemia. *Nature* 478, 524-528, doi:10.1038/nature10334 (2011).

28 Fellmann, C. et al. An optimized microRNA backbone for effective single-copy RNAi. *Cell reports* 5, 1704-1713, doi:10.1016/j.celrep.2013.11.020 (2013).

29 Chen, J. et al. H3K9 methylation is a barrier during somatic cell reprogramming into iPSCs. *Nature genetics* 45, 34-42, doi:10.1038/ng.2491 (2013).

30 Soufi, A., Donahue, G. & Zaret, K. S. Facilitators and impediments of the pluripotency reprogramming factors' initial engagement with the genome. *Cell* 151, 994-1004, doi:10.1016/j.cell.2012.09.045 (2012).

31 Sridharan, R. et al. Proteomic and genomic approaches reveal critical functions of H3K9 methylation and heterochromatin protein-1gamma in reprogramming to pluripotency. *Nature cell biology* 15, 872-882, doi:10.1038/ncb2768 (2013).

32 Hong, H. et al. Suppression of induced pluripotent stem cell generation by the p53-p21 pathway. *Nature* 460, 1132-1135, doi:10.1038/nature08235 (2009).

33 Kawamura, T. et al. Linking the p53 tumour suppressor pathway to somatic cell reprogramming. *Nature* 460, 1140-1144, doi:10.1038/nature08311 (2009).

34 Li, H. et al. The Ink4/Arf locus is a barrier for iPS cell reprogramming. *Nature* 460, 1136-1139, doi:10.1038/nature08290 (2009).

35 Marion, R. M. et al. A p53-mediated DNA damage response limits reprogramming to ensure iPS cell genomic integrity. *Nature* 460, 1149-1153, doi:10.1038/nature08287 (2009).

36 Utikal, J. et al. Immortalization eliminates a roadblock during cellular reprogramming into iPS cells. *Nature* 460, 1145-1148, doi:10.1038/nature08285 (2009).

37 Quivy, J. P., Gerard, A., Cook, A. J., Roche, D. & Almouzni, G. The HP1-p150/CAF-1 interaction is required for pericentric heterochromatin replication and S-phase progression in mouse cells. *Nature structural & molecular biology* 15, 972-979 (2008).

38 Hoek, M. & Stillman, B. Chromatin assembly factor 1 is essential and couples chromatin assembly to DNA replication in vivo. *Proceedings of the National Academy of Sciences of the United States of America* 100, 12183-12188, doi:10.1073/pnas.1635158100 (2003).

39 Ye, X. et al. Defective S phase chromatin assembly causes DNA damage, activation of the S phase checkpoint, and S phase arrest. *Molecular cell* 11, 341-351 (2003).

40 Chanda, S. et al. Generation of induced neuronal cells by the single reprogramming factor ASCL1. *Stem cell reports* 3, 282-296, doi:10.1016/j.stemcr.2014.05.020 (2014).

41 Bussmann, L. H. et al. A robust and highly efficient immune cell reprogramming system. *Cell stem cell* 5, 554-566, doi:10.1016/j.stem.2009.10.004 (2009).

42 Smith, S. & Stillman, B. Purification and characterization of CAF-I, a human cell factor required for chromatin assembly during DNA replication in vitro. Cell 58, 15-25 (1989).

43 Auerbach, R. K. et al. Mapping accessible chromatin regions using Sono-Seq. *Proceedings of the National Academy of Sciences of the United States of America* 106, 14926-14931, doi:10.1073/pnas.0905443106 (2009).

44 Heinz, S., Romanoski, C. E., Benner, C. & Glass, C. K. The selection and function of cell type-specific enhancers. *Nature reviews. Molecular cell biology*, doi:10.1038/nrm3949 (2015).

45 Shen, Y. et al. A map of the cis-regulatory sequences in the mouse genome. *Nature* 488, 116-120, doi:10.1038/nature11243 (2012).

46 Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nature methods* 10, 1213-1218, doi:10.1038/nmeth.2688 (2013).

47 Hnisz, D. et al. Super-enhancers in the control of cell identity and disease. *Cell* 155, 934-947, doi:10.1016/j.cell.2013.09.053 (2013).

48 Pott, S. & Lieb, J. D. What are super-enhancers? *Nature genetics* 47, 8-12, doi:10.1038/ng.3167 (2014).

49 Whyte, W. A. et al. Master transcription factors and mediator establish super enhancers at key cell identity genes. *Cell* 153, 307-319, doi:10.1016/j.cell.2013.03.035 (2013).

50 Marson, A. et al. Connecting microRNA genes to the core transcriptional regulatory circuitry of embryonic stem cells. *Cell* 134, 521-533, doi:10.1016/j.cell.2008.07.020 (2008).

51 Tahmasebi, S., Ghorbani, M., Savage, P., Gocevski, G. & Yang, X. J. The SUMO conjugating enzyme Ubc9 is required for inducing and maintaining stem cell pluripotency. *Stem cells* 32, 1012-1020, doi:10.1002/stem.1600 (2014).

52 Bilodeau, S., Kagey, M. H., Frampton, G. M., Rahl, P. B. & Young, R. A. SetDB1 contributes to repression of genes encoding developmental regulators and maintenance of ES cell state. *Genes & development* 23, 2484-2489, doi:10.1101/gad.1837309 (2009).

53 Mochizuki, K. et al. The bromodomain protein Brd4 stimulates G1 gene transcription and promotes progression to S phase. *The Journal of biological chemistry* 283, 9040-9048, doi:10.1074/jbc.M707603200 (2008).

54 Houlard, M. et al. CAF-1 is essential for heterochromatin organization in pluripotent embryonic cells. *PLoS genetics* 2, e181, doi:10.1371/journal.pgen.0020181 (2006).

55 Nacerddine, K. et al. The SUMO pathway is essential for nuclear integrity and chromosome segregation in mice. *Developmental cell* 9, 769-779, doi:10.1016/j.devcel.2005.10.007 (2005).

56 Schmidt, C. S. et al. Global DNA hypomethylation prevents consolidation of differentiation programs and allows reversion to the embryonic stem cell state. *PloS one* 7, e52629, doi:10.1371/journal.pone.0052629 (2012).

57 Henderson, D. S., Banga, S. S., Grigliatti, T. A. & Boyd, J. B. Mutagen sensitivity and suppression of position-effect variegation result from mutations in mus209, the Drosophila gene encoding PCNA. *The EMBO journal* 13, 1450-1459 (1994).

58 Ng, R. K. et al. Epigenetic restriction of embryonic cell lineage fate by methylation of Elf5. *Nature cell biology* 10, 1280-1290, doi:10.1038/ncb1786 (2008).

59 Davis, R. L., Weintraub, H. & Lassar, A. B. Expression of a single transfected cDNA converts fibroblasts to myoblasts. *Cell* 51, 987-1000 (1987).

60 Ray-Gallet, D. et al. Dynamics of histone H3 deposition in vivo reveal a nucleosome gap-filling mechanism for H3.3 to maintain chromatin integrity. *Molecular cell* 44, 928-941, doi:10.1016/j.molcel.2011.12.006 (2011).

61 Zentner, G. E. & Henikoff, S. Regulation of nucleosome dynamics by histone modifications. *Nature structural & molecular biology* 20, 259-266, doi:10.1038/nsmb.2470 (2013).

62 Skene, P. J. & Henikoff, S. Chromatin roadblocks to reprogramming 50 years on. *BMC biology* 10, 83, doi:10.1186/1741-7007-10-83 (2012).

63 Jullien, J. et al. HIRA dependent H3.3 deposition is required for transcriptional reprogramming following nuclear transfer to *Xenopus* oocytes. *Epigenetics & chromatin* 5, 17, doi:10.1186/1756-8935-5-17 (2012).

64 Wen, D., Banaszynski, L. A., Rosenwaks, Z., Allis, C. D. & Rafii, S. H3.3 replacement facilitates epigenetic reprogramming of donor nuclei in somatic cell nuclear transfer embryos. *Nucleus* 5, 369-375, doi:10.4161/nucl.36231 (2014).

65 Matoba, S. et al. Embryonic development following somatic cell nuclear transfer impeded by persisting histone methylation. *Cell* 159, 884-895, doi:10.1016/j.cell.2014.09.055 (2014).

66 Consortium, S. G. *Epigenetics Probes Collection*

67 Bar-Nur, O. et al. Small molecules facilitate rapid and synchronous iPSC generation. *Nature methods* 11, 1170-1176, doi:10.1038/nmeth.3142 (2014).

68 Zuber, J. et al. Toolkit for evaluating genes required for proliferation and survival using tetracycline-regulated RNAi. *Nature biotechnology* 29, 79-83, doi:10.1038/nbt.1720 (2011).

69 Bernstein, B. E. et al. Genomic maps and comparative analysis of histone modifications in human and mouse. *Cell* 120, 169-181, doi:10.1016/j.cell.2005.01.001 (2005).

70 Langmead, B., Trapnell, C., Pop, M. & Salzberg, S. L. Ultrafast and memory efficient alignment of short DNA sequences to the human genome. *Genome biology* 10, R25, doi:10.1186/gb-2009-10-3-r25 (2009).

71 Kharchenko, P. V., Tolstorukov, M. Y. & Park, P. J. Design and analysis of ChIPseq experiments for DNA-binding proteins. *Nature biotechnology* 26, 1351-1359, doi:10.1038/nbt.1508 (2008).

72 Li, H. & Durbin, R. Fast and accurate short read alignment with Burrows-Wheeler transform. *Bioinformatics* 25, 1754-1760, doi:10.1093/bioinformatics/btp324 (2009).

73 Sabo, P. J. et al. Discovery of functional noncoding elements by digital analysis of chromatin structure. *Proceedings of the National Academy of Sciences of the United States of America* 101, 16837-16842, doi:10.1073/pnas.0407387101(2004).

74 Ross-Innes, C. S. et al. Differential oestrogen receptor binding is associated with clinical outcome in breast cancer. *Nature* 481, 389-393, doi:10.1038/nature10730 (2012)

The invention claimed is:

1. A method for performing cellular reprogramming, the method comprising:
   (a) contacting a somatic cell with an inhibitor of the CAF-1 complex, and an inhibitor of Nudt21, and
   (b) subjecting the somatic cell to a reprogramming protocol,
thereby reprogramming the somatic cell to an induced pluripotent stem cell (iPSC).

2. The method of claim 1, wherein the speed and/or efficiency of cellular reprogramming to iPSCs is increased in the presence of the inhibitors as compared to the speed and/or efficiency of cellular reprogramming performed in the absence of the inhibitors.

3. The method of claim 2, wherein the measure of efficiency of cellular reprogramming comprises an increase in the total number of reprogrammed cells relative to reprogramming in the absence of said inhibitors, and/or wherein the measure of speed of cellular reprogramming comprises the appearance of reprogrammed cells at an earlier time point than occurs when reprogramming in the absence of said inhibitors.

4. The method of claim 1, wherein at least one of the inhibitors comprises an RNA interference molecule or an antibody.

5. The method of claim 1, wherein step (a) is performed before or during step (b).

6. The method of claim 1, wherein the reprogramming of step (b) comprises induction of Oct-4/Klf4/Sox-2/c-Myc (OKSM) expression.

7. The method of claim 1, wherein the reprogramming step does not comprise forced expression of c-Myc.

8. The method of claim 1, wherein the somatic cell comprises a fibroblast.

9. The method of claim 1, wherein the inhibitor of the CAF-1 complex inhibits the Chaf1a and/or Chaf1b subunit of the CAF-1 complex.

10. A method for performing cellular reprogramming, the method comprising:
 (a) contacting a somatic cell with an inhibitor of Nudt21, and
 (b) subjecting the somatic cell to a reprogramming protocol,
thereby reprogramming the somatic cell to an induced pluripotent stem cell (iPSC).

* * * * *

UNITED STATES PATENT AND TRADEMARK OFFICE
CERTIFICATE OF CORRECTION

PATENT NO. : 10,059,945 B2
APPLICATION NO. : 15/443632
DATED : August 28, 2018
INVENTOR(S) : Hochedlinger et al.

Page 1 of 1

It is certified that error appears in the above-identified patent and that said Letters Patent is hereby corrected as shown below:

In the Specification

At Column 1, Line 15, after the first paragraph, the following heading and paragraph should be inserted:
-- GOVERNMENT SUPPORT
This invention was made with government support under Grant Number HD058013 awarded by the National Institutes of Health and Grant No. W8IXWH-13-1-0206 awarded by the U.S. Army. The government has certain rights in the invention. --

Signed and Sealed this
Fifteenth Day of October, 2019

Andrei Iancu
*Director of the United States Patent and Trademark Office*

SEQUENCE LISTING

<160> NUMBER OF SEQ ID NOS: 23

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaaactggg gcacagatga tgcgg                                          25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcctcccct acccggtaga                                                20

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tagccccttg aattccgagg cagtaggca                                      29

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgatacggc gaccaccgag atctacacct aaagtagccc cttgaattc                49

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caagcagaag acggcatacg agacgatagt gaagccacag atgta                    45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagcagaag acggcatacg agacactagt gaagccacag atgta                    45

```
<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caagcagaag acggcatacg agactatagt gaagccacag atgta            45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagcagaag acggcatacg agaccttagt gaagccacag atgta            45

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggcttcttt tacttctgca tac                                    23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaggaaggag tcaagactga gaa                                    23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aggtcggtgt gaacggattt g                                      21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagtgaagcc acagatgta                                         19
```

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatgatacgg cgaccaccga ctaaagtagc cccttgaatt c            41

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggtatgga cccatcattt                                    20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggaatctga tctgcctcat tg                                 22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgtagaccat gtagttgagg tca                                23

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (22)..(23)
<223> OTHER INFORMATION: This region may be "ga" or "tg" or "at"

<400> SEQUENCE: 17
caagcagaag acggcatacg addtagtgaa gccacagatg ta           42

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
gctgtattcc cctccatcgt g                                              21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacggttggc cttagggttc ag                                             22

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggctccttgc tgtcattcat cttccac                                        27

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccgccgtc aggatctgga agttgg                                         26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgtcttcct caactttctc cttgg                                          25

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgcggacagc cgcggccgtg gattgc                                         26
```